(12) United States Patent  (10) Patent No.: US 7,854,727 B2
Belsley                    (45) Date of Patent:    Dec. 21, 2010

(54) ADJUSTABLE DEVICE DELIVERY SYSTEM

(76) Inventor: Scott J. Belsley, 666 Greenwich St., Apt 352, New York, NY (US) 10014

( * ) Notice: Subject to any disclaimer, the term of this patent is extended or adjusted under 35 U.S.C. 154(b) by 990 days.

(21) Appl. No.: 10/558,313

(22) PCT Filed: May 21, 2004

(86) PCT No.: PCT/US2004/015962

§ 371 (c)(1), (2), (4) Date: Feb. 1, 2007

(87) PCT Pub. No.: WO2004/105830

PCT Pub. Date: Dec. 9, 2004

(65) Prior Publication Data

US 2007/0260196 A1    Nov. 8, 2007

Related U.S. Application Data

(60) Provisional application No. 60/472,875, filed on May 23, 2003.

(51) Int. Cl.
*A61M 25/00* (2006.01)
(52) U.S. Cl. .................................................. 604/264
(58) Field of Classification Search ................. 604/246, 604/523, 528, 95.01, 117; 600/123, 146, 600/107
See application file for complete search history.

(56) References Cited

U.S. PATENT DOCUMENTS

| 4,405,314 A | 9/1983 | Cope |
| 4,522,206 A | 6/1985 | Whipple et al. |
| 4,582,181 A | 4/1986 | Samson |
| 4,932,952 A | 6/1990 | Wojciechowicz, Jr. |
| 4,947,864 A | 8/1990 | Shockey et al. |
| 4,998,917 A | 3/1991 | Gaiser et al. |
| 5,183,470 A | 2/1993 | Wettermann |
| 5,190,528 A | 3/1993 | Fonger et al. |
| 5,368,046 A * | 11/1994 | Scarfone et al. ............. 600/567 |
| 5,413,581 A | 5/1995 | Goy |
| 5,439,006 A | 8/1995 | Brennen et al. |

(Continued)

*Primary Examiner*—Manuel A Mendez
(74) *Attorney, Agent, or Firm*—McDonnell Boehnen Hulbert & Berghoff

(57) ABSTRACT

Herein are described components and use of an adjustable device delivery system including an adjustable internal door which allows angled deployment of medical devices, non-medical devices and electromagnetic radiation. In one embodiment, a slotted outer cannula is used with an inner drive cannula to guide the motion of an adjustable interior door that allows delivery of devices, such as medical instruments, at user-defined angles. The invention also provides device delivery systems that permit withdrawal of the adjustable device delivery system without disruption of a device placed therewith. The device delivery systems of the invention are provided having a steering system that permits exact control of the angle of the adjustable internal door while providing support against longitudinal forces. Also provided are embodiments of the devices of the invention comprising a locking system that provides frictional resistance to overcome unwanted displacement of the door angle and drive system when, for example, manipulation of the device delivery system during its use increases the forces applied to the door surface. The invention further provides methods for using the device delivery systems provided herein for delivering or receiving electromagnetic waves by deflection or reflection of such radiation by the adjustable internal door. The invention also provides methods for steering a device or device delivery system within a confined space.

42 Claims, 52 Drawing Sheets

U.S. PATENT DOCUMENTS

| | | | |
|---|---|---|---|
| 5,460,168 A | * 10/1995 | Masubuchi et al. | 600/123 |
| 5,464,395 A | 11/1995 | Faxon et al. | |
| 5,569,157 A | * 10/1996 | Nakazawa et al. | 600/107 |
| 5,655,548 A | 8/1997 | Nelson et al. | |
| 6,022,342 A | * 2/2000 | Mukherjee | 604/523 |
| 6,126,649 A | 10/2000 | VanTassel et al. | |
| 6,511,458 B2 | 1/2003 | Milo et al. | |
| 6,514,217 B1 | 2/2003 | Selmon et al. | |
| 6,530,914 B1 | 3/2003 | Mickley | |

* cited by examiner

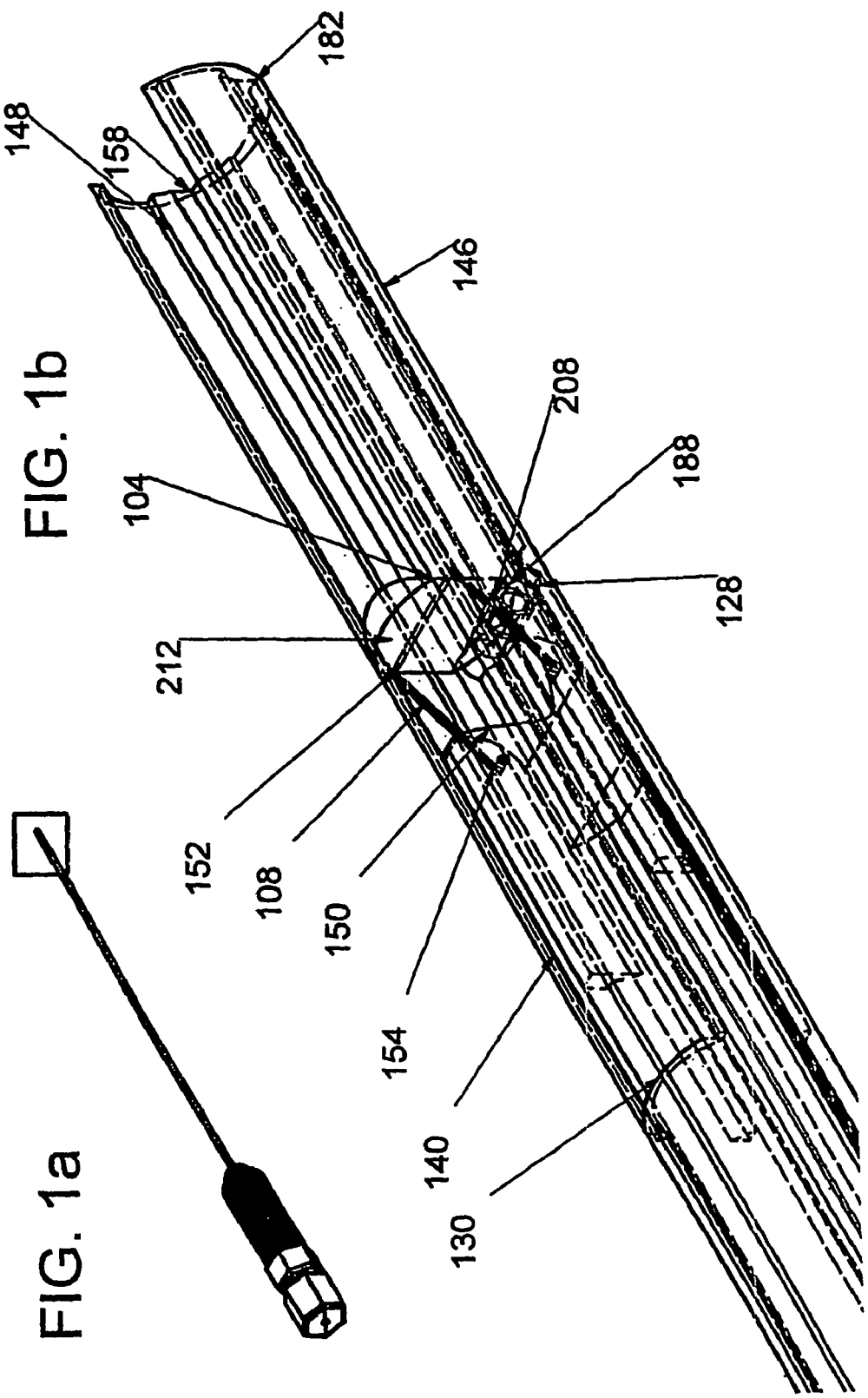

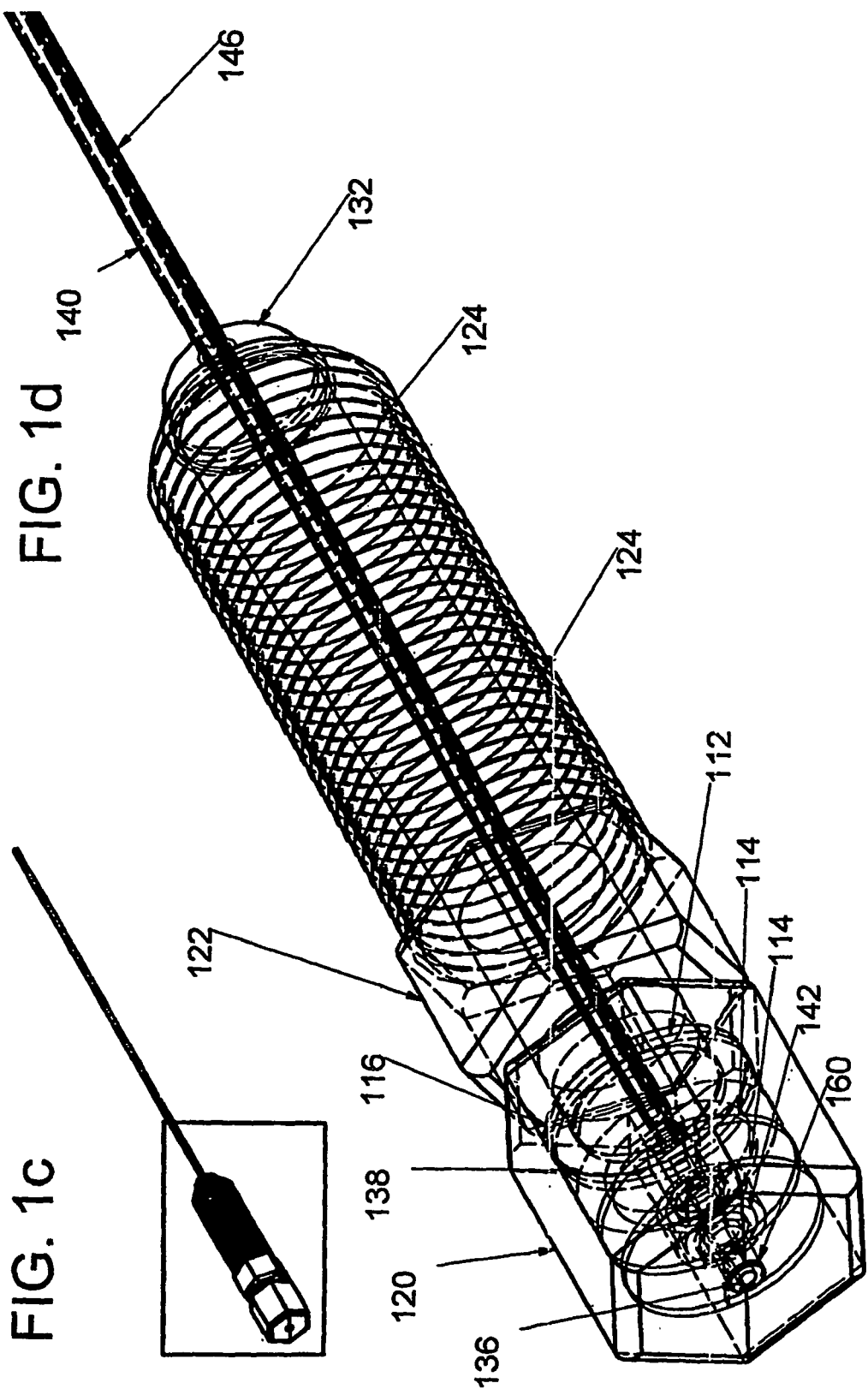

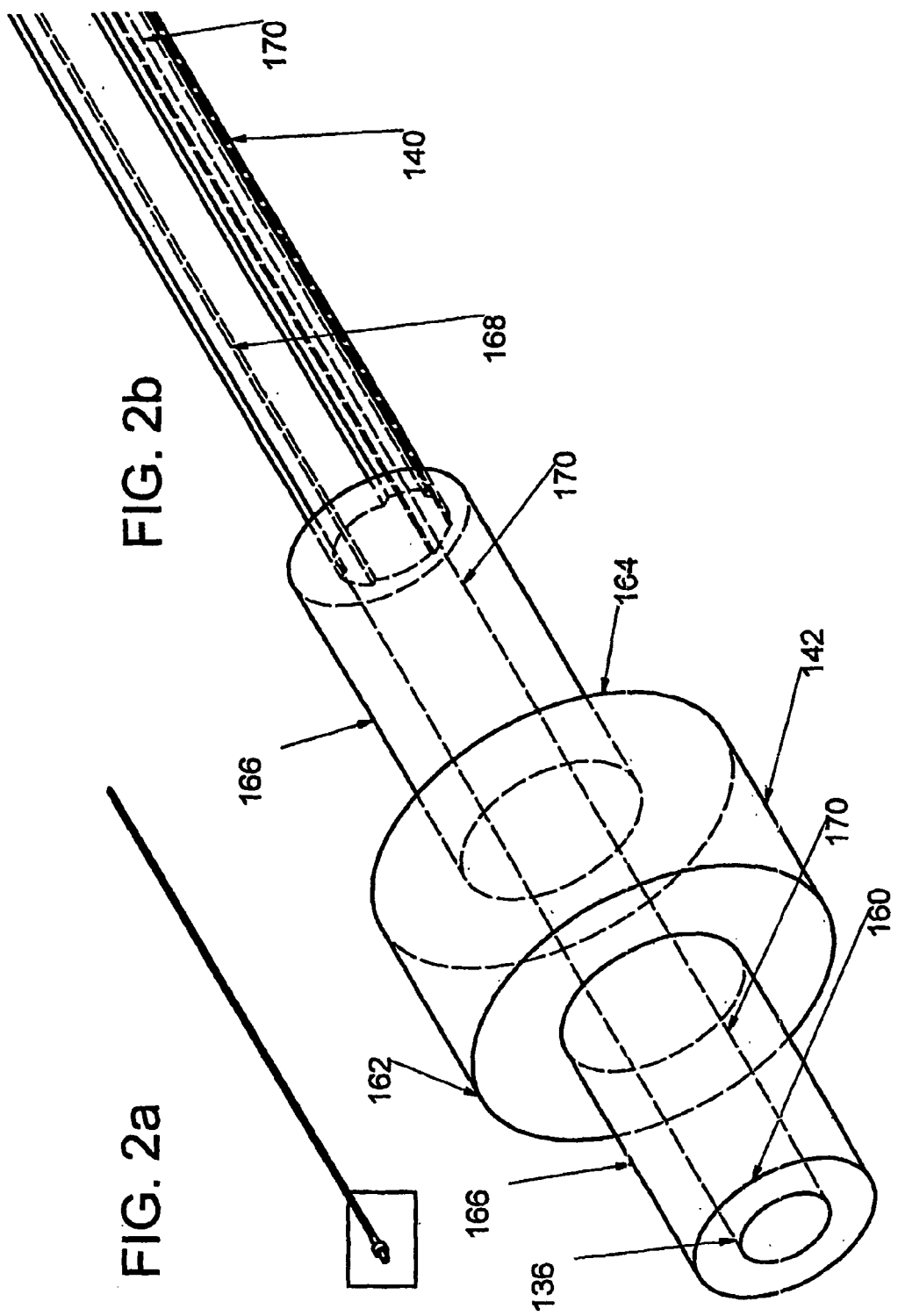

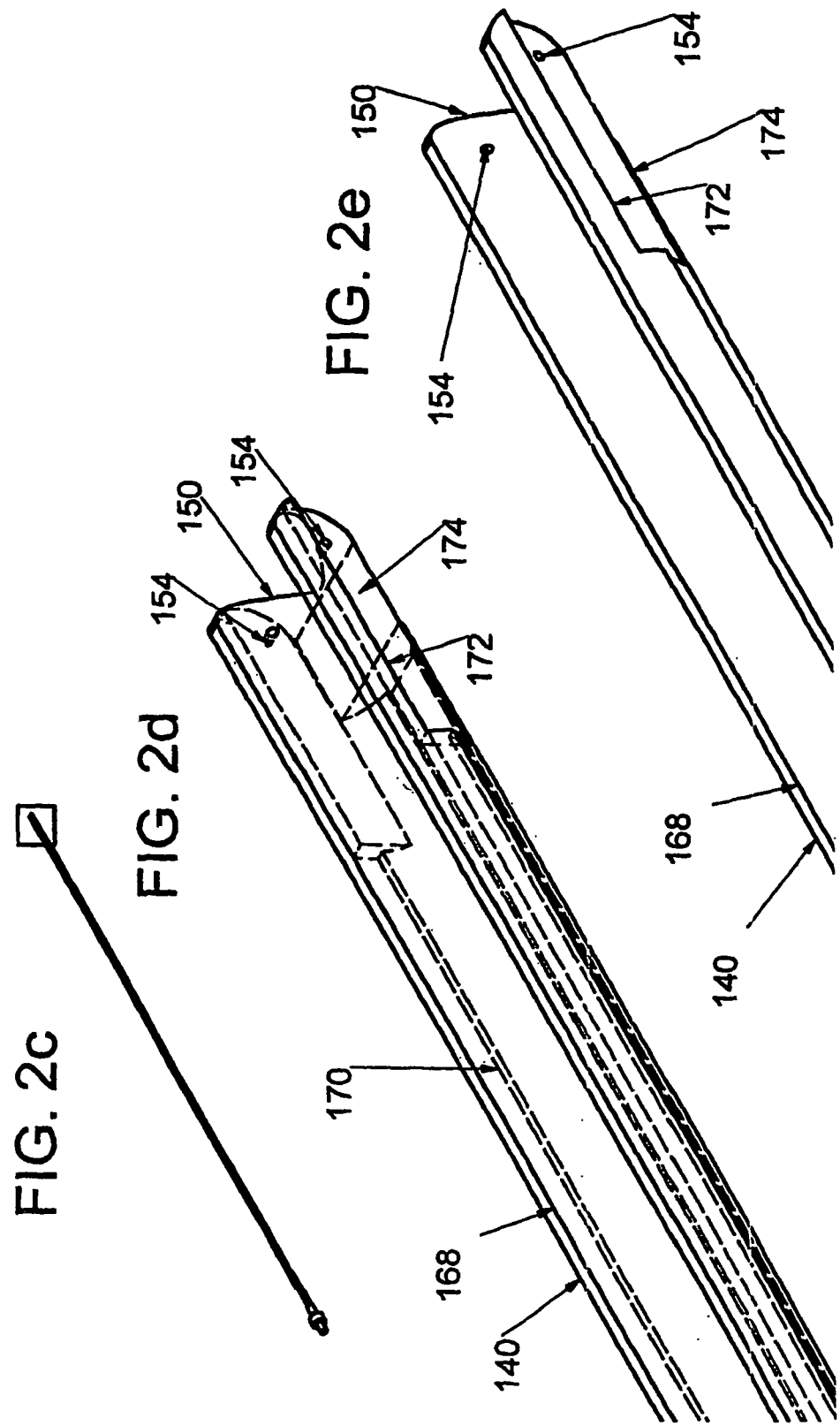

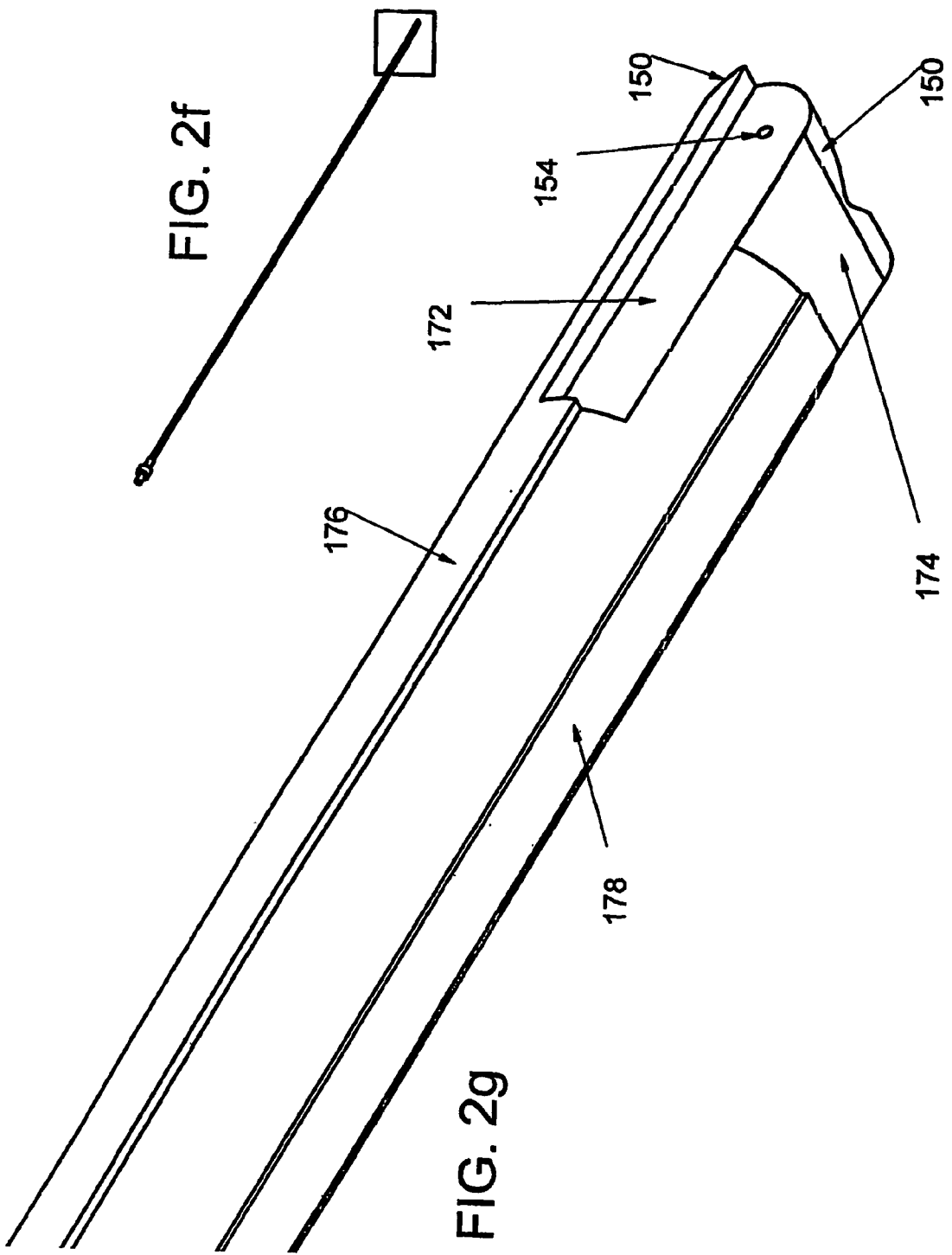

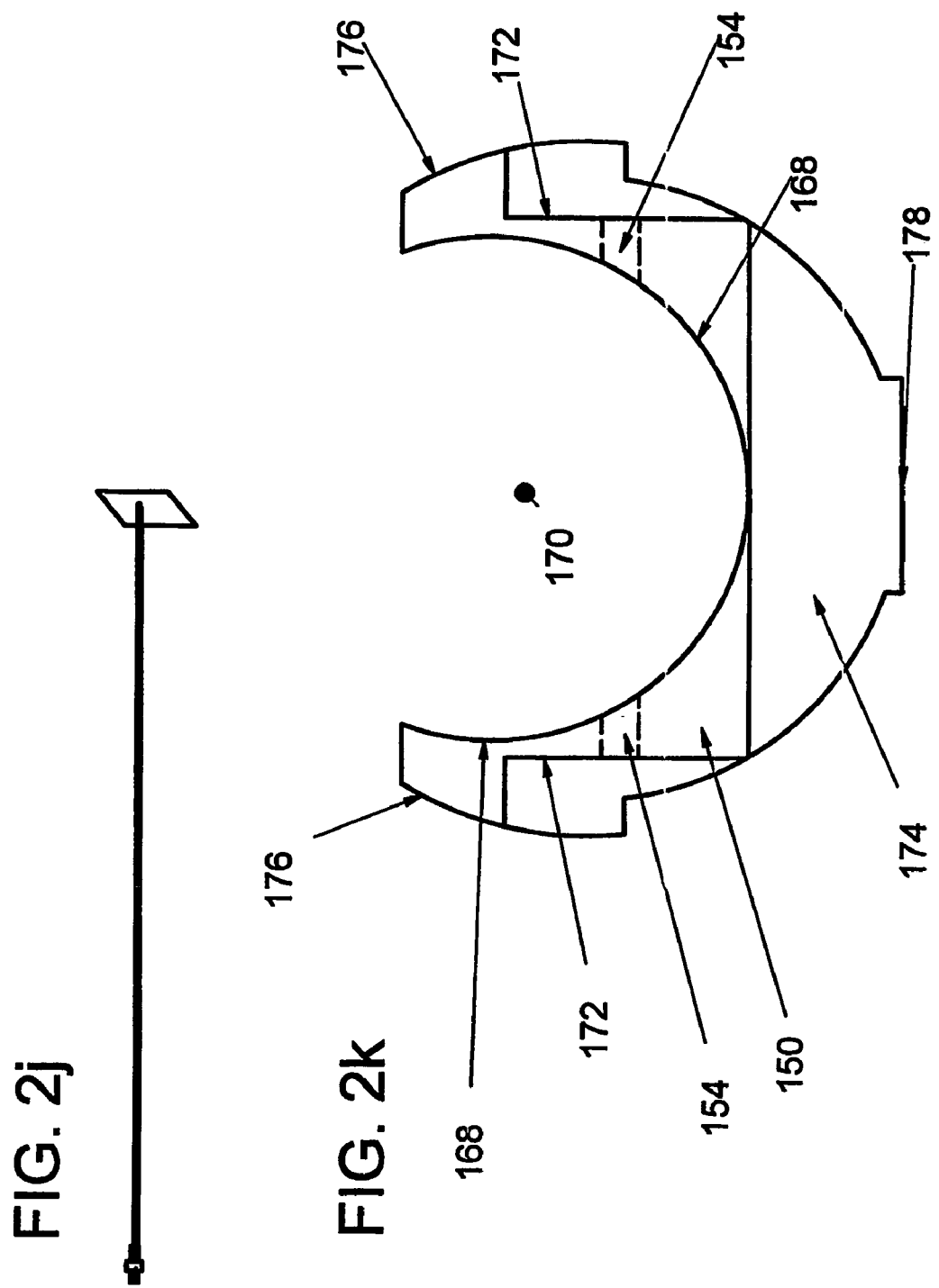

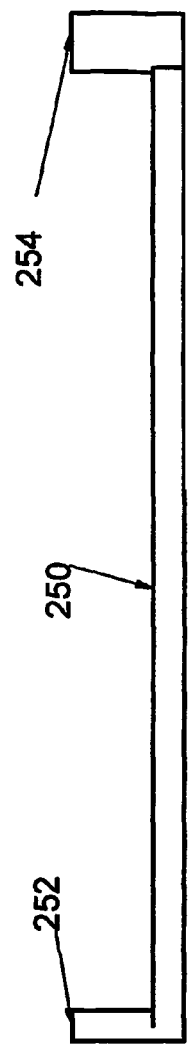
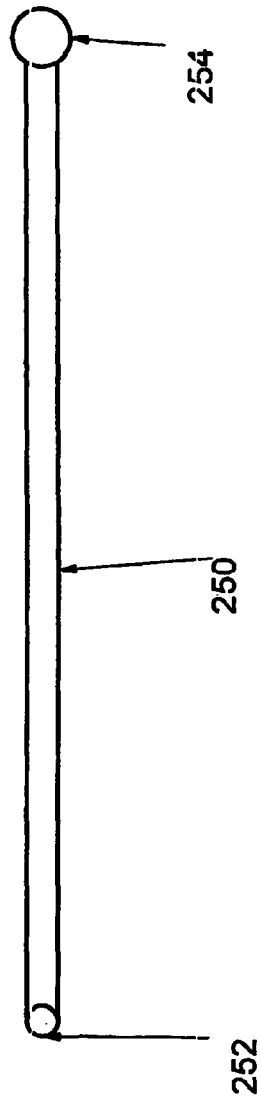
FIG. 4a
FIG. 4b

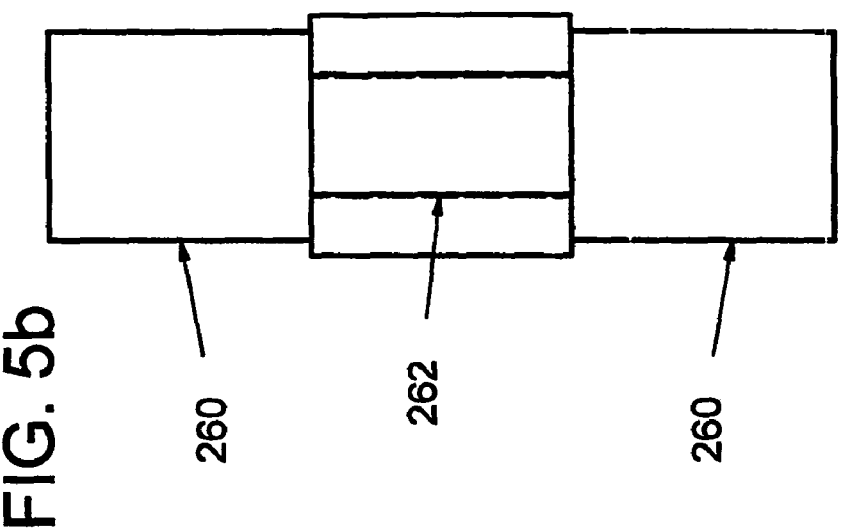
FIG. 5b
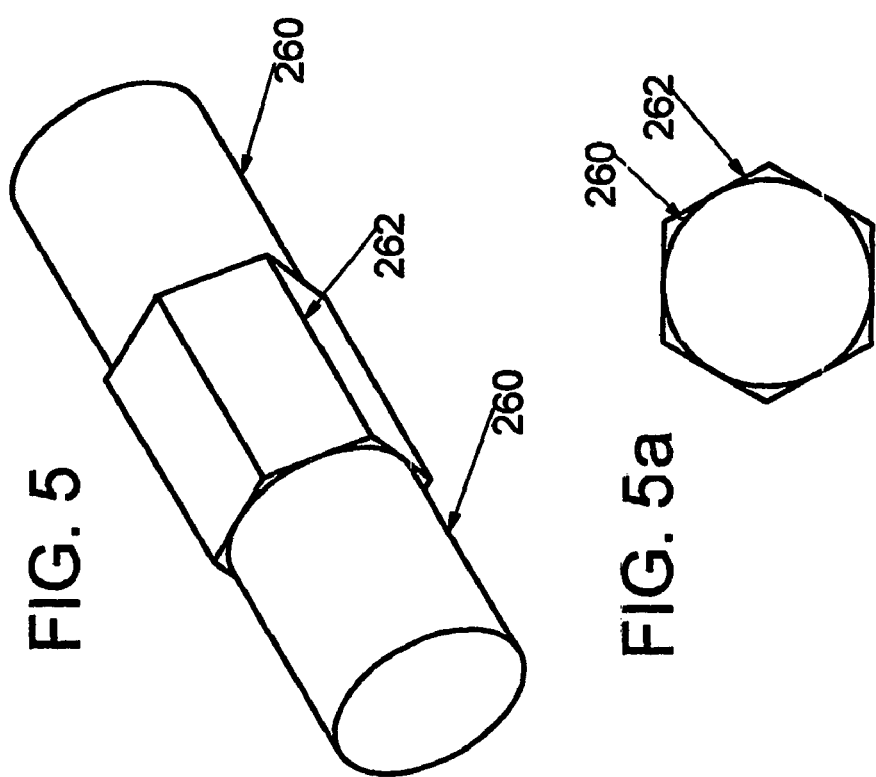
FIG. 5
FIG. 5a

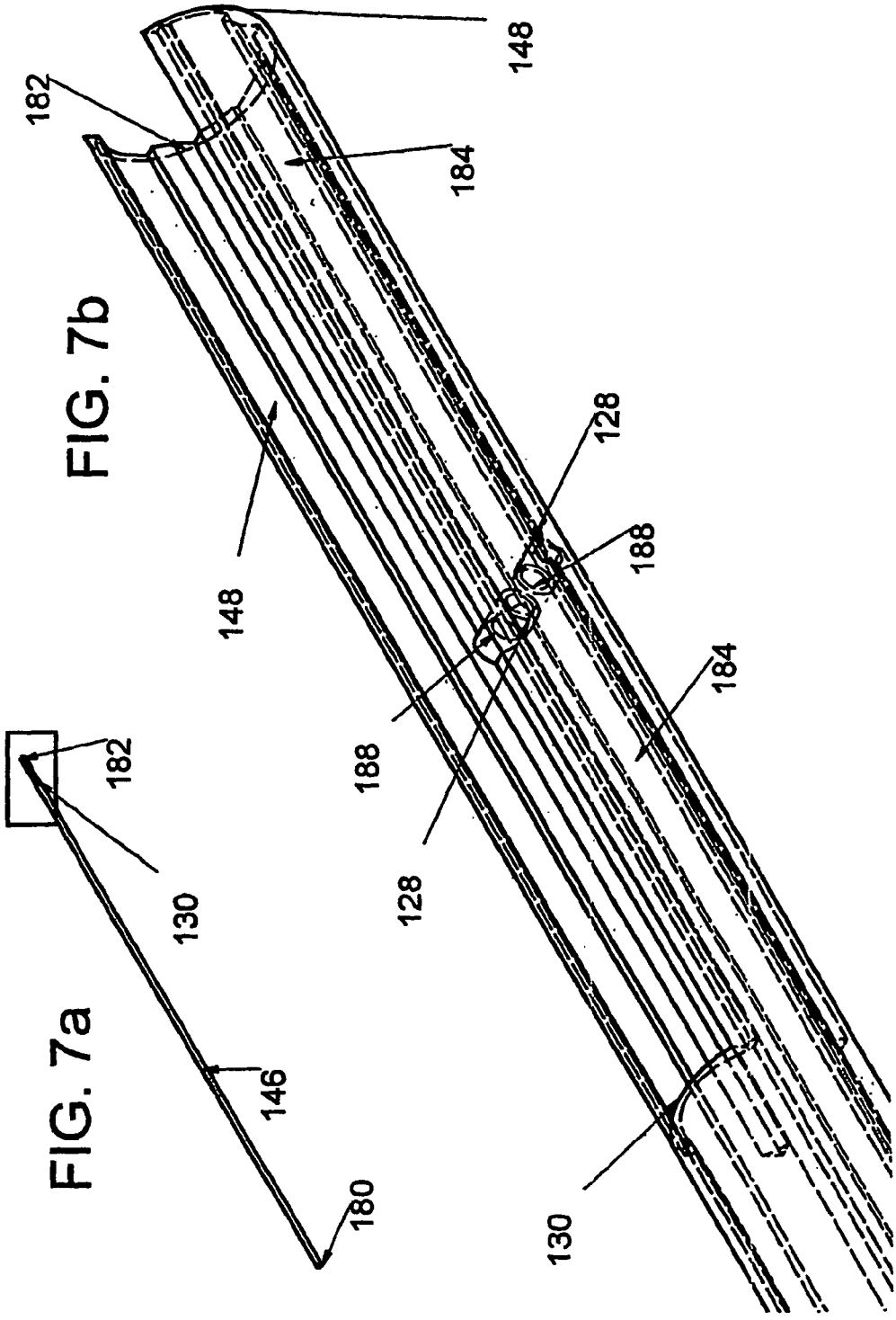

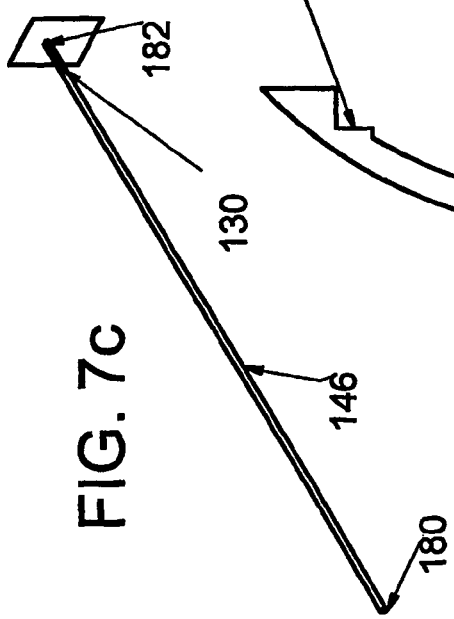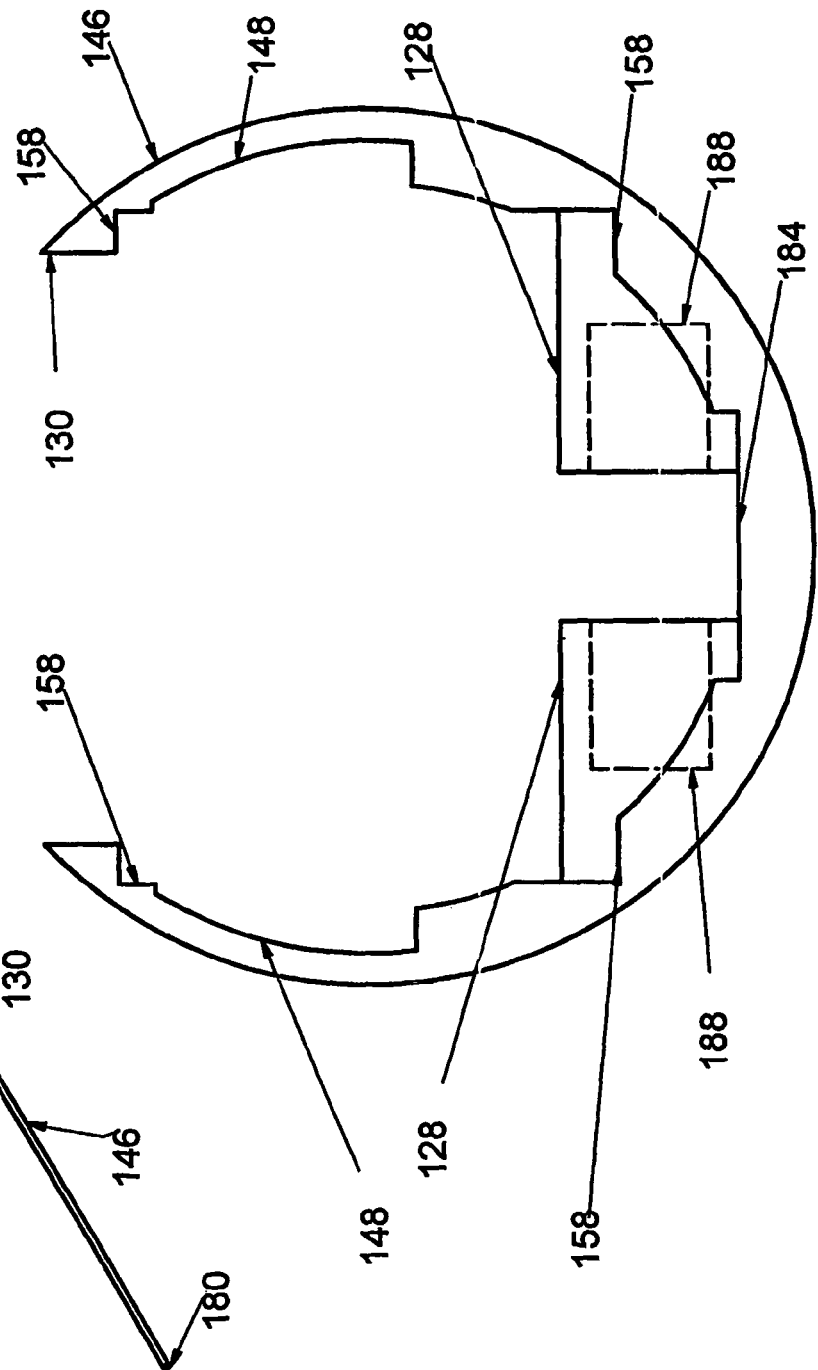

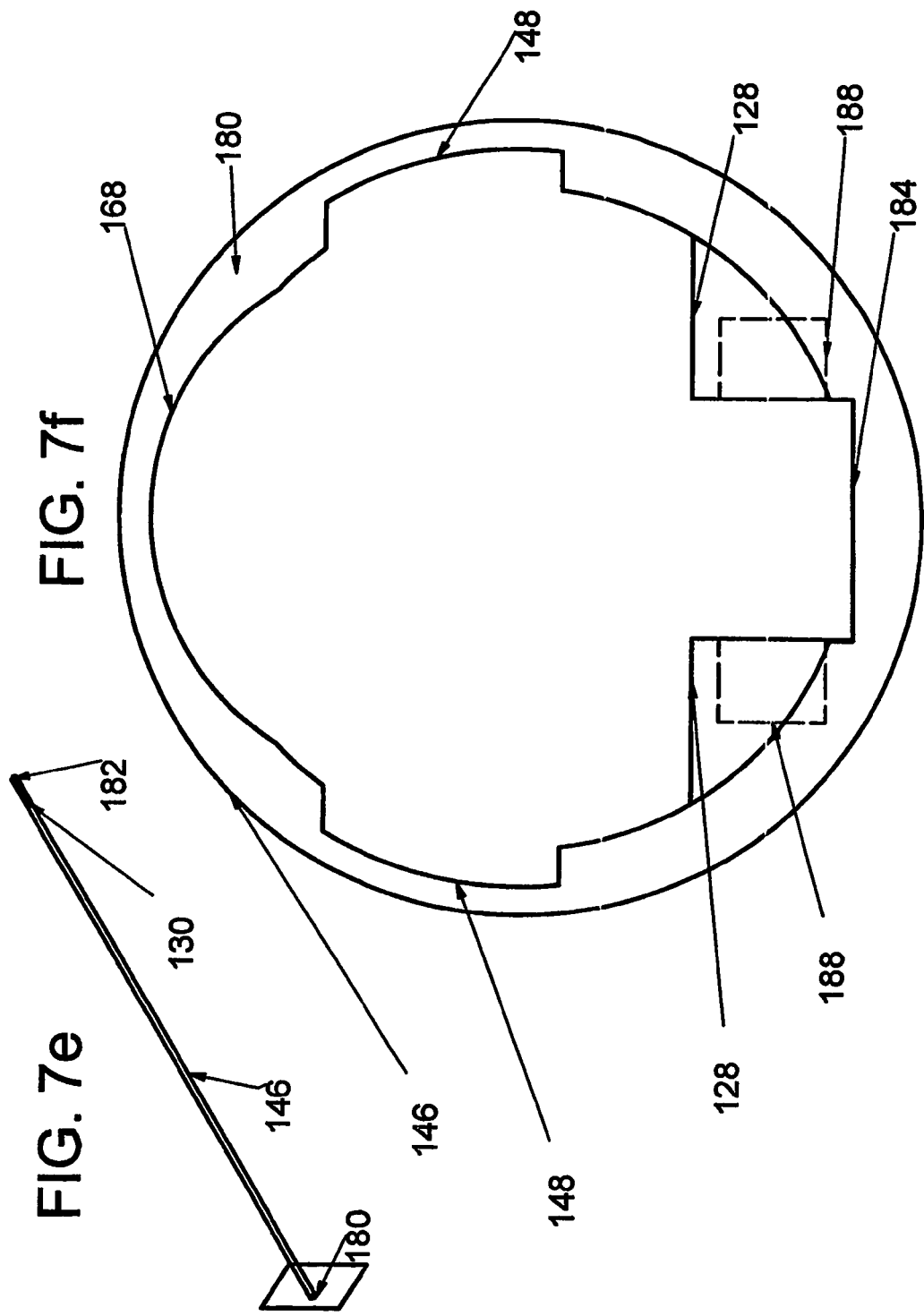

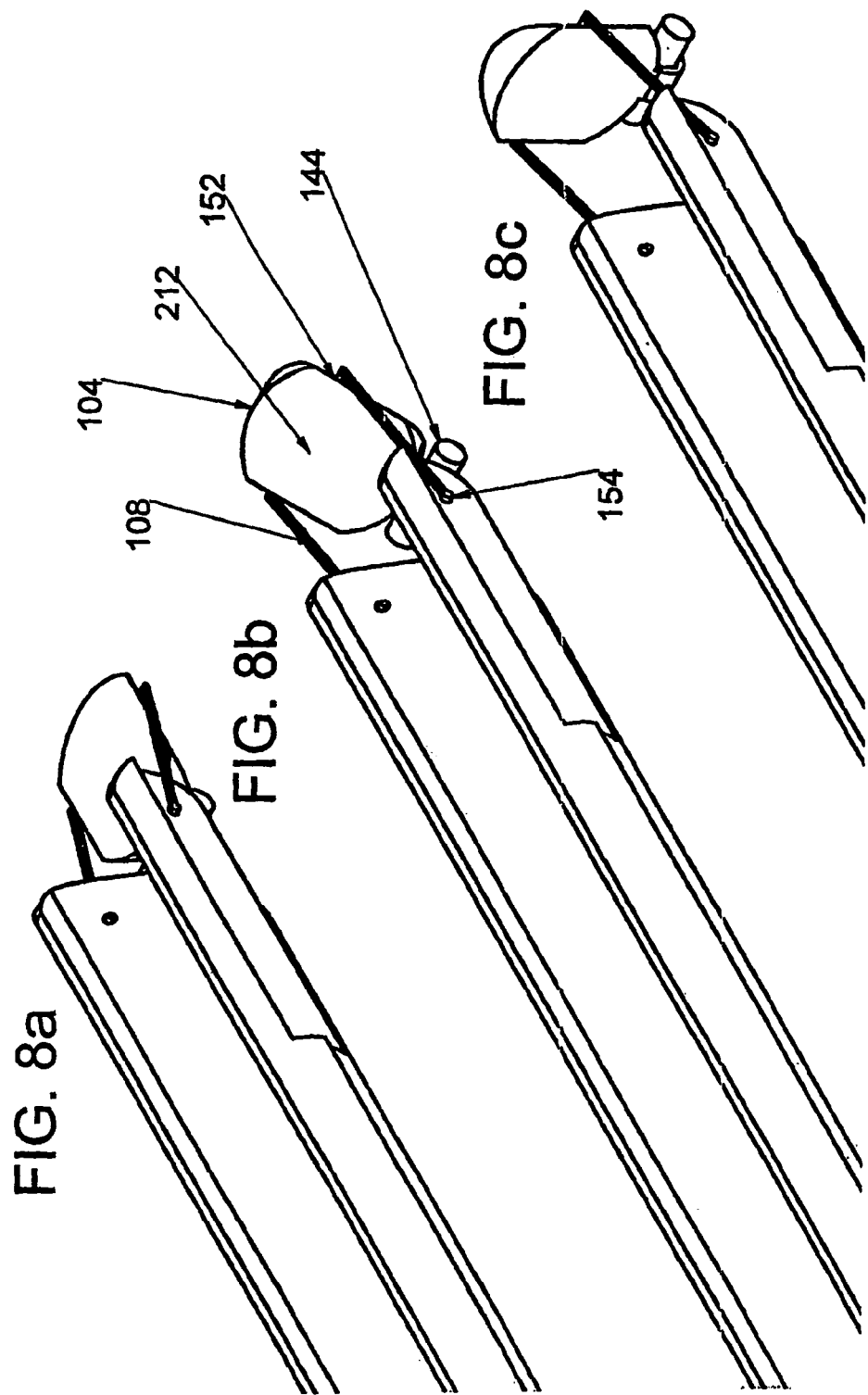

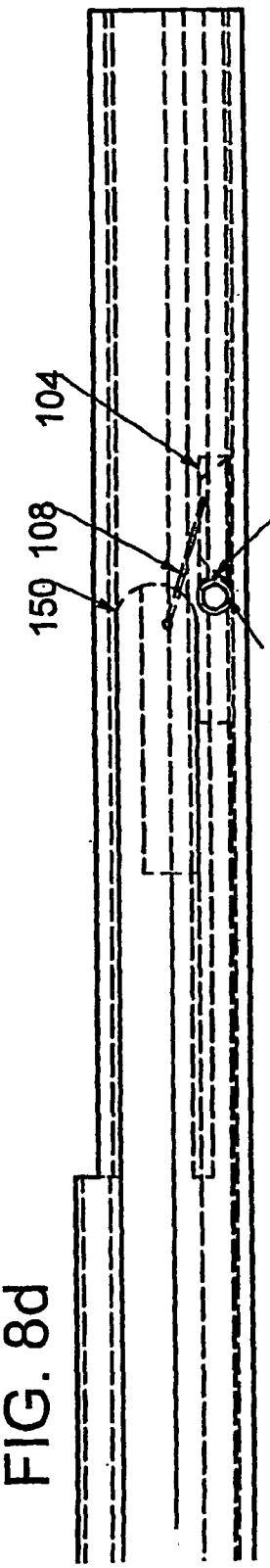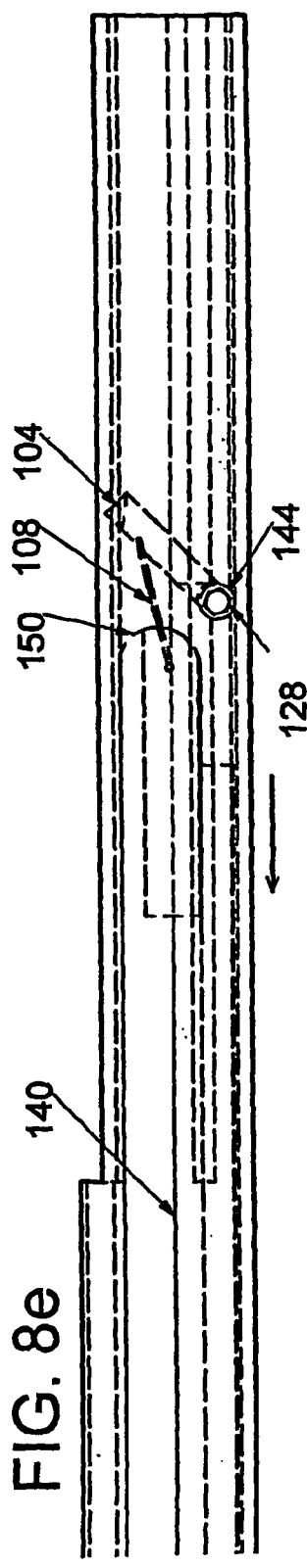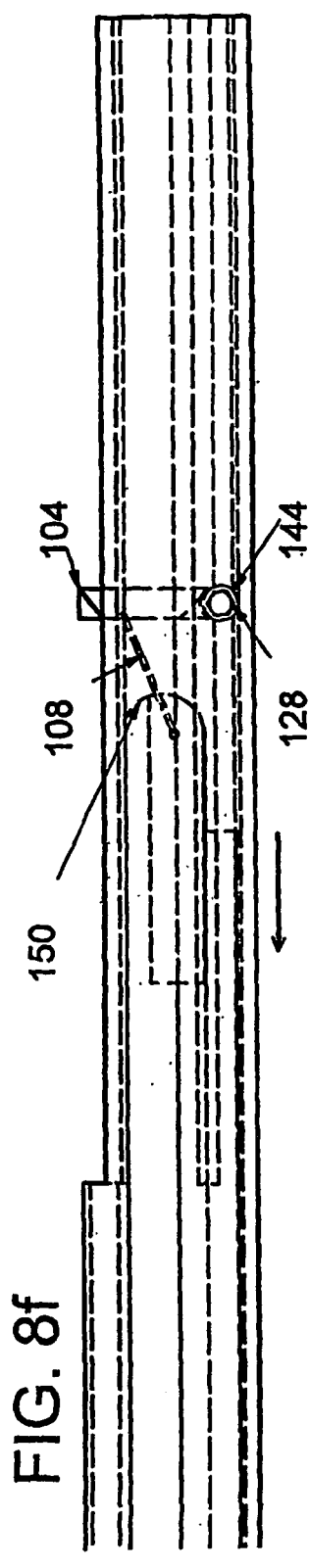

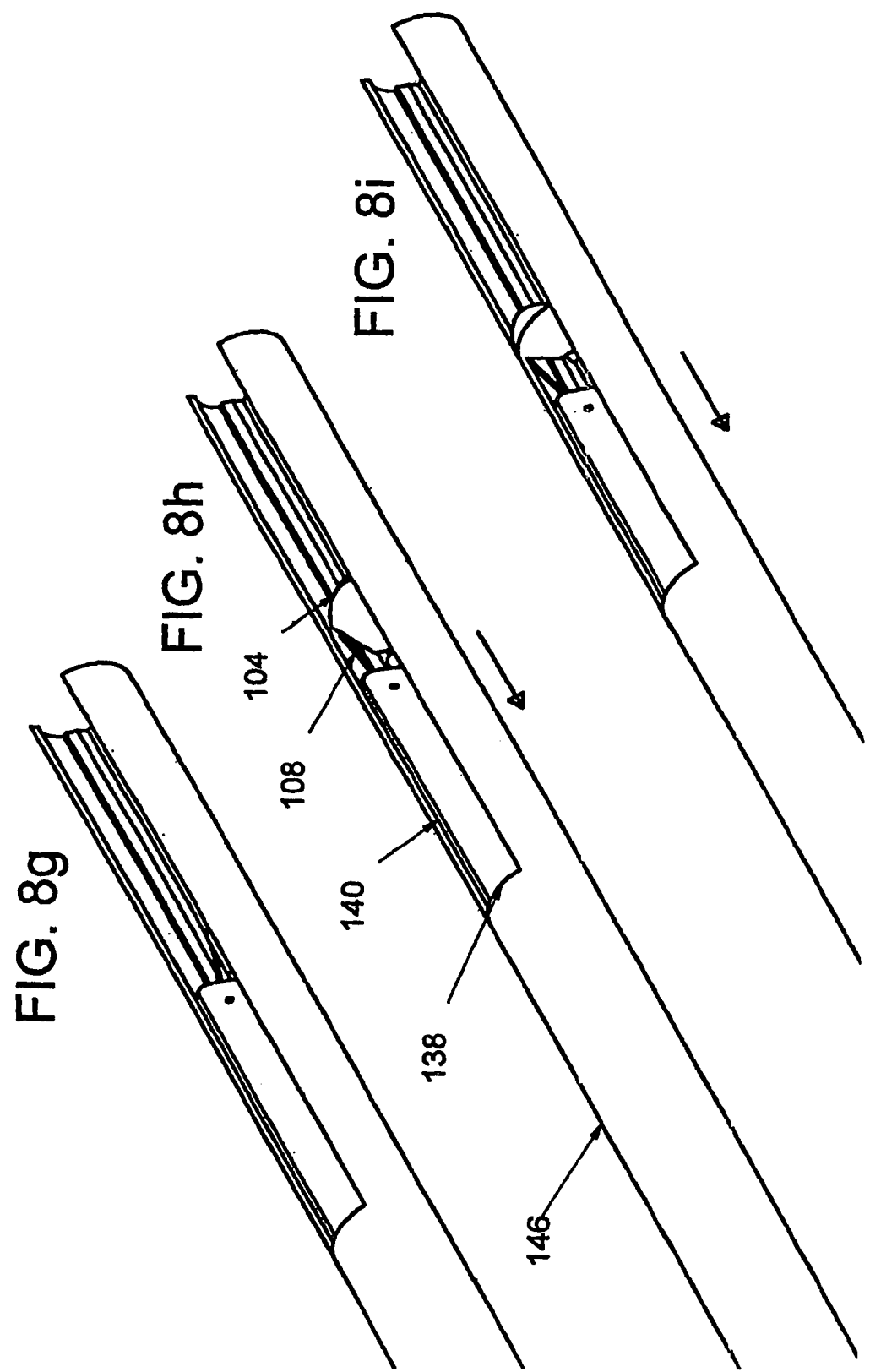

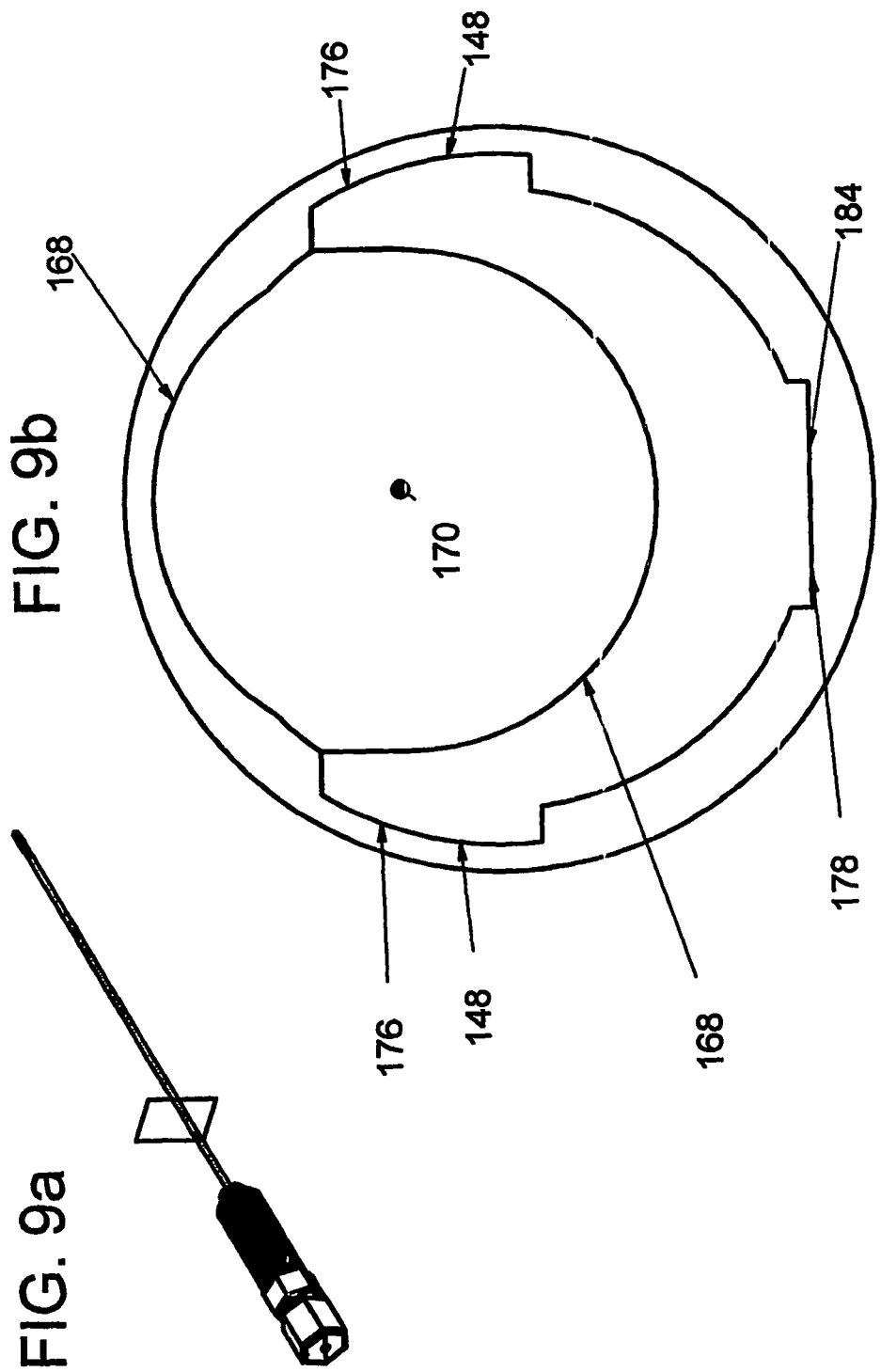

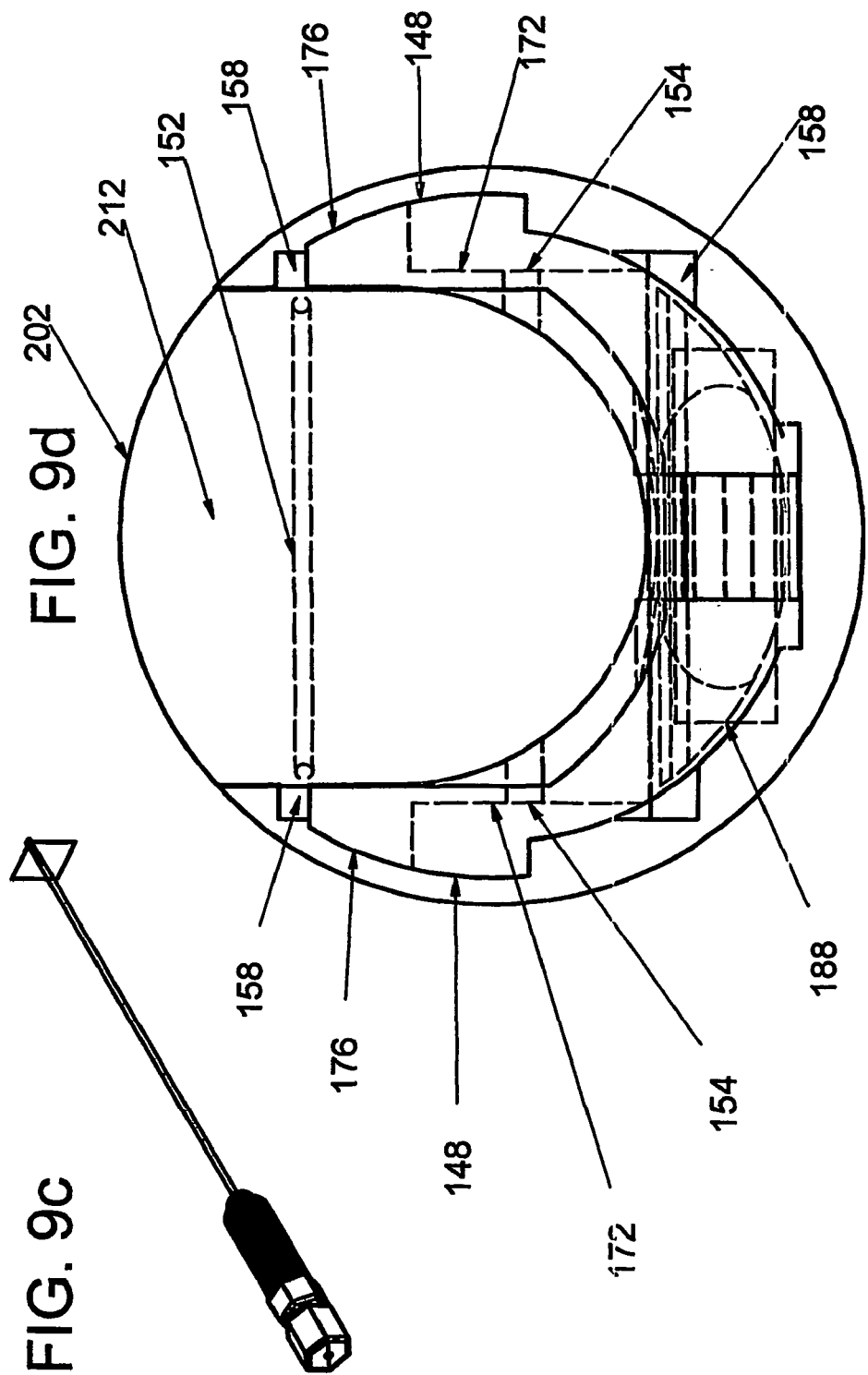

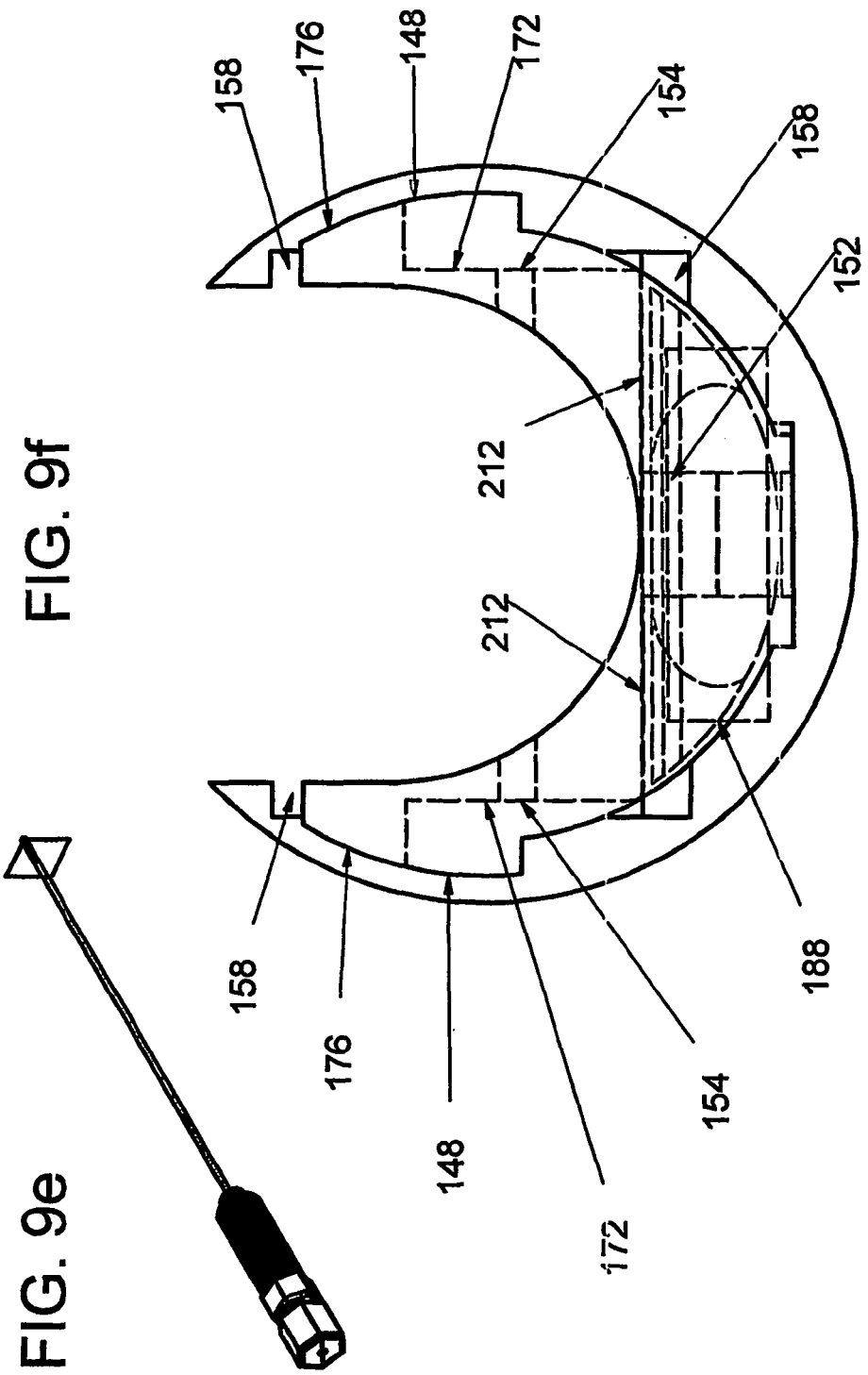

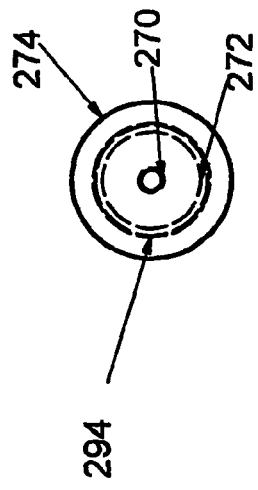
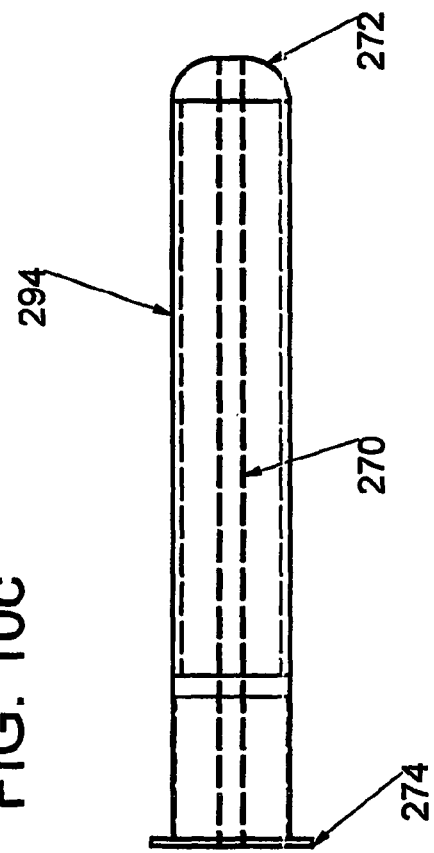
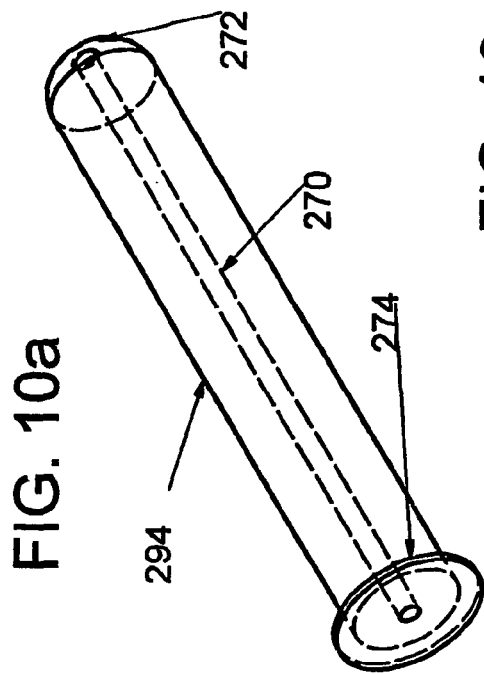

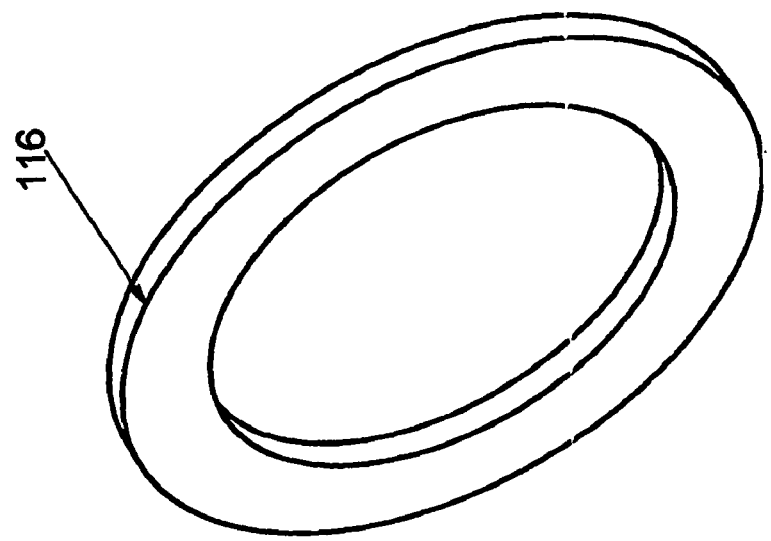
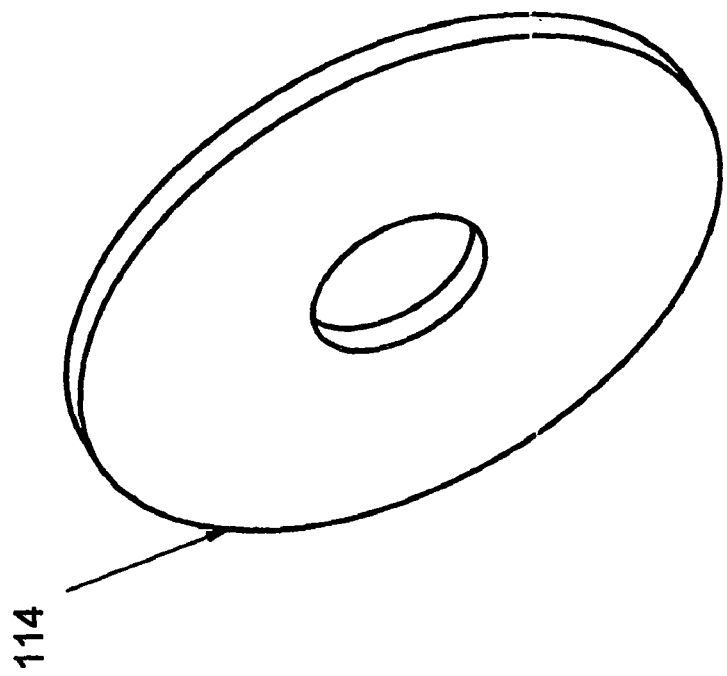

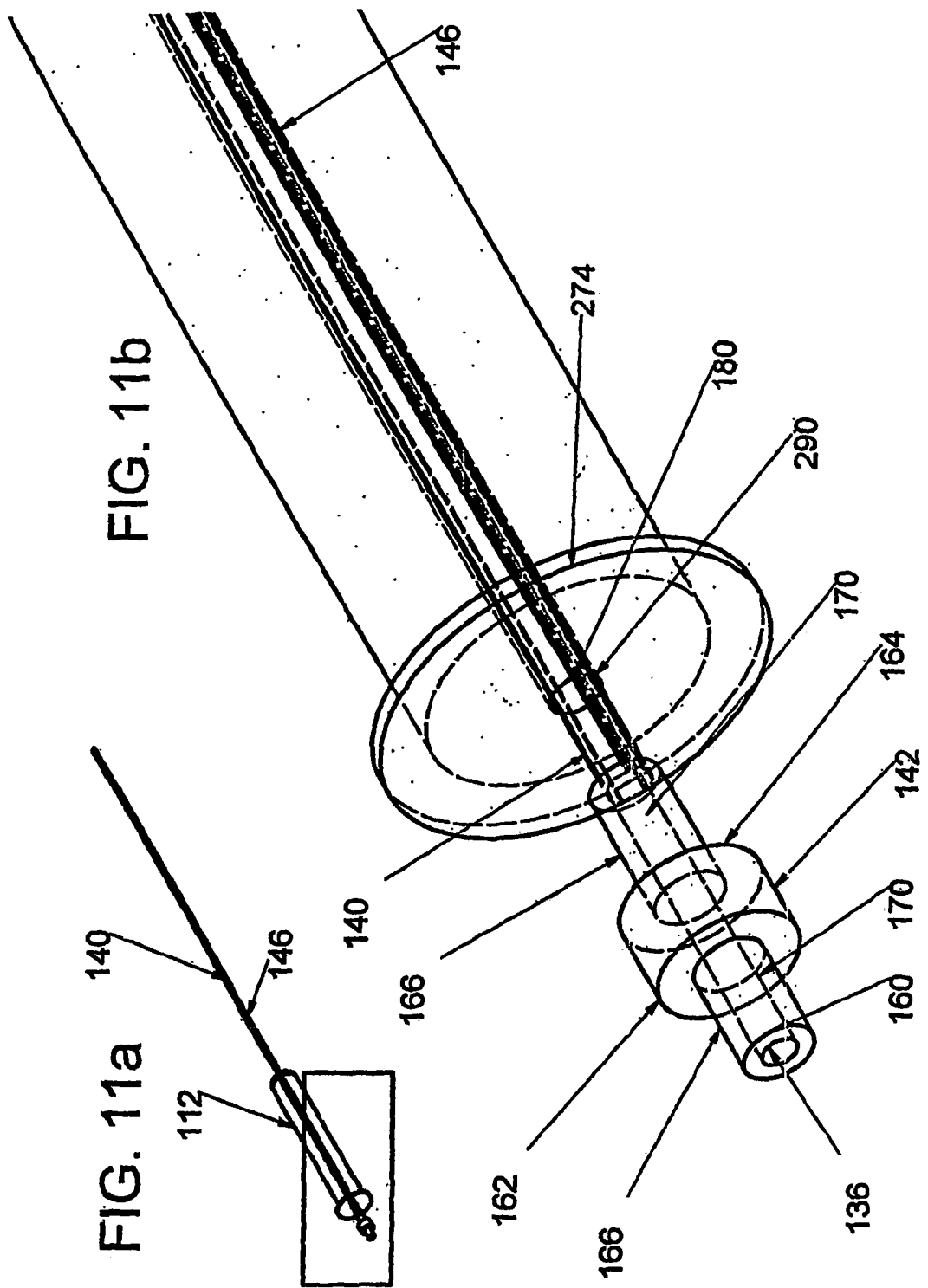

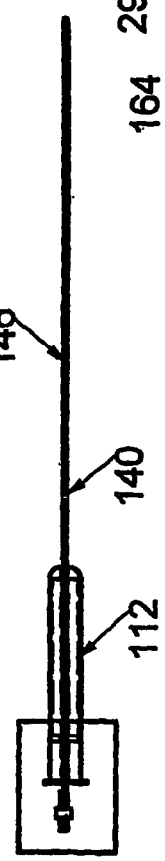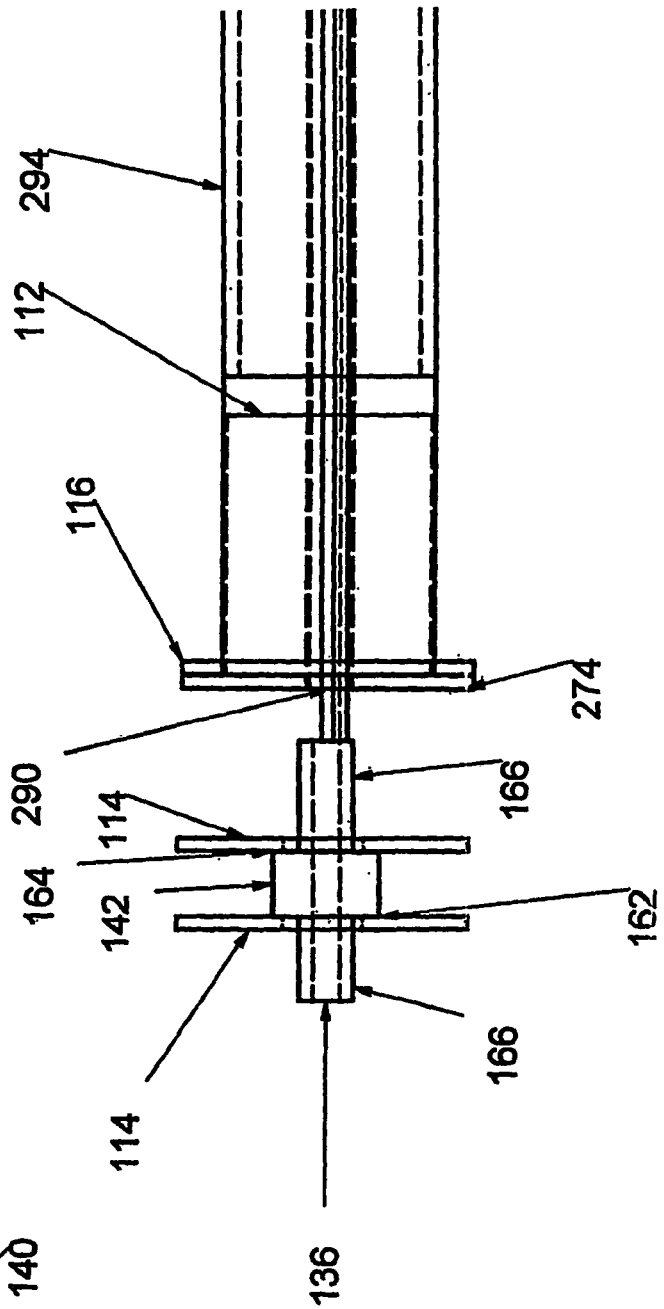

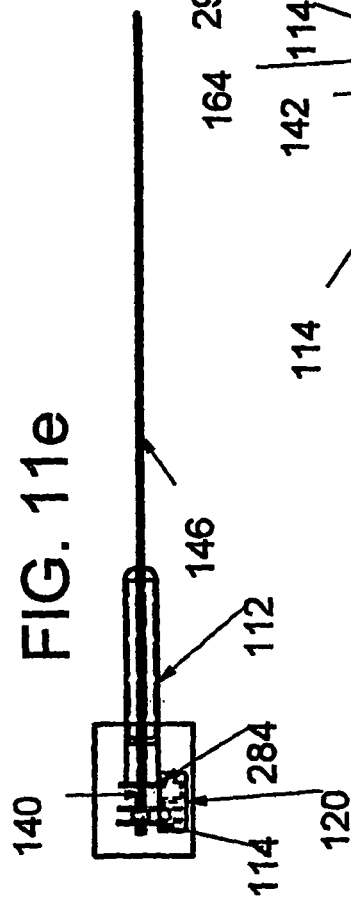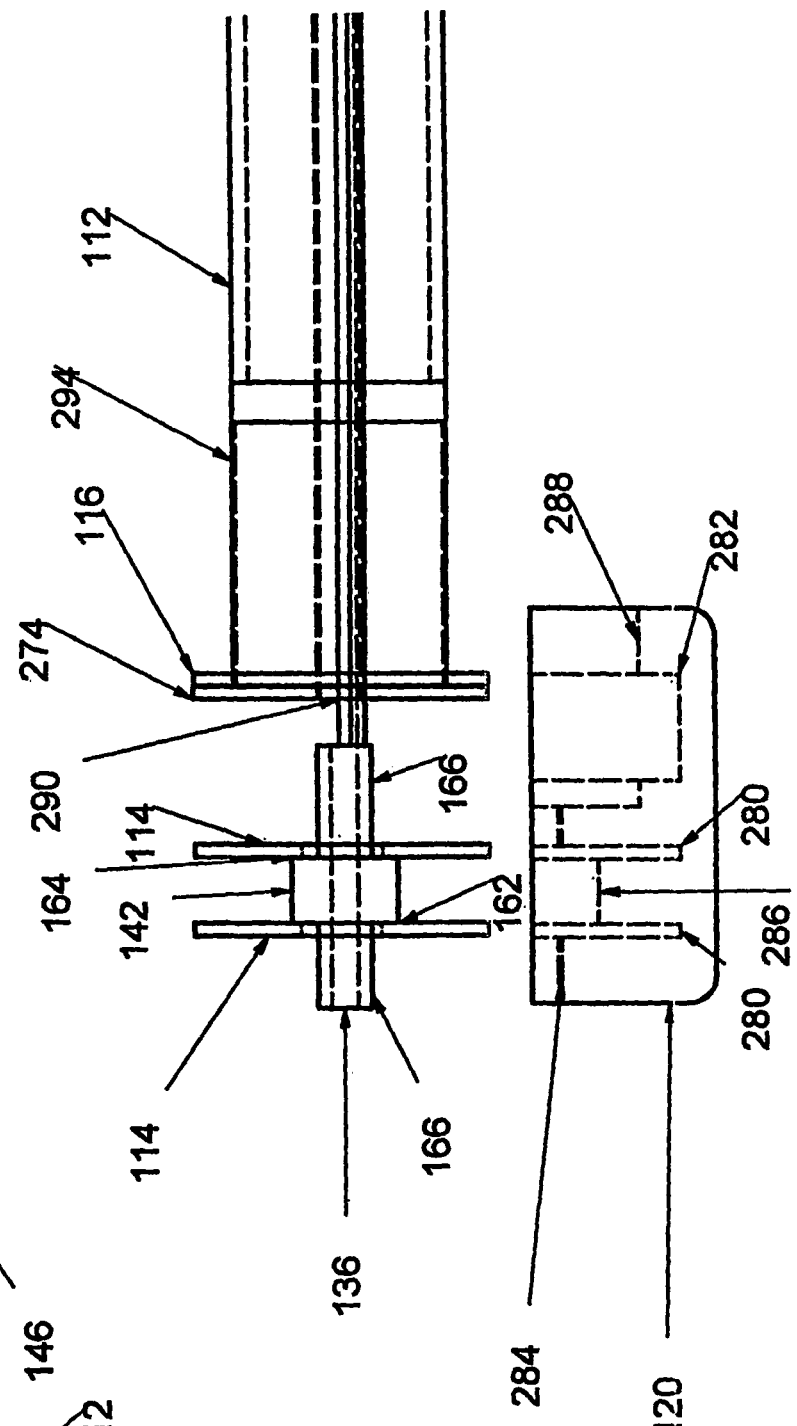

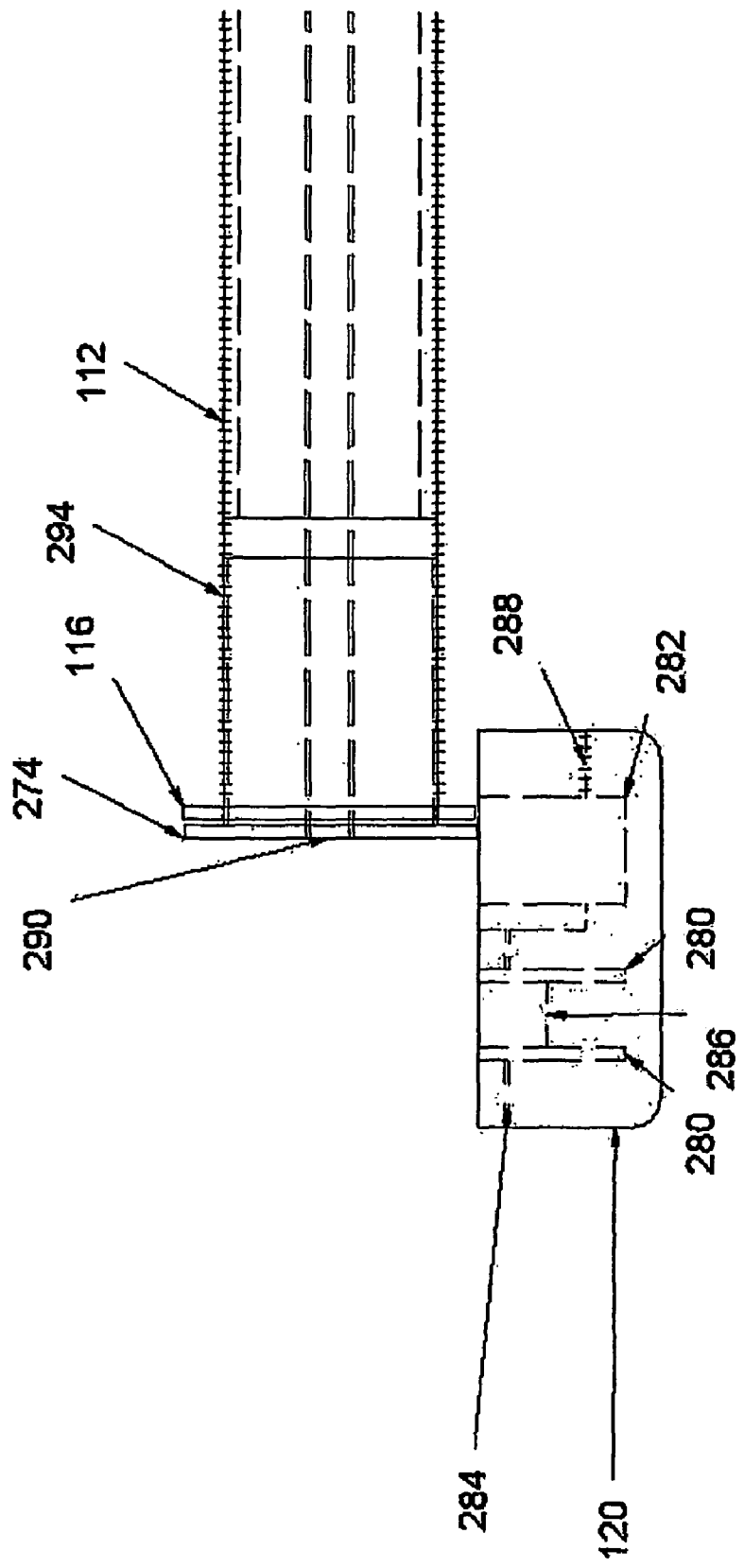

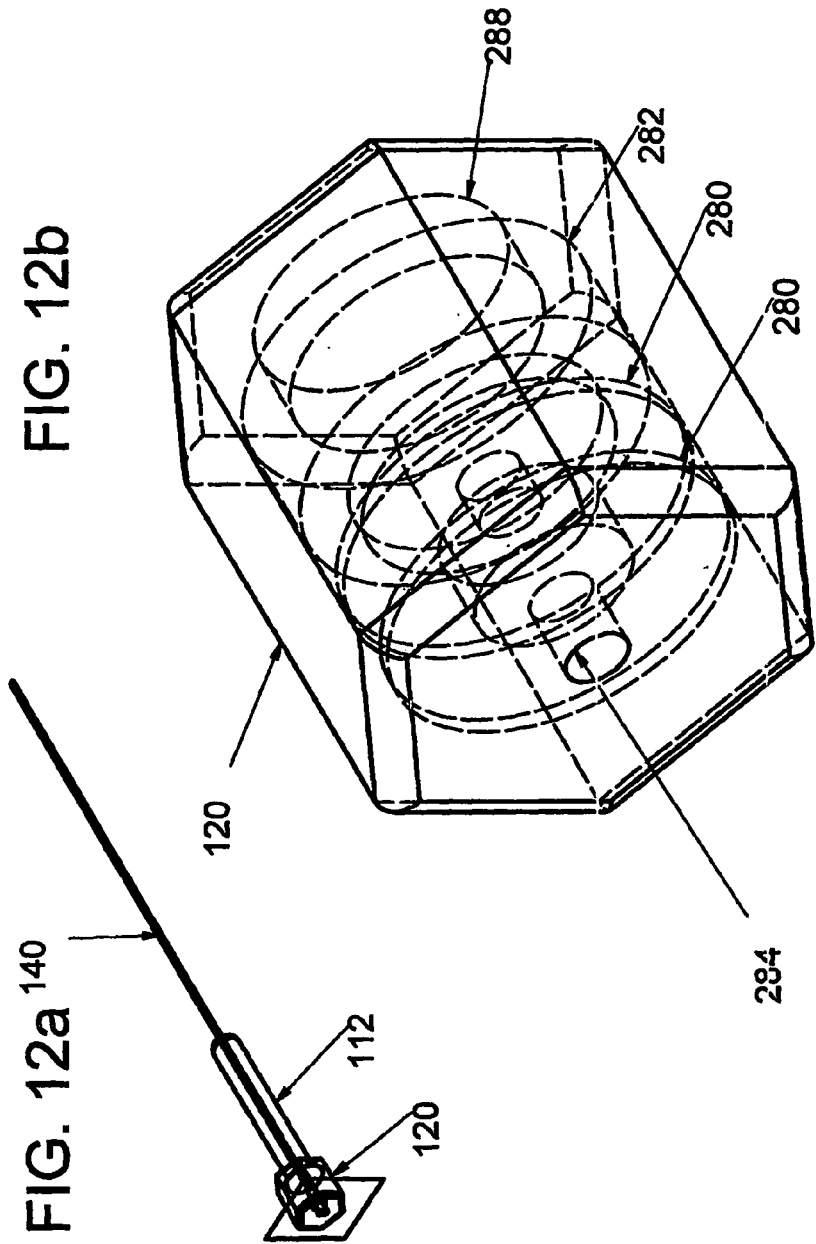

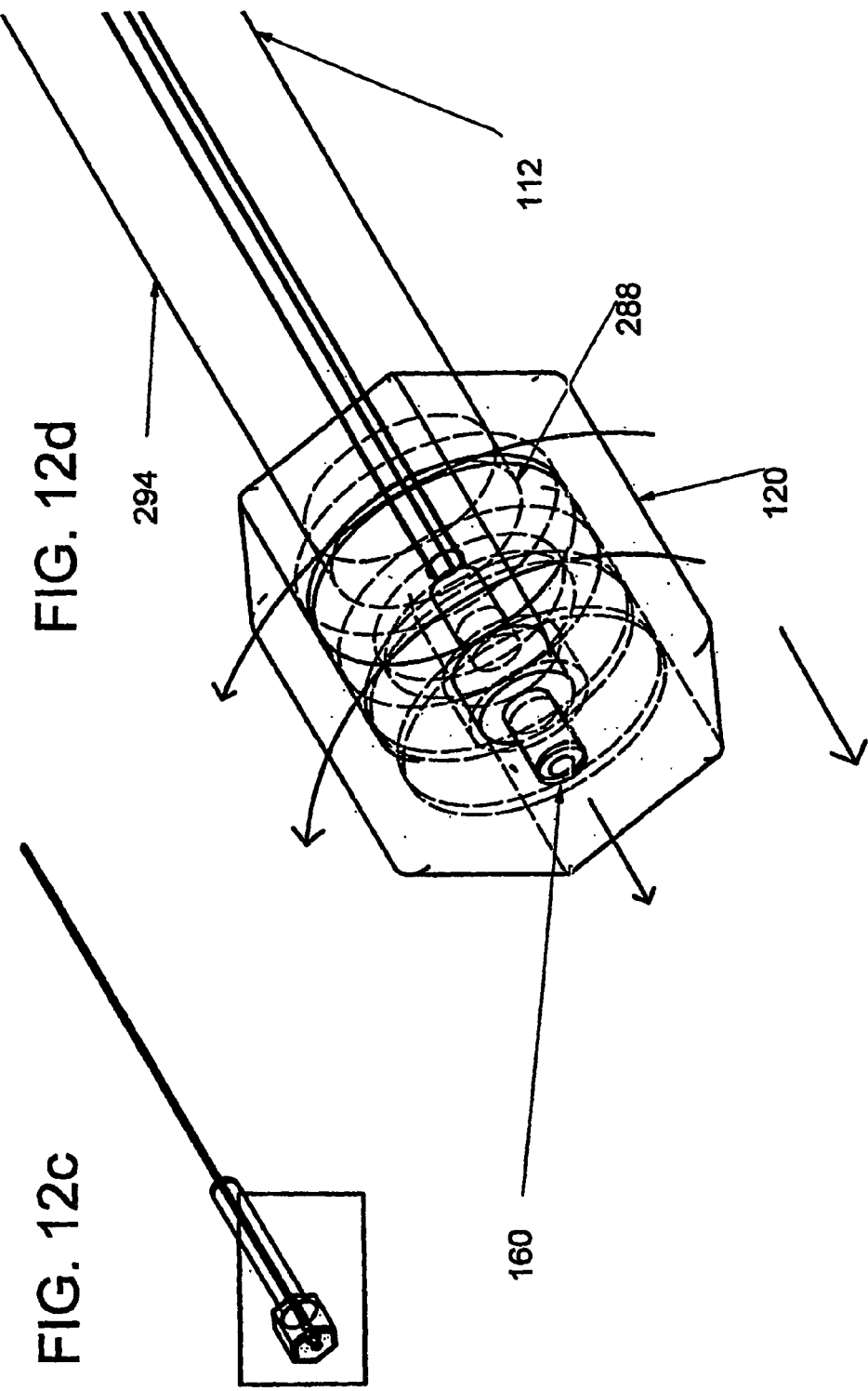

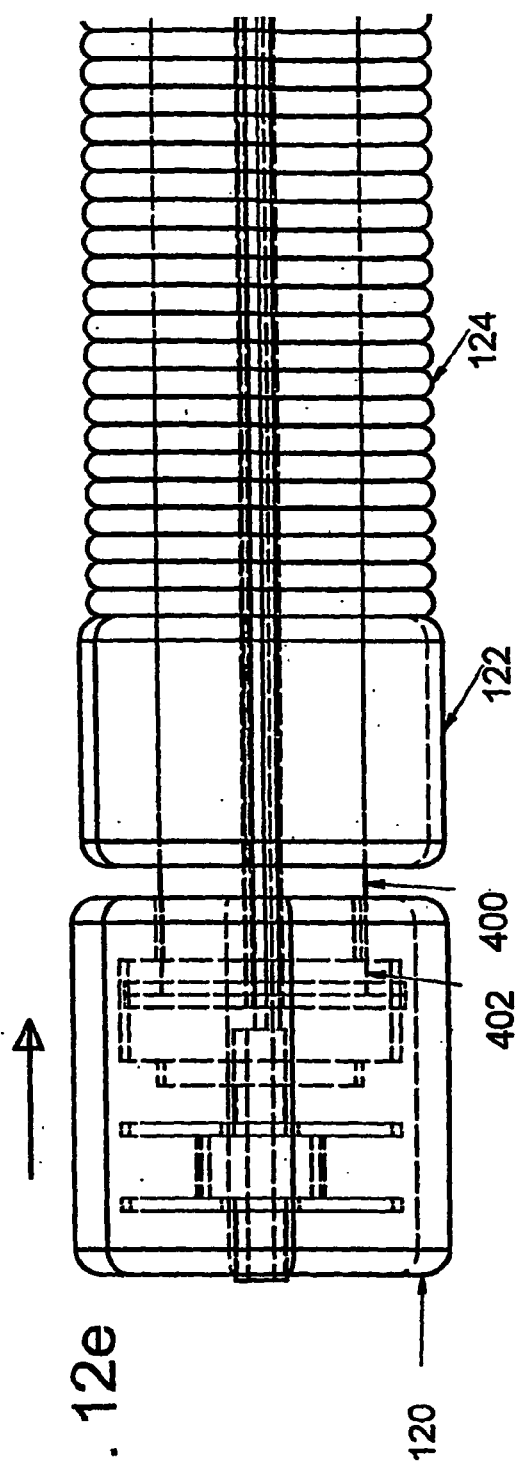
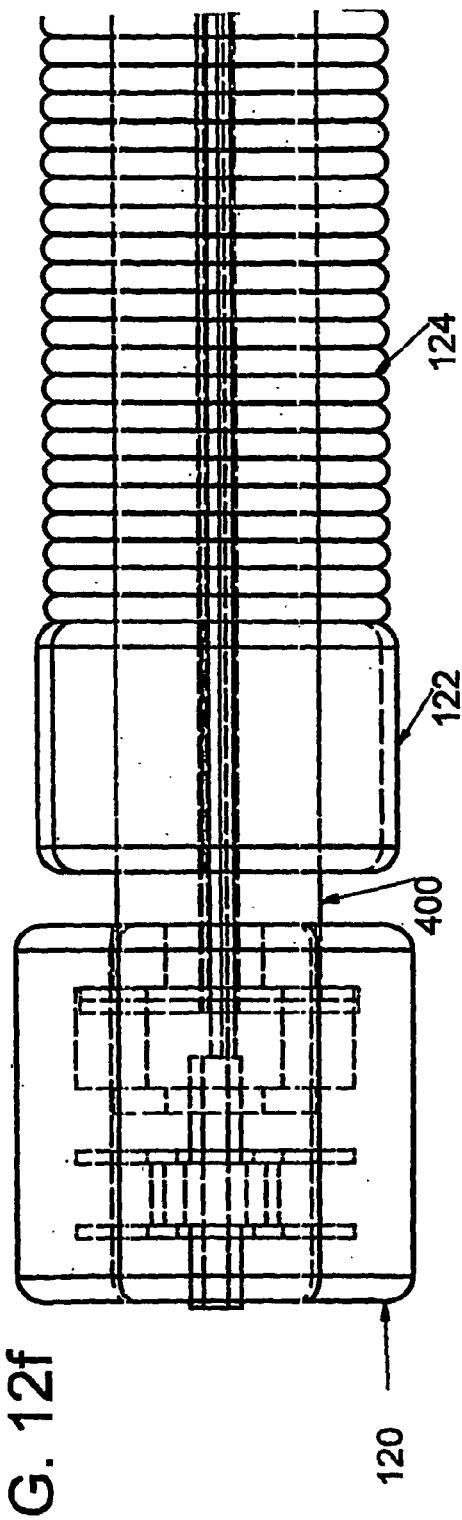
FIG. 12e
FIG. 12f

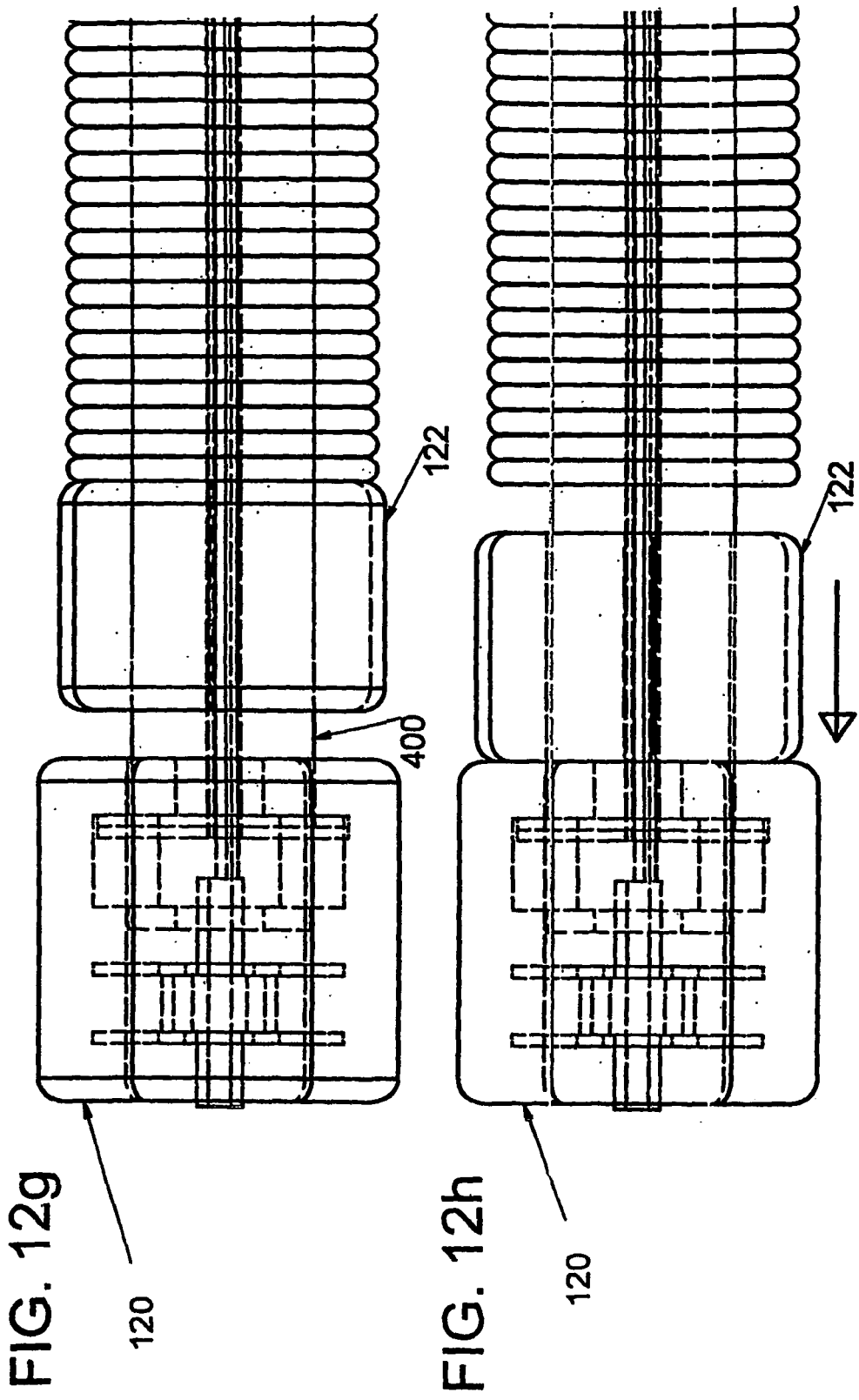

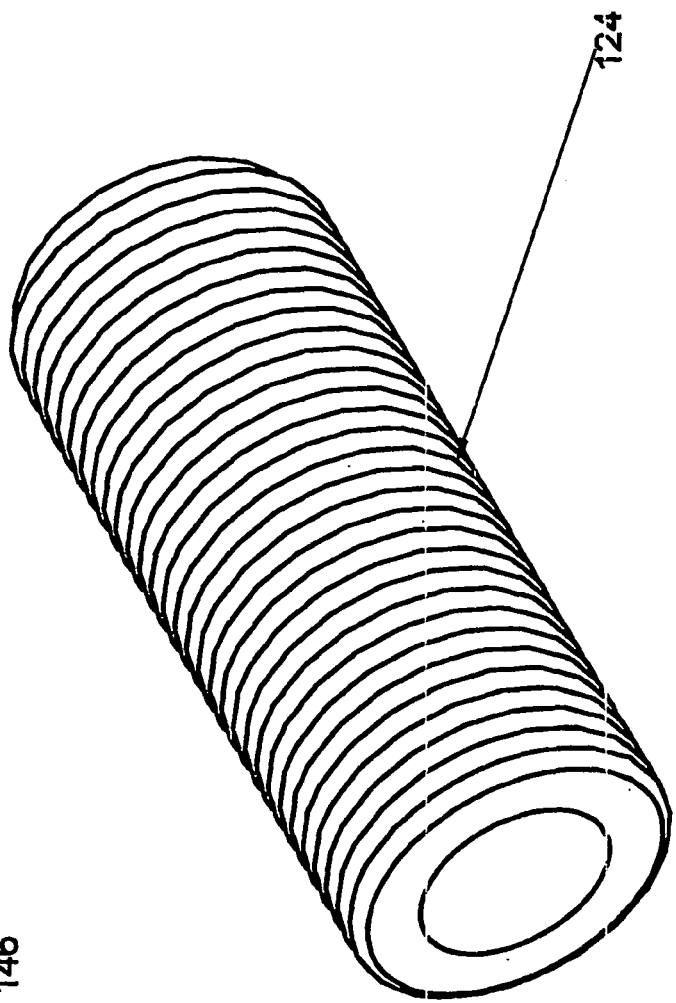
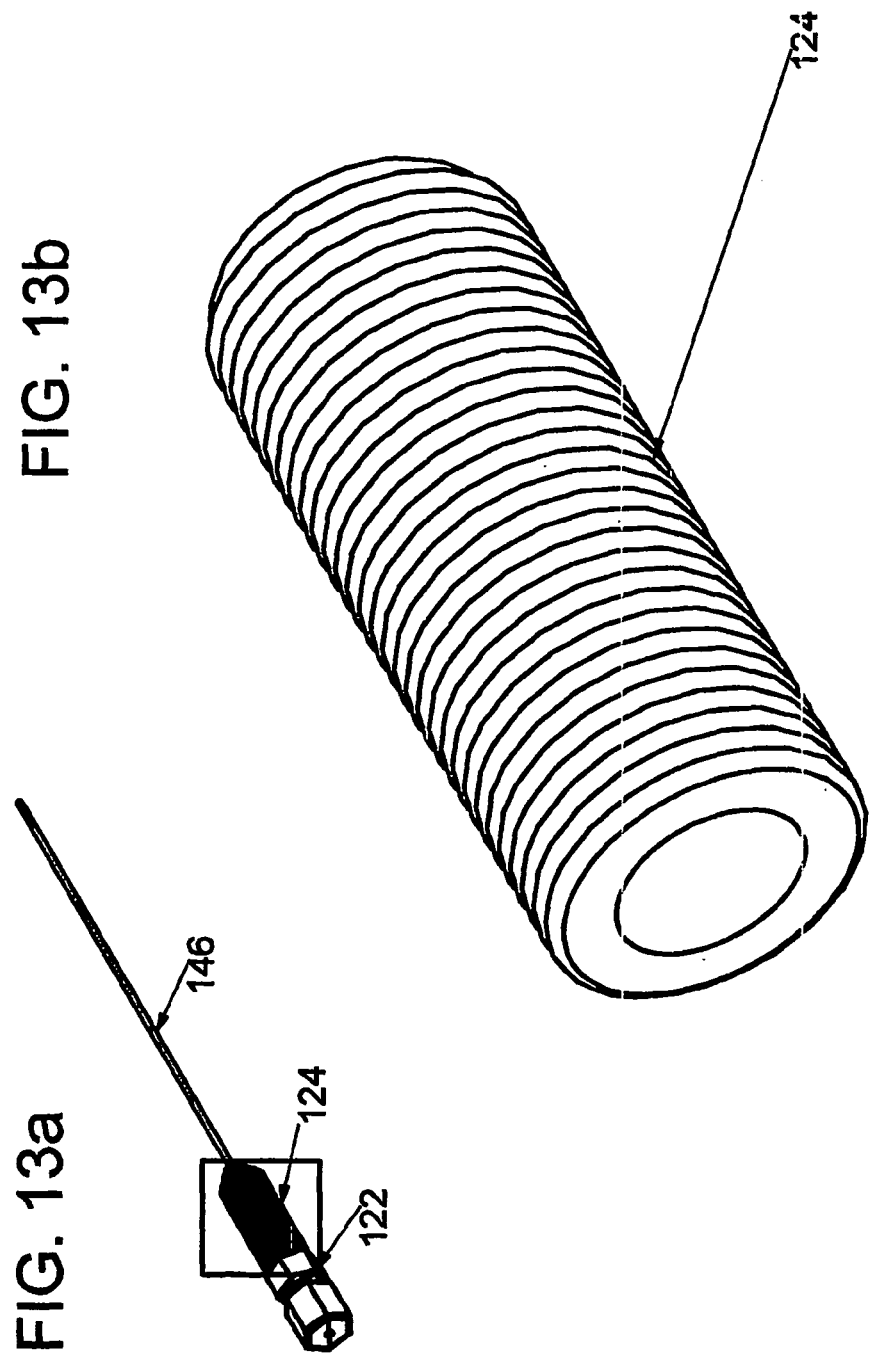
FIG. 13a
FIG. 13b

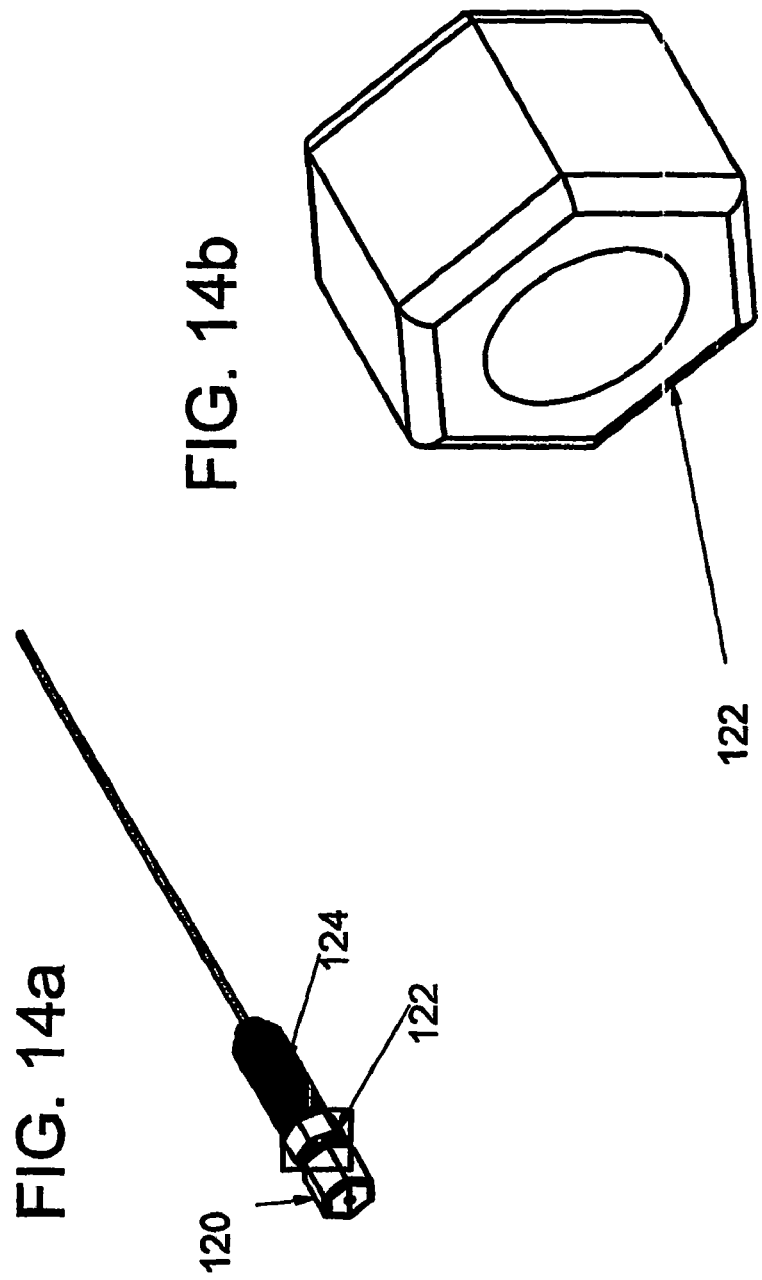

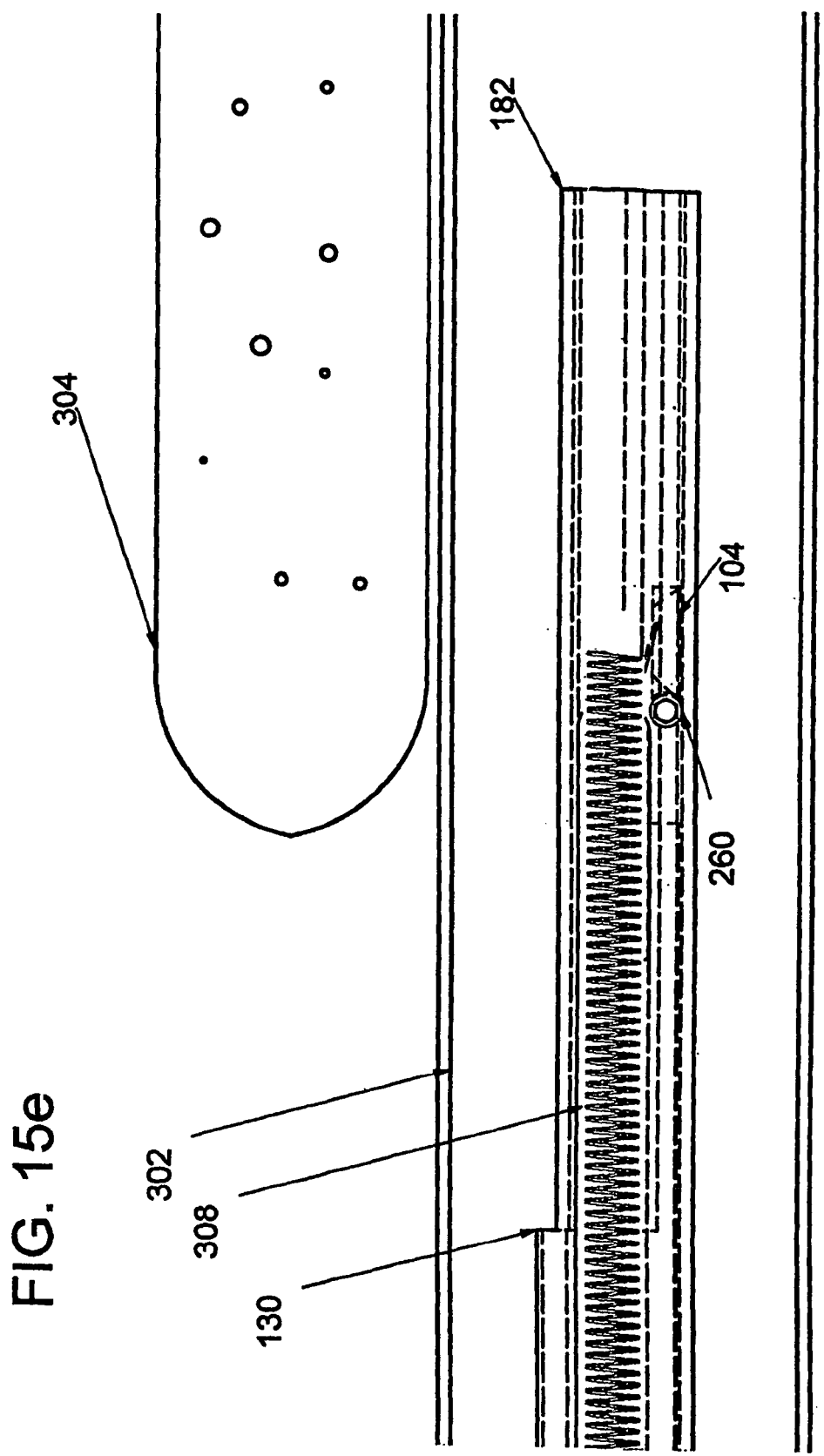

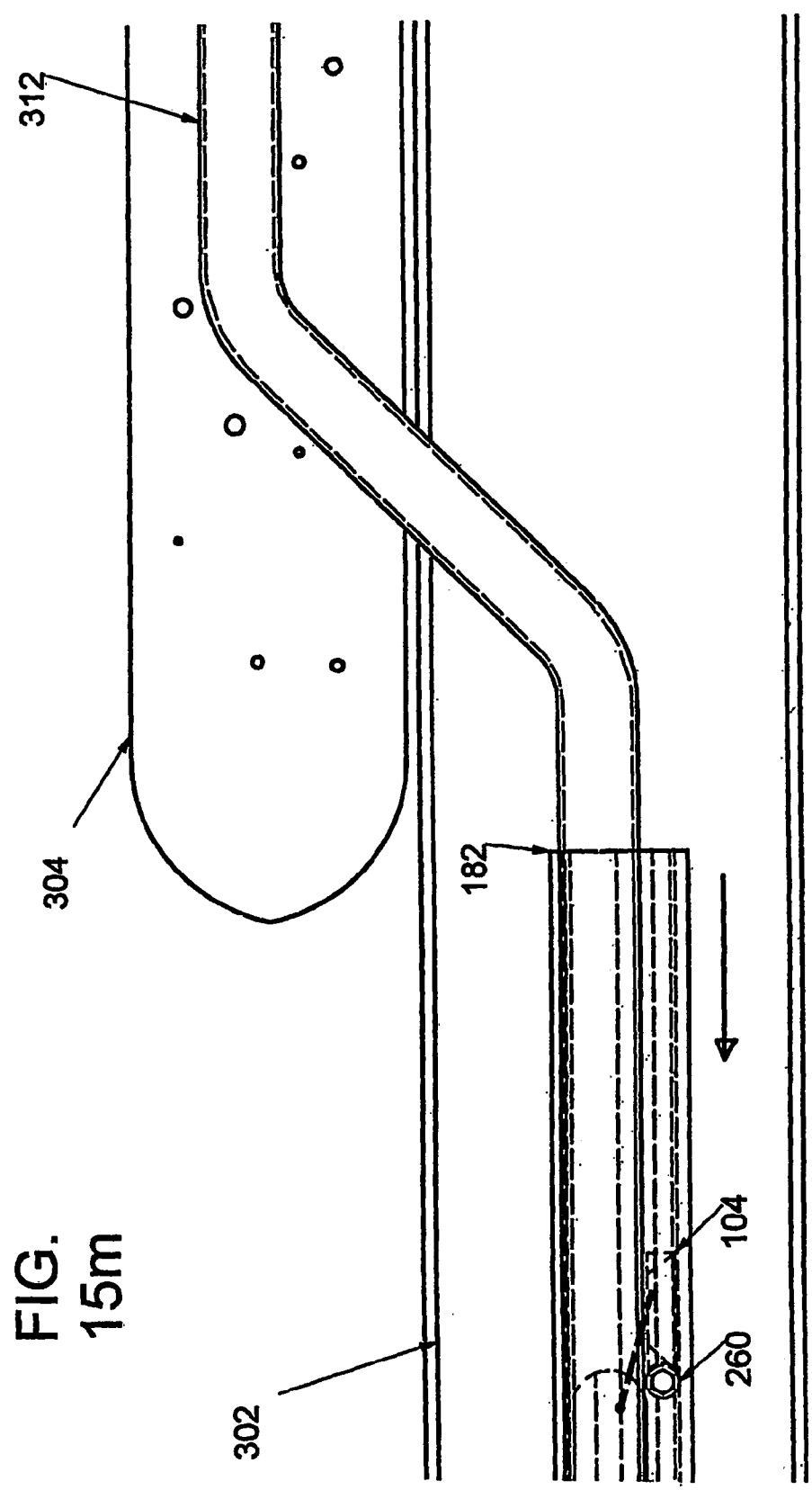

ADJUSTABLE DEVICE DELIVERY SYSTEM

This application is a U.S. national phase application pursuant to 35 U.S.C. §371 of International Application No. PCT/US04/15962, filed May 21, 2004, which claims priority to U.S. provisional patent application Ser. No. 60/472,875, filed May 23, 2003.

BACKGROUND OF THE INVENTION

1. Field of the Invention

The present invention relates to the delivery and useful placement of devices at angles other than that dictated by the tube geometry. This invention specifically relates to intervention into biological tubes as well as non-biological systems where placement of a device at an angle is needed in a confined working space.

2. Description of Related Art

The human body contains many tubes of varied sizes, for example, in the circulatory, digestive, reproductive, respiratory and urologic systems. Numerous devices have been developed to allow inspection and manipulation of these tubes and surrounding structures. Minimally invasive techniques use devices that are externally inserted and designed to travel within these tubes. In the vast spectrum of disease, there is often a need to direct, for example, a needle, guidewire, stent, drainage or visualization device at an angle that differs from the path of the tube through which the instrument is passed.

Previous descriptions of catheter delivery systems that direct wire-like devices at angles other than substantially parallel to the pathway of the tube through which the delivery system is traveling can be divided into either external steerable devices or internal deflection devices. External steerable devices generally consist of long tubes made of flexible materials with a distal end controlled by an internally placed control wire. Traction or tension on the wire causes a torque on the distal end of the steerable catheter, which causes the distal end to be projected at an angle different than the proximal end. Hence, the distal end is steered by torque forces formed by pulling on a control wire, and portions of the entire instrument bend toward the direction of these forces. Internal deflection devices are straight or slightly curved tubes that have a side port near the distal end that rely on a fixed internal collision with a fixed internal deflection device. As a wire device passes through the tube, it collides with the fixed internal deflection device and is deflected at a fixed angle out a side port.

Attempts have been made to create functional external steering catheters as described above. Examples of these devices are described in: U.S. Pat. Nos. 4,582,181, 4,998,917, 5,439,006, and 6,126,649. These devices share common weaknesses, the most obvious being that these instruments, when flexed, no longer maintain a low-profile. These devices would not be able to achieve an adequate degree of angulation inside of a delicate fixed space such as, for example, a blood vessel or other delicate biological or non-biological space without the danger of accidentally injuring or compromising the walls of the space.

As mentioned, these devices generally have a wire that is pulled, which flexes the delivery system and causes the distal port to project at an angle different than the proximal port. A problem arises with this kind of steerable catheter-type device when the distal tip of the device flexes at an angle because such movement can project the distal wall of the device outside the narrow passageway of the tube or space accommodating the delivery system. When the distal end of the steerable catheter is aligned with the proximal end, as it would be for insertion, the device can fit safely inside of a small lumen tube or space. However, as the distal end of the steerable catheter is torqued and consequently bent at an angle by the tensioning of a control wire or movement of a steering apparatus, such movement distorts the path and arc of the steerable catheter in such a way that it no longer fits inside of the small tube or space it was designed to manipulate or in which it was designed to operate. That is, as the distal tip or the steerable catheter is steered, the distal tip is no longer aligned with the proximal tip. Consequently, a vessel or space that could safely accommodate such an instrument would need to be at least as wide as the proximal port, where the instrument is actually inserted, and as wide as the distal tip when bent at the desired angle for delivery. As a steerable delivery system transforms from a linear tube to a bent tube, sheering forces can place the entire length of the biological tube or the non-biological space at a high risk of injury. The tip itself, when turned and projected outside the path of the remainder of the delivery system, would generate a high risk of focal perforation.

Attempts have been made to design internal deflecting cannulas. Generally these catheters have side guidewire exit ports located proximal to their distal tips. Examples of these devices are described in U.S. Pat. Nos. 4,405,314, 4,947,864, 5,183,470, 5,190,528, 5,413,581, 5,464,395 and 6,511,458. These designs also share common weaknesses. First, internal deflection devices are not adjustable, i.e., deflection can be achieved only at one angle. The lack of an adjustable internal deflection device disallows the use of a guidewire to be used down a straight pathway to place the device in the desired location. Efforts to overcome this weakness by having two separate lumens, one with an internal deflection device and the other with a straight lumen for placement of the catheter such as U.S. Pat. No. 5,655,548 are lacking, in part because the need to accommodate multiple lumens doubles the width of the delivery system. Such devices are also not adjustable. Moreover, the narrow spaces in which such systems are used limits the angle at which a wire or catheter can be deflected.

Another major weakness shared by both external steerable and internal deflecting delivery systems is that while deploying a device such as, for example, a stent at an angle is possible, removing the external steerable or internal deflecting delivery system with the stent in proper position is exceedingly difficult and impossible at angles approaching right-angles to the device passageway. Such problems obviate any practical use of these devices as means of deploying devices, such as, for example, stents and drainage catheters, at lasting angles. Attempts to remove the external steerable or internal deflecting delivery system in a linear path, cause collisions between the distal end of delivery system and the delivered device, when placed at an angle that differs from the linear path of delivery system removal.

The collision problems that arise with removal of external steerable delivery systems lie in the fact that once a device, such as a stent or wire, has been placed, the delivery system must conform to the shape of the lumen or space in order to be removed from the lumen or space. That is, as the device is withdrawn along the path of the lumen, the external shape of the delivery device must conform to the lumen or space geometry. Any effort to remove the catheter delivery system in its "bent," or device delivery, form would cause the distal end, i.e. the end with the deployed device, to deform to the shape of the lumen geometry. Thus any attempts to remove the delivery system with a device, such as a stent or guide-wire, placed at an angle would cause dislodgement of the device as the axis of the forces necessary to remove the delivery system differ from the angle of device placement.

Multiple problems arise with removal of internal deflection delivery devices as well. An obvious problem is seen in U.S. Pat. No. 6,514,217, which relates to an internal deflection device that relies on a flapper assembly to direct a catheter. This assembly uses an internal deflection device just distal to the external slot. Because the internal deflection of the delivered device must be fixed in a location for a flapper device to function, if the operator attempts to remove the internal deflection delivery system from the body by pulling proximally along the length of the tube, the internal deflection device would collide with the wire or stent, which is projected at an angle different from that of the tube. Consequently, as the delivery system is withdrawn from the body by pulling proximally along the length of the tube, the wire or stent at an angle different from that of the tube would also be pulled along the angle of the tube. This pulling force would tear and disrupt the surrounding tissues and ultimately the wire or stent would be pulled out of the body along with the delivery system causing great damage.

Thus, external steerable or internal deflection delivery devices have many limitations inherent in their design leaving a need for a device that can fully function in a narrow biological or non-biological space, deploy a variety of separate and lasting devices such as, for example, stents, drainage catheters and visualization devices, at accurate angles and control these angles of deployment in a user-definable manner. These devices also leave the need for an adjustable device delivery system that can be withdrawn from the delivery area after the placement of one or more devices at a user-defined angle without disruption of these devices from their desired location.

SUMMARY OF THE INVENTION

The present invention provides an adjustable device delivery system capable of deploying various medical and non-medical devices to biological and non-biological systems at angles different than the angle of the lumen or space within which the present invention is passed. The delivery angle of the devices provided by this invention is also preferably different from the angle of the body of the device delivery system. The device delivery systems of the invention also permit a delivered device to retain its angle of delivery despite removal of the device delivery system. The present invention further provides methods of utilizing the adjustable device delivery systems of the invention.

In a first aspect, the invention provides an adjustable device delivery system comprising an optionally flexible tubular body having a proximal end, a distal end, a longitudinal axis, a lumen extending within the tubular body, and a slot within the tubular body extending to and including its distal end; and an adjustable internal door comprising a door body with a superior, inferior, proximal, distal and two side surfaces, one or more door hinge holes in the side surfaces of the door body and a door hinge surface on the inferior surface of the door body, the adjustable internal door hingedly coupled to the interior of the tubular body, located opposite the slot in the distal portion of the tubular body. In the adjustable device delivery system of this first aspect, at least one device can be slidably connected within the lumen of the optionally flexible tubular body, wherein the at least one device is deflected off of the proximal surface of the adjustable internal door at a user-definable angle and delivered to a target site at the user-definable angle. That is, one or more medical devices, non-medical devices or electromagnetic radiation (EMR) emitting and/or receiving devices can be slidably inserted into, and therefore connected to, the lumen of the adjustable device delivery system of the invention. Once slidably connected, the at least one device can be slidably moved within the lumen in a distal direction until the at least one device collides with and is deflected off of (or emits radiation that collides with and is deflected off of) the proximal surface of the adjustable internal door set at a user-definable angle.

In a second aspect, the optionally flexible tubular body of the first aspect can comprise an outer cannula and an inner drive cannula, wherein the inner drive cannula is slidably connected to the inside of the outer cannula, optionally on a track system. The distal end of the outer cannula can be open, and the distal end of the outer cannula can contain a slot extending to and including its distal end. The slot can comprise less than 50 percent of the circumference of the outer cannula or more than 50 percent of the circumference of the outer cannula. Preferably, the slot comprises about 50 percent of the circumference of the outer cannula. Further, the slot can extend more than 3 door-lengths from the distal end of the outer cannula or less than 3 door-lengths from the distal end of the outer cannula as well as about 3 door lengths from the distal end of the outer cannula. The distal portion of the inner drive cannula can comprise an open shaft, which open shaft can approximate the lower portion of a half cylinder.

In a third aspect, the proximal portion of the inner drive cannula of the adjustable device delivery system further comprises a drive actuator to facilitate movement of the inner drive cannula along the proximal-distal, or longitudinal, axis. The drive actuator can further comprise a drive barrel with a first diameter (the drive barrel diameter) at the proximal end of the inner drive cannula and a drive shaft with a second diameter (the drive shaft diameter), different than the first diameter of the drive barrel, located within the axial length of the drive barrel. Where the drive barrel, with its first diameter, and the drive shaft, with its second diameter meet, one or more drive barrel-drive shaft interfaces, or edges, are created, such that edges defined at the one or more drive barrel-drive shaft interfaces provide a leverage means to move the inner drive cannula along the proximal-distal axis. In such embodiments, the drive actuator can comprise a drive barrel of a smaller diameter than the drive shaft or a drive barrel of a larger diameter than the drive shaft.

The drive actuator of the adjustable device delivery system of this aspect can further comprise one or more washers wherein the diameter of the hole in the washer (the washer inner-hole diameter) is larger than the smaller of the drive barrel diameter or drive shaft diameter but smaller than the larger of the drive barrel diameter or drive shaft diameter, wherein the one or more washers can reside on the smaller diameter drive barrel or drive shaft and press against the larger diameter drive barrel or drive shaft to move the inner drive cannula along the proximal-distal axis. In a related manner, the drive actuator of the adjustable device delivery system of this aspect can comprise one or more washers wherein the washer inner-hole diameter is larger than the drive barrel diameter but smaller than the drive shaft diameter, wherein the one or more washers can reside on the drive barrel and press against the drive shaft to move the inner drive cannula along the proximal-distal axis. Similarly, the drive actuator of the adjustable device delivery system of this aspect can comprise one or more washers wherein the washer inner-hole diameter is larger than the drive shaft diameter but smaller than the drive barrel diameter, wherein the one or more washers can reside on the drive shaft and press against the drive barrel to move the inner drive cannula along the proximal-distal axis. In the above embodiments, the drive barrel and drive shaft can be cylindrical.

In a fourth aspect, the outer cannula of the adjustable device delivery system of the second and third aspects contains an axle shell toward, at or in its distal end, which axle shell can be located opposite the slot in the outer cannula. The axle shell can hold on its inner surfaces an axle comprising a middle portion and two cylindrical side portions, wherein the outer diameter of the cylindrical side portions of the axle corresponds to the inner diameter of the axle shell, and the size and geometric shape of the middle portion of the axle is the same as or different from the cylindrical side portions of the axle. In these aspects, the door hinge surface of the adjustable internal door can be hingedly coupled to the middle portion of the axle wherein the size and geometric shape of the middle portion of the axle corresponds to the geometric size and shape of the inner surface of the door hinge surface.

In a fifth aspect, the adjustable device delivery system of the second through fourth aspects can further comprise a door connector system, comprising one or more door connectors, moveably connecting the distal end of the inner drive cannula at one or more hinge holes to the door hinge holes in the side surfaces of the door body of the adjustable internal door. The one or more door connectors comprise a shaft with a proximal and a distal end, the proximal end comprising a proximal inner drive cannula insertion tab, which is moveably connected to the hinge hole in the distal end of the inner drive cannula and the distal end comprising a distal door insertion tab, which is moveably connected to the door hinge hole in the side surface of the door body. In these aspects, proximal movement of the inner drive cannula pulls on the door connectors at the proximal inner drive cannula insertion tab and translates the proximal movement up the shaft to the distal door insertion tab and thence to the door hinge holes on the side surface of the adjustable internal door to the door body itself, which hingedly moves on the axle, increasing the angle of the adjustable internal door within the distal end of the outer cannula. Further, distal movement of the inner drive cannula pushes on the door connectors at the proximal inner drive cannula insertion tab and translates the proximal movement up the shaft to the distal door insertion tab and thence to the door hinge holes on the side surface of the adjustable internal door to the door itself, which hingedly moves on the axle, decreasing the angle of the adjustable internal door within the distal end of the outer cannula. To facilitate free movement of the adjustable internal door and one or more door connectors of the above aspects, the distal portions of the outer cannula and the inner drive cannula can be shaped to allow such free movement.

In a sixth aspect, the inner drive cannula of the adjustable device delivery system of the above aspects is slidably connected to the inside of the outer cannula on a track system, which can comprise an outer cannula that contains one or more guide tracks and an inner drive cannula that contains one or more corresponding tracks upon which the inner drive cannula slidably moves on the proximal-distal axis. Likewise, the track system can comprise an outer cannula that contains one or more side guide tracks and/or one or more bottom guide tracks and an inner drive cannula that contains one or more corresponding side tracks and/or one or more corresponding bottom tracks upon which the inner drive cannula slidably moves on the proximal-distal axis.

In a seventh aspect, the proximal portion of the outer cannula of the above aspects can be threaded to facilitate the rotatable attachment of one or more correspondingly threaded attachments. Further, the proximal end of the outer cannula can include a raised ridge of a larger diameter than the proximal end of the outer cannula.

In an eighth aspect, an attachment of the seventh aspect can comprise a steering assembly comprising a center shaft, two or more cylindrical cutout areas wherein the outer diameter of the drive actuator drive barrel fits into the inner diameter of the steering assembly center shaft, which shaft is cut out and extends the proximal-distal length of the steering assembly, a cylindrical cutout area in the distal end of the steering assembly of an inner diameter corresponding to the outer diameter of the proximal portion of the threaded outer cannula, the cylindrical cutout correspondingly threaded to rotatably attach to the proximal end of the outer cannula enabling proximal-distal movement of the steering system, a cylindrical cutout area of an inner diameter corresponding to the outer diameter of the drive actuator drive shaft and a proximal-distal length wherein the cylindrical cutout can fit over a drive actuator drive shaft of larger diameter than the drive actuator drive barrel or within a detent created when the drive actuator drive shaft diameter is smaller than the drive actuator drive barrel, and wherein the surfaces of the steering assembly correspond to the surfaces of the drive actuator and the outer cannula, whereby the steering assembly can freely rotate around the longitudinal axes of the drive actuator and the rotational motion of the steering assembly translates into proximal and distal translation of the steering assembly in relation to the outer cannula.

These aspects can further comprise one or more cylindrical slots of corresponding diameter and proximal-distal position within the steering assembly to interact with one or more washers present at the proximal end of the outer cannula and at the diametrically differing interfaces between the drive barrel and drive shaft.

In a ninth aspect, the adjustable device delivery system of the above aspects can further comprise a lock system comprising an inner surface and an outer surface, the inner surface of a diameter corresponding to the outer diameter of the proximal end of the outer cannula and threaded to facilitate its rotatable attachment to the correspondingly threaded proximal end of the outer cannula. The lock system can lock the position of the steering assembly, drive actuator, inner drive cannula and adjustable internal door by rotatably butting against the steering assembly on the threads of the outer cannula preventing the movement of the steering assembly, drive actuator, inner drive cannula and adjustable internal door. Likewise, the lock system can unlock the position of the steering assembly, drive actuator, inner drive cannula and adjustable internal door by rotatably moving away from the steering assembly on the threads of the outer cannula enabling the movement of the steering assembly, drive actuator, inner drive cannula and adjustable internal door.

In a tenth aspect, the adjustable device delivery system of the above aspects can further comprise an outer cannula cover, which outer cannula cover contain an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover can serve as a handle for operation of the adjustable delivery system. In these aspects, the proximal portion of the interior tract of the outer cannula cover can be threaded to rotatably attach to an outer cannula that is correspondingly threaded at its proximal end. Likewise, the outer cannula cover can be bonded with, for example, an adhesive, to the proximal end of the outer cannula, the outer cannula residing within the interior tract of the outer cannula cover.

In an eleventh aspect, the exterior of the proximal portion of the outer cannula cover of the tenth aspect can be threaded to facilitate the rotatable attachment of correspondingly threaded attachments. The proximal end of the outer cannula of these aspects can include a raised ridge of a larger diameter than the proximal end of the outer cannula. Likewise, the raised ridge can be of a diameter equivalent to or larger than the proximal end of the outer cannula cover. The raised ridge can act as a physical stop for the steering assembly described in earlier aspects.

In a twelfth aspect, the attachment of the eleventh aspect can be a steering assembly comprising a center shaft, two or more cylindrical cutout areas wherein the outer diameter of the drive actuator drive barrel fits into the inner diameter of the steering assembly center shaft, which shaft is cut out and extends the proximal-distal length of the steering assembly, a cylindrical cutout area in the distal end of the steering assembly of an inner diameter corresponding to the outer diameter of the proximal portion of the threaded outer cannula cover, the cylindrical cutout correspondingly threaded to rotatably attach to the proximal end of the outer cannula cover enabling proximal-distal movement of the steering system, a cylindrical cutout area of an inner diameter corresponding to the outer diameter of the drive actuator drive shaft and a proximal-distal length such that the cylindrical cutout can fit over a drive actuator drive shaft of larger diameter than the drive actuator drive barrel or within a detent created when the drive actuator drive shaft diameter is smaller than the drive actuator drive barrel, wherein the surfaces of the steering assembly correspond to the surfaces of the drive actuator and the outer cannula cover, the steering assembly can freely rotate around the longitudinal axes of the drive actuator and the rotational motion of the steering assembly translates into proximal and distal translation of the steering assembly in relation to the outer cannula.

These aspects can further comprise one or more cylindrical slots of corresponding diameter and proximal-distal position within the steering assembly to interact with one or more washers present at the proximal end of the outer cannula and outer cannula cover and at the diametrically differing interfaces between the drive barrel and drive shaft.

In a thirteenth aspect, the adjustable device delivery system of the above aspects can further comprise a lock system comprising an inner surface and an outer surface, the inner surface of a diameter corresponding to the outer diameter of the proximal end of the outer cannula cover and threaded to facilitate its rotatable attachment to the correspondingly threaded proximal end of the outer cannula cover. The lock system can lock the position of the steering assembly, drive actuator, inner drive cannula and adjustable internal door by rotatably butting against, or resting against and in contact with, the steering assembly on the threads of the outer cannula cover preventing the movement of the steering assembly, drive actuator, inner drive cannula and adjustable internal door. Likewise, the lock system can unlock the position of the steering assembly, drive actuator, inner drive cannula and adjustable internal door by rotatably moving away from the steering assembly on the threads of the outer cannula cover enabling the movement of the steering assembly, drive actuator, inner drive cannula and adjustable internal door.

In a fourteenth aspect, the adjustable internal door can deflect or focus electromagnetic radiation. Further, the adjustable device delivery system of this aspect can further comprise a means for detecting electromagnetic radiation deflected, and optionally focused, by the adjustable internal door, the radiation moving in a distal-to-proximal direction in the adjustable device delivery system.

The devices disclosed in the previously-described aspects of the invention this comprise a fifteenth aspect, wherein the devices of the invention comprise an apparatus for delivering a device to a confined space, preferably a confined space in an animal body.

In a sixteenth aspect, the invention provides a method of delivering a device to an confined space comprising the steps of inserting the adjustable device delivery system of the above aspects into the confined space; guiding the adjustable device delivery system to a delivery location in the confined space for the object to be deployed; orienting the adjustable device delivery system wherein the slot in the distal end of the outer cannula faces the desired delivery location; adjusting the adjustable internal door to a user-defined angle for delivery of the device; delivering the device to the delivery location through the lumen of the adjustable device delivery system tubular body in a proximal to distal direction, wherein the device is deflected off of the adjustable internal door at about the user-defined angle of the adjustable internal door. This aspect of the invention can further comprise the step of removing the device delivery system from the confined space with the device remaining within the confined space. Alternatively, this aspect of the invention can further comprise the step of removing the device from the confined space along with the device delivery system.

In a seventeenth aspect, the invention provides a method of deploying a medical device at a user-defined angle comprising the steps of inserting the adjustable device delivery system of the above aspects into a space that is connected or proximal to a medical device delivery location; guiding the adjustable device delivery system to the medical device delivery location within or proximal to the space; orienting the adjustable device delivery system wherein the slot in the distal end of the outer cannula faces the desired direction of medical device deployment; adjusting the adjustable internal door to a user-defined angle for delivery of the medical device; and delivering the medical device to the delivery location through the lumen of the adjustable device delivery system tubular body in a proximal to distal direction wherein the medical device is deflected off of the adjustable internal door at about the user-defined angle of the adjustable internal door. This aspect of the invention can further comprise the step of removing the device delivery system from the medical device delivery location with the medical device remaining within the delivery location wherein the angle of delivery of the medical device is not altered due to presence of the slot in the distal portion of the tubular body through which the medical device can slide during removal of the device delivery system.

In a eighteenth aspect, the invention provides a method of forming a pathway between bodily compartments comprising the steps of inserting the adjustable device delivery system of the above aspects into a first space that is proximal to a second space into which the pathway is to be formed; guiding the adjustable device delivery system to a bodily compartment connection location within the first space; orienting the adjustable device delivery system wherein the slot in the distal end of the outer cannula faces the bodily compartment connection location; adjusting the adjustable internal door to a user-defined angle for delivery of a device that can form a pathway between bodily compartments; delivering the device that can form a pathway between bodily compartments to the bodily compartment connection location through the lumen of the adjustable device delivery system tubular body in a proximal to distal direction, wherein the device is deflected off of the adjustable internal door at about the user-defined angle of the adjustable internal door; and forming the pathway between bodily compartments.

In a nineteenth aspect, the invention provides a method of visualization in an confined space using electromagnetic radiation comprising the steps of inserting the adjustable device delivery system of the fourteenth aspect into the confined space; guiding the adjustable device delivery system to a visualization location in the confined space; orienting the adjustable device delivery system wherein the slot in the distal end of the outer cannula faces the desired visualization location; adjusting the adjustable internal door to a user-defined angle to enable deflection of electromagnetic radiation moving in a proximal-to-distal direction from the adjustable device delivery system to the visualization location and, optionally, back from the visualization location in a distal-to-proximal direction through the device delivery system; delivering the electromagnetic radiation in a proximal-to-distal direction from the adjustable device delivery system to the visualization location, wherein the electromagnetic radiation is deflected off of the adjustable internal door at the user-defined angle of the adjustable internal door. The method of this aspect can further comprise the step of detecting electromagnetic radiation deflected off of the adjustable internal door, such electromagnetic radiation moving in a distal-to-proximal direction in the adjustable device delivery system.

In a twentieth aspect, the invention provides a method of delivering focused electromagnetic radiation in an confined space comprising the steps of inserting an adjustable device delivery system wherein the adjustable internal door can deflect electromagnetic radiation into the confined space; guiding the adjustable device delivery system to an electromagnetic radiation target location in the confined space; orienting the adjustable device delivery system wherein the slot in the distal end of the outer cannula faces the desired electromagnetic radiation target location; adjusting the adjustable internal door to a user-defined angle to enable delivery of focused of electromagnetic radiation moving in a proximal-to-distal direction from the adjustable device delivery system to the electromagnetic radiation target location; and delivering the electromagnetic radiation in a proximal-to-distal direction from the adjustable device delivery system to the electromagnetic radiation target location such that the electromagnetic radiation is focused by the adjustable internal door and deflected at the user-defined angle of the adjustable internal door.

In a twenty-first aspect, the invention provides methods of steering a device or device delivery system within a confined space comprising the steps of inserting an adjustable device delivery system of the above embodiments into the confined space; guiding the adjustable device delivery system to a first delivery location in the confined space for the device to be deployed; orienting the adjustable device delivery system wherein the slot in the distal end of the outer cannula faces the first delivery location; adjusting the adjustable internal door to a user-defined angle for delivery of the device; delivering the device to the first delivery location through the lumen of the adjustable device delivery system tubular body in a proximal to distal direction wherein the device is deflected off of the adjustable internal door at about the user-defined angle of the adjustable internal door; advancing the adjustable device delivery system along the path of delivered device to the first delivery location; and repeating the above steps to steer the device or device delivery system to second, third, fourth delivery locations and beyond.

In all of the above aspects of the invention, the device delivered by the adjustable device delivery system can be a medical or non-medical device. Further, the location to which a medical or non-medical device is delivered can be in a biological or non-biological system.

Specific preferred embodiments of the invention will become evident from the following more detailed description of certain preferred embodiments and the claims

BRIEF DESCRIPTION OF THE DRAWINGS

FIG. 1a is a top-right isometric view of the adjustable device delivery system with a box illustrating the area that is shown in detail in FIG. 1b.

FIG. 1b is a top-right hidden line view demonstrating distal end of adjustable device delivery system with the adjustable internal door in a closed position.

FIG. 1c is a top-right isometric view of the adjustable device delivery system with a box illustrating the area that is shown in detail in FIG. 1d.

FIG. 1d is a top-right hidden line view demonstrating the proximal end of the adjustable device delivery system with outer cannula cover, or handle, lock system, drive actuator and steering assembly.

FIG. 2a is a top-right isometric view of the inner drive cannula with a box illustrating the area shown in detail in FIG. 2b.

FIG. 2b is a top-right hidden line view demonstrating the drive actuator on the proximal end of the inner drive cannula that interacts with the steering assembly.

FIG. 2c. is a top-right isometric view of the inner drive cannula with a box illustrating the area that is shown in detail in FIG. 2d and FIG. 2e.

FIG. 2d is a top-right hidden line view demonstrating the distal end of the inner drive cannula, which interacts with one or more door connectors that comprise the door connector system.

FIG. 2e is a top-right face view demonstrating the distal end of the inner drive cannula that interacts with one or more door connectors that comprise the door connector system.

FIG. 2f is a bottom-right isometric view of the inner drive cannula with a box illustrating the area that is shown in detail in FIG. 2g.

FIG. 2g. is a bottom-right face view of the distal end of the inner drive cannula demonstrating how it interacts with the adjustable internal door and one or more door connectors.

FIG. 2j is a side view of the inner drive cannula with an isometric box illustrating the area that is shown in detail in FIG. 2k.

FIG. 2k is a front view of the distal end of the inner drive cannula.

FIG. 4a is a side view of a door connector.

FIG. 4b is a top view of a door connector.

FIG. 5 is an isometric view of an exemplary axle that hingedly connects the door body to the distal portion of the outer cannula.

FIG. 5a is a side view of an axle.

FIG. 5b is a top view of an axle.

FIG. 7a is an isometric view of the outer cannula with a box illustrating the area, which is shown in detail in FIG. 7b.

FIG. 7b is a top-right cut-away view of the outer cannula demonstrating the axle shell and slot.

FIG. 7c is an isometric view of the outer cannula with a box illustrating the area, which is shown in detail in FIG. 7d.

FIG. 7d. is a cut-away front view looking down the distal end of the outer cannula.

FIG. 7e is an isometric view of the outer cannula with a box illustrating the area, which is shown in detail in FIG. 7f.

FIG. 7f. is a cut-away front view looking down the proximal end of the outer cannula.

FIG. 8a is a top-right face view of the adjustable internal door, door connectors, axle and inner drive cannula demonstrating the interaction of the inner drive cannula and the adjustable internal door in an open position.

FIG. 8b is a top-right face view of the adjustable internal door, door connectors, axle and inner drive cannula demonstrating the interaction of the inner drive cannula and the adjustable internal door in an about 45 degrees closed position.

FIG. 8c is a top-right face view of the adjustable internal door, door connectors, axle and inner drive cannula demonstrating the interaction of the inner drive cannula and the adjustable internal door in a 90 degree, or closed, position.

FIG. 8d is a right side hidden line view of the distal end of the adjustable device delivery system with adjustable internal door in an open position.

FIG. 8e is a right-side hidden line view of the distal end of the adjustable device delivery system with an arrow indicating the proximal movement of the inner drive cannula and its translation, through a door connector, to angled movement of the adjustable internal door, here at about a 45 degree angle.

FIG. 8f is a right-side hidden line view of the distal end of the adjustable device delivery system with an arrow indicating the proximal movement of the inner drive cannula and its translation, through a door connector, to angled movement of the adjustable internal door, here at about a 90 degree angle.

FIGS. 8g, 8h, and 8i are top right surface views of the outer cannula, the slot in the outer cannula, the inner drive cannula, adjustable internal door, and door connectors. The three exemplary views correspond to the relation of the elements when the door is at about 0 degrees, about 45 degrees, and about 90 degrees. The arrows on FIG. 8h and FIG. 8i are shown to indicate the proximal movement of the inner drive cannula in relation to the distal end of the outer cannula as the door angle changes from about 0 degrees (FIG. 8g) to about 90 degrees (FIG. 8i).

FIG. 8m is a cut away view of the adjustable internal door, door connectors, and inner drive cannula, looking distally down the inner drive cannula to demonstrate the clear pathway down the lumen of the adjustable device delivery system when the door is in an open position.

FIG. 8n is a cut away view of the adjustable internal door, door connectors, and inner drive cannula, looking distally down the inner drive cannula to demonstrate the partially blocked longitudinal pathway down the lumen of the adjustable device delivery system when the door is in a 45 degree position.

FIG. 8o is a cut away view of the adjustable internal door, door connectors, and inner drive cannula, looking distally down the inner drive cannula to demonstrate the blocked longitudinal pathway down the lumen of the adjustable device delivery system when the door is in a closed, 90 degree position.

FIG. 9 is a top-right isometric view of the adjustable device delivery system with an isometric box illustrating the area, which is shown in detail in FIG. 9b.

FIG. 9b is a cut-away front view looking distally down the longitudinal axis of the adjustable device delivery system demonstrating an exemplary fit of an inner drive cannula in an outer cannula.

FIG. 9c is a top-right isometric view of the adjustable device delivery system with an isometric box illustrating the area, which is shown in detail in FIG. 9d.

FIG. 9d is a cut-away view demonstrating an exemplary fit of the adjustable internal door in relation to the inner drive cannula and the outer cannula when said door is closed at a 90 degree position.

FIG. 9e is a top-right isometric view of the adjustable device delivery system with an isometric box illustrating the area, which is shown in detail in FIG. 9f.

FIG. 9f is a cut-away view demonstrating an exemplary fit of the adjustable internal door in relation to the inner drive cannula and the outer cannula when said door is open at a 0 degree position.

FIG. 10a is a top-right cut-away view of an exemplary outer cannula cover.

FIG. 10b is a front view of an outer cannula cover.

FIG. 10c is a side view of an outer cannula cover.

FIG. 10d is a view of an exemplary washer that can be placed at the interface between the drive actuator at the proximal end of the inner drive cannula and the steering system.

FIG. 10e is a view of an exemplary washer that can be placed between the outer cannula cover and the distal interior edge of the steering system.

FIG. 11a is an isometric view of the proximal portion of the adjustable device delivery system, including an inner drive cannula, outer cannula, and outer cannula cover, with a box illustrating the area, which is shown in detail in FIG. 11b.

FIG. 11b is a top-right view that demonstrates an exemplary fit of an inner drive cannula and an outer cannula in relation to an optional outer cannula cover.

FIG. 11c is a side view of the proximal portion of the adjustable device delivery system, including an inner drive cannula, outer cannula, and outer cannula cover, with a box illustrating the area, which is shown in detail in FIG. 11d.

FIG. 11d is a side view that demonstrates an exemplary fit of an inner drive cannula and an outer cannula in relation to the optional outer cannula cover.

FIG. 11e is a side view of the proximal drive system with a box illustrating the area, which is shown in detail in FIG. 11f.

FIG. 11f is a side hidden-line view of the proximal portion of the adjustable device delivery system, including an inner drive cannula, the proximal portion of which comprises a drive actuator, outer cannula, and an outer cannula cover, with a cutaway view of half of the steering assembly also shown. An exemplary relationship between the steering assembly and the drive actuator can be seen, wherein, in this example, the drive actuator comprises washers at the interface between steering assembly and the drive actuator.

FIG. 11g is a side hidden-line view of the proximal portion of the adjustable device delivery system including an exemplary relationship of correspondingly threaded surfaces of the outer cannula cover (when used) and the steering assembly.

FIG. 12a is an isometric view of the adjustable device delivery system with an isometric box illustrating the area that is shown in detail in FIG. 12b.

FIG. 12b is a top-right hidden-line view of a steering assembly.

FIG. 12c is an isometric view of the adjustable device delivery system with a box illustrating the area, which is shown in detail in FIG. 12d.

FIG. 12d is a top-right cut-away view of the steering assembly which projects motion of the related drive actuator on the proximal end of the inner drive cannula when the steering assembly is rotated.

FIG. 12e is a hidden-line side view of the proximal portion of the adjustable device delivery system demonstrating the steering apparatus toward the distal end of its motion, in this example corresponding to an open door position of about 0 degrees.

FIG. 12f is a hidden-line side view of the proximal portion of the adjustable device delivery system demonstrating the steering apparatus toward the proximal end of its motion, in this example corresponding to a closed door position of about 90 degrees.

FIG. 12g is a hidden-line side view of the proximal portion of an exemplary adjustable device delivery system demonstrating the steering apparatus when the adjustable internal door is in the open position and a lock system is in an open, unlocked position.

FIG. 12h is a hidden-line side view of the proximal portion of an exemplary adjustable device delivery system demonstrating the steering apparatus when the adjustable internal door is in the open position and a lock system is in a closed, locked position.

FIG. 13a is an isometric view of the adjustable device delivery system with a box illustrating the area, which is shown in detail in FIG. 14b.

FIG. 13b is a top-right face view of an exemplary outer cannula cover, or handle.

FIG. 14a is an isometric view of an adjustable device delivery system with a box illustrating the area, which is shown in detail in FIG. 15b.

FIG. 14b is a top-right face view of an exemplary lock system.

FIG. 15e shows a device, such as an intravascular ultrasound, passed down the lumen of the adjustable device delivery system.

FIG. 15l shows the drainage catheter in the same position with the adjustable internal door in a fully opened position.

FIG. 15m shows the adjustable device delivery system being removed from the lumen without disrupting the placement of the drainage catheter.

DETAILED DESCRIPTION OF THE INVENTION

This invention provides an adjustable device delivery system capable of deploying various medical and non-medical devices to biological and non-biological systems at angles different from the angle of the lumen or space within which the present invention is passed. The delivery angle of the devices of the invention is also preferably different from the angle of the body of the device delivery system. The device delivery systems of the present invention advantageously permit a delivered device to retain its angle of delivery despite removal of the device delivery system. The present invention also provides methods of utilizing the adjustable device delivery systems of the invention.

As used herein, the words "longitudinal" and "proximal-distal" and the like describe the long axis of the adjustable device delivery system of the invention. For example, "longitudinal movement" or "proximal-distal movement" generally describes movement in either direction along the long axis of the adjustable device delivery system of the invention. Embodiments that are referred to as "proximal" are located nearer the end of the adjustable device delivery system that comprises, for example, the steering assembly. Embodiments that are referred to as "distal" are located nearer the end of the adjustable device delivery system that comprises, for example, the slot and the adjustable internal door. Likewise, "proximal" movement refers to movement of, for example, a medical device within the adjustable device delivery system of the invention toward the end that comprises the steering assembly. "Distal" movement refers to movement in the direction opposite proximal movement, i.e. toward the end of the adjustable device delivery system that comprises, for example, the slot and the adjustable internal door.

As used herein, the words "corresponding," "correspondingly," "complementary," and the like, describe embodiments that operably interact. For example, a bolt and a matching nut that operably interact, i.e., "screw together," would be referred to herein as being "correspondingly threaded" or having "complementary threads" or "complementary surfaces," and the like.

As used herein, the word "confined," "confined space," and the like, describe spaces that are generally not easily or readily accessible, for example, in the lumen of a blood vessel in a biological system, into which a medical, non-medical or EMR device need be delivered. The adjustable device delivery system of the invention can also be utilized in easily accessible, unconfined spaces.

The invention is now particularly described with reference to the drawings, which are provided herein to facilitate appreciation of certain aspects of the invention but which are not limiting to the scope of the appended claims.

Figure 1:
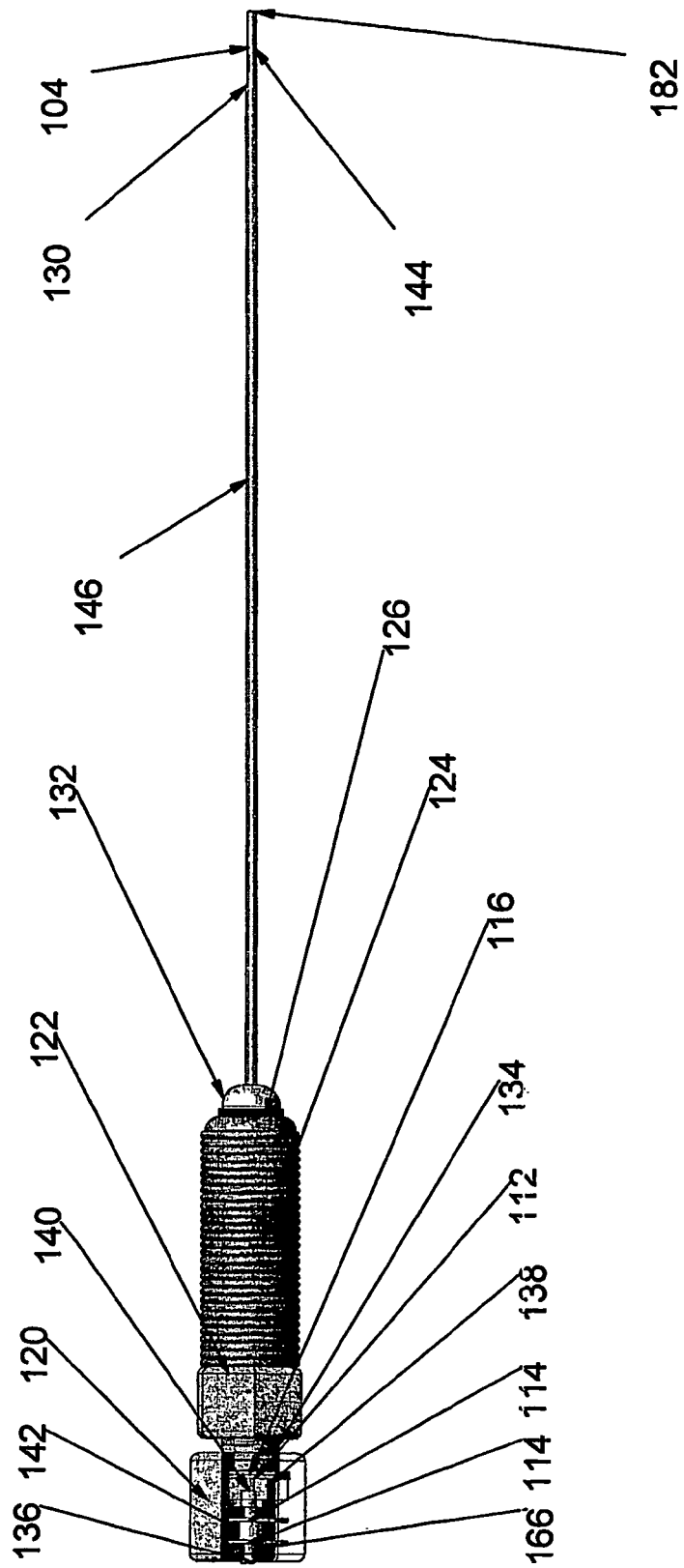
FIG. 1 is a side view of the adjustable device delivery system with a transparent bottom half of the steering assembly.

FIG. 1 is a side shaded view of an embodiment of the adjustable device delivery system of the invention. The inventive catheter components include an outer cannula (146; synonymous with outer cannula shaft) of any suitable length, an inner drive cannula (140), an outer cannula cover that can optionally be used as a handle (124), a steering assembly (120), a lock system (122), and an adjustable internal door (104) that rotates in relation to the outer cannula by use of an axle (144) assembly.

Advantageously, the outer cannula is slotted (130) at its distal end, which slot has a proximal end and a distal end. In preferred embodiments, the proximal end of the slot starts proximal to the adjustable internal door and continues to the distal end of the outer cannula (182). In preferred embodiments, the distal end of the slot and the distal end of the outer cannula coincide. The location of the slot is illustrated in FIG. 1a. FIG. 1b shows the assembly in more detail and demonstrates the adjustable internal door assembly. The adjustable internal door (104) is preferably located inside of the outer cannula (146), between the proximal end of the slot in the outer cannula (130) and the distal end of the outer cannula (182). The adjustable internal door can be connected to the outer cannula opposite the distal cut away slot (130) by means of a door hinge (208) connected to an axle (144) that resides in an axle shell (128), which can be embedded in the interior surface of the outer cannula (188). This adjustable internal door assembly allows the door one degree of freedom wherein the door can hingedly move from an open position in which the door lies parallel to the longitudinal axis of the outer cannula to a closed position in which the door sits perpendicular to the longitudinal axis of the outer cannula.

The adjustable internal door (104) has hinge holes in its outer edges (152), which are analogous to hinge holes in the distal end of the inner drive cannula (154). These hinge holes are the sites of insertion for the insertion tabs on the proximal and distal ends of one or more door connectors (108). The interior surface of the outer cannula advantageously can have cut-away slots to accommodate the inner drive catheter and the movement of the adjustable internal door, axle, connector elements, and any means by which the adjustable internal door hingedly moves without collision. Item (148) represents a side guide track on which the inner drive cannula can slide. Tracks on the inner drive cannula can fit into corresponding guide tracks in the outer cannula. The guide track and corresponding track elements comprise a track system that facilitates proximal-distal motion of the inner drive cannula within the outer cannula. Item (158) demonstrates the distal edge of a cut-away track allowing unobstructed movement and rotation of the one or more door connectors.

FIG. 1d illustrates in detail the structures shown in FIG. 1c. FIG. 1d demonstrates the proximal end of the adjustable device delivery system of the invention. The shafts of the outer cannula (146) and inner drive cannula (140) can fit inside of an outer cannula cover assembly, or handle. The inner drive cannula slides proximally and distally guided by the guide track inside of the outer cannula. The outer catheter cover, or handle assembly, can include a surrounding handle cover (132) and an operator handle surface (124). The steering assembly (120) is also illustrated. The steering assembly controls proximal and distal movement of the inner drive cannula in relation to the outer cannula through its interaction with the steering actuator. A series of washers (114) can optionally be present that surround the drive shaft (142) of the proximal end of the inner drive cannula to ensure that rotational movement of the steering system (120) is not translated as torque to the inner or outer cannulas. Medical devices, such as, for example, guidewires or stents, or non-medical devices can be inserted through the proximal end of the inner drive cannula (160) into the interior shaft (136). These instruments pass down the barrel of a preferably cylindrical surface. The two halves of the generally cylindrical passage-way are formed by the superior interior portion of the outer cannula and the interior superior portion of the inner drive cannula (shown in FIG. 9b ELEMENT 168) in a straight path (170). When the door is in a 90 degree position relative to the longitudinal axis of the outer cannula, the medical or non-medical devices will be deflected at an about 90-degree angle off the proximal face of the door (FIG. 1b ELEMENT 212) and out the cut-away slot of the outer cannula (FIG. 1b ELEMENT 130). When the door is in an open, 0-degree position, medical and non-medical devices can pass straight down the path (170), unobstructed, and pass out the distal end of the outer cannula (FIG. 1b ELEMENT 182).

Inner Drive Cannula

The box in FIG. 2a provides a proximal view of the inner drive cannula. FIG. 2b shows the proximal end of the inner drive cannula in detail. While the distal portion of the shaft of the inner drive cannula (140) is not a complete cylinder, i.e., an "open shaft", the drive barrel (166) is cylindrical and does not have an outer cutaway surface. The drive barrel (166) connects to an enlarged drive shaft (142). Alternatively, the drive shaft can be of a smaller diameter than the drive barrel. The drive shaft and/or drive barrel interacts with the steering assembly, optionally via a system of washers. Preferably, the first washer lies flush on the proximal surface of the drive shaft (162) while the second is located flush to the distal surface (164). Where the drive shaft is of a smaller diameter than the drive barrel and washers are present, the first washer lies flush at the proximal interface of different radii between the drive barrel and the drive shaft and the second washer is positioned at the distal interface of different radii between drive barrel and drive shaft. The drive barrel (166), drive shaft (142) and, optionally, washers comprise the drive actuator, which is located at the proximal end of the inner drive cannula. The drive actuator can be directly associated, or in contact, with the proximal end of the inner drive cannula or indirectly associated, for example, through one or more intermediate elements. For example, the drive actuator and inner drive cannula can interact through a set of gears to increase or decrease the longitudinal movement of the steering assembly or through a compressible member, like an elastomer, to elastically transmit the longitudinal force of the steering assembly to the adjustable internal door at the distal end of the inner drive cannula. In these embodiments, a medical or non-medical device inserted into the proximal opening (136) at the proximal end of the inner drive cannula (160) is advanced by a user or a machine down the drive barrel (166) and drive shaft (142) and continues distally (170), to the adjustable internal door, where it later interacts therewith.

The box in FIG. 2c illustrates a distal view of the inner drive cannula, and FIG. 2d illustrates a hidden line view of the distal portion of the shaft (140) of the inner drive cannula. The distal shaft is not necessarily a complete cylinder but can approximate the lower half of a cylinder with a superior internal face (168) that is shaped to allow the inferior path (170) of an inserted medical or non-medical device.

The distal portion of the inner drive cannula is further illustrated in FIG. 2e. The inner drive cannula can have cut-away surfaces to accommodate other parts of the adjustable internal door and the door connector system, which is comprised of one or more door connectors. The inner drive cannula can also include hinge holes (154) that accommodate the proximal inner drive cannula insertion tab of the door connectors (not shown). Because the adjustable internal door and door connector system do not collide with the outer edge of the inner drive cannula or the inner edge of the outer cannula, surfaces are cut-away (172) where necessary to allow space for the movement of the moving parts at the distal end of the adjustable device delivery system. Because the bottom edge of the inner drive cannula does not collide with the axle or door assembly, the bottom edge is cutaway (174) where necessary in similar fashion. The distal edge (150) of the inner drive cannula is rounded to accommodate these cutaway surfaces.

The box in FIG. 2f represents the lower-right hand view of the distal edge of the inner drive cannula demonstrated in FIG. 2g. FIG. 2g further illustrates additional surfaces that can interact with the outer cannula. The inner drive cannula can slide forward and backward (proximally and distally) in relation to the outer cannula. The inner drive cannula can slide within the outer cannula via one or more tracks on the side (176) and/or one or more tracks on the bottom (178) located on the external surface of the inner drive cannula. Cutaway surfaces on the distal end of the inner drive cannula (172, 174) can be included to facilitate proximal-distal movement (i.e., movement along the longitudinal axis of the outer cannula) of the inner drive cannula within the outer cannula. For example, cutaway surfaces can be included on the distal end of the inner drive cannula to provide space (174) within which an axle or axle shell can slide as the inner drive cannula moves distally within the outer cannula or space (172) within which one or more door connectors can move, translating the longitudinal movement of the inner drive cannula within the outer cannula into hinged movement of the adjustable internal door.

Figure 2H:
FIG. 2h is a right view of the inner drive cannula with a box illustrating the area that is shown in detail in FIG. 2i.
Figure 2I:
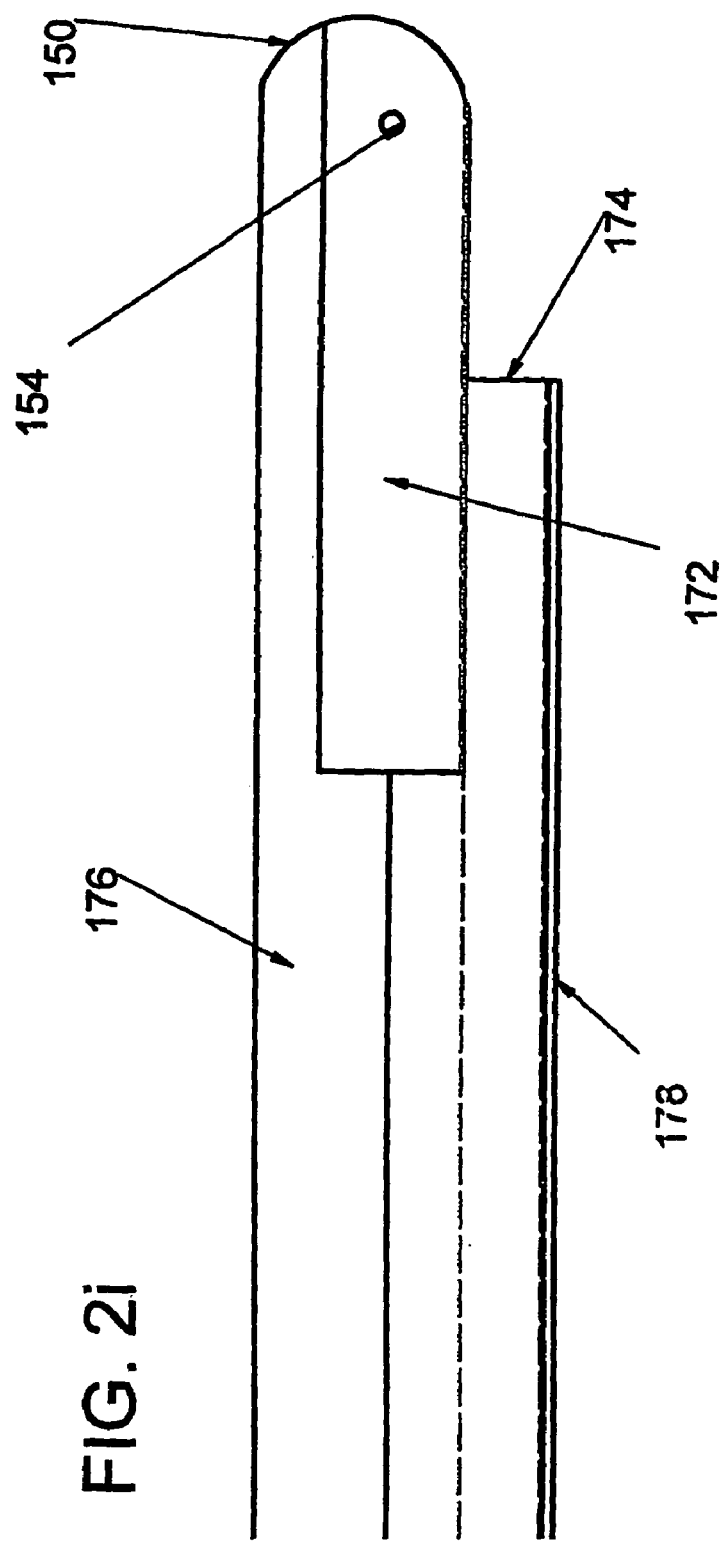
FIG. 2i is a side view of the distal end of the inner drive cannula that demonstrates the attachment location of the one or more door connectors and their interaction with the adjustable internal door.

The box in FIG. 2h shows a side view that is shown in further detail in FIG. 2i. The hinge hole for a door connector (154) can be located proximal to the distal edge of the inner drive cannula (150). The inner drive cannula can slide in a proximal-distal direction, optionally, on one or more side tracks (176) and/or one or more bottom tracks (178) that correspond to analogous geometries on the interior surface of the outer cannula, or side guide tracks and bottom guide tracks. The distal end of the inner drive cannula can have cutaway surfaces. For example, in FIGS. 2h-2i, cutaway surface 172 and cutaway surface 174 can accommodate the one or more door connectors and adjustable internal door, respectively.

The box in FIG. 2j illustrates a cut-away front view of the distal portion of the inner drive cannula. The outer surface can be generally cylindrical. However, the inner drive cannula can have projections that form one or more side tracks (176) and/or one or more bottom tracks (178) to ensure smooth movement inside of the outer cannula. In this figure, three surfaces are cut away from this external edge including the side (172) cutaways that accommodate the one or more door connectors, and the bottom cutaway (174), that accommodates the adjustable internal door. The present invention can also be constructed without cutaways for side or bottom tracks or cutaways for one or more door connectors and adjustable internal door clearance so long as proximal-distal motion of the inner drive cannula is possible and the angle of the adjustable internal door can be changed in a user-definable manner. Hinge holes (154) for the proximal inner drive cannula insertion tabs of the door connectors are also shown. In use, the medical or non-medical device travels down the path (170), wherein the path's inferior surface is defined by the interior surface (168) of the inner drive cannula, and the path's superior surface is defined by the inferior surface of the outer cannula (FIG. 9b; also ELEMENT 168).

Door

Figure 3:
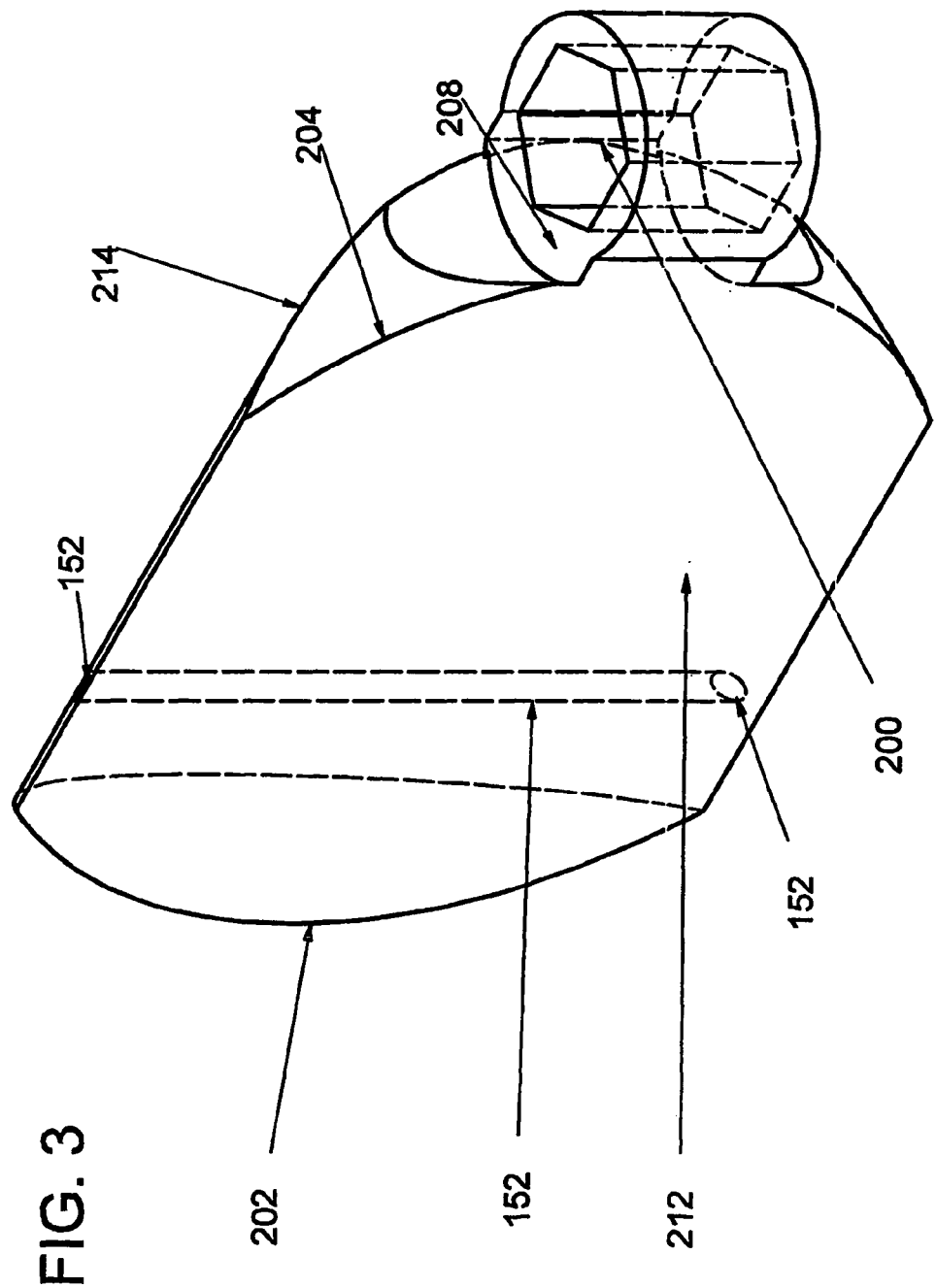
FIG. 3 is a cut-away view of the adjustable internal door without additional structures, such as, for example, one or more door connectors or an axle, which comprises a door body.

FIG. 3 shows a top-right hidden line view of the adjustable internal door. The adjustable internal door has a proximal face (212) and a distal face (214). The proximal face (212) can be flat or shaped, for example, convex shaped, and is responsible for the internal collision of medical device, non-medical device or electromagnetic radiation (or waves; "EMR") that deflects such device or EMR at the desired angle. The distal face (214) can be flat or shaped. Preferably, the distal face is shaped to fit in the device so that its outer geometry approximates the inner geometry of the outer cannula. The distal edge of the door (212) can be curved or flat. Preferably, the distal edge is curved so that its geometry corresponds with the outer geometry of the outer cannula when the adjustable internal door is in the closed position. The door (152) can accommodate a hole through its width, or one or more holes introduced in each side that accommodate the insertion of the proximal inner drive cannula insertion tab of one or more door connectors. The inferior portion of the door (204; or "bottom" with the door at a 90-degree angle in relation to the longitudinal axis of the outer cannula) comprises a hinge (208) surface and an axle insertion surface (200). The shape of the axle insertion surface can be of any shape but preferably corresponds to the shape of the middle portion of the axle (FIG. 5b ELEMENT 262). The superior edge of the adjustable internal door (202) can also be curved or straight. If curved, the adjustable internal door can better avoid external collision between the door and outer cannula.

Figure 3A:
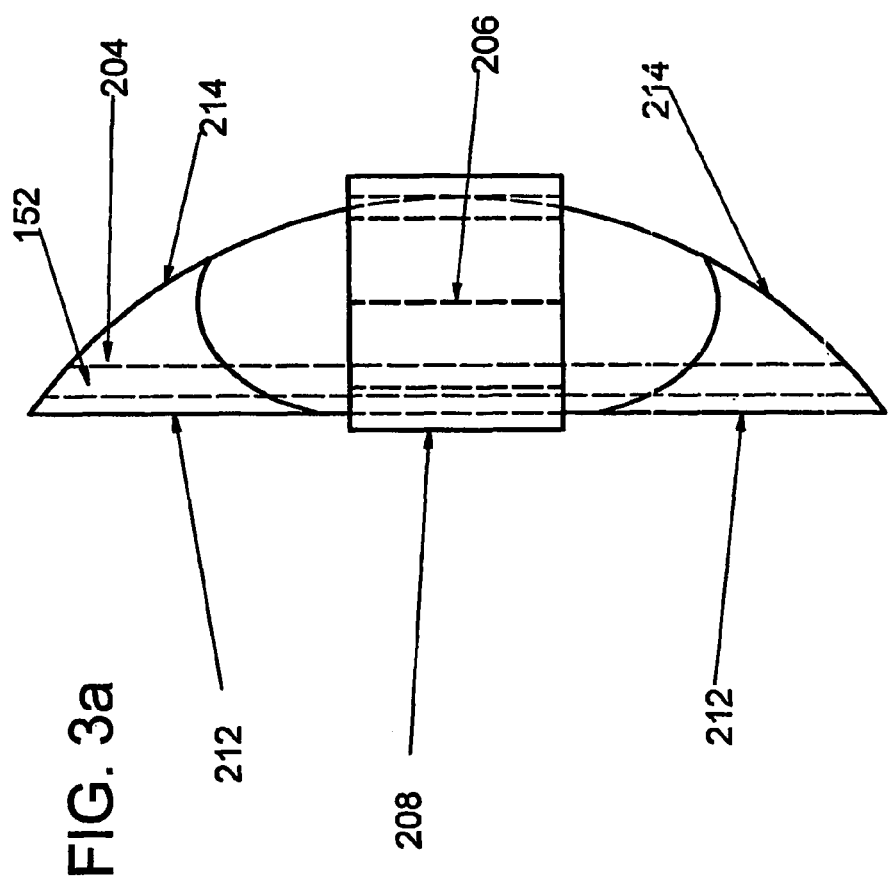
FIG. 3a is a cut-away view of the adjustable internal door from the perspective of looking down the hinge of the door.

FIG. 3a shows a bottom view of the door. This view illustrates one of the possible configurations of the proximal (212) and distal (214) faces of the adjustable internal door. The door hinge hole (152) is shown to be just distal to the proximal face of the door, but can be located closer to the distal edge if desired.

Figure 3B:
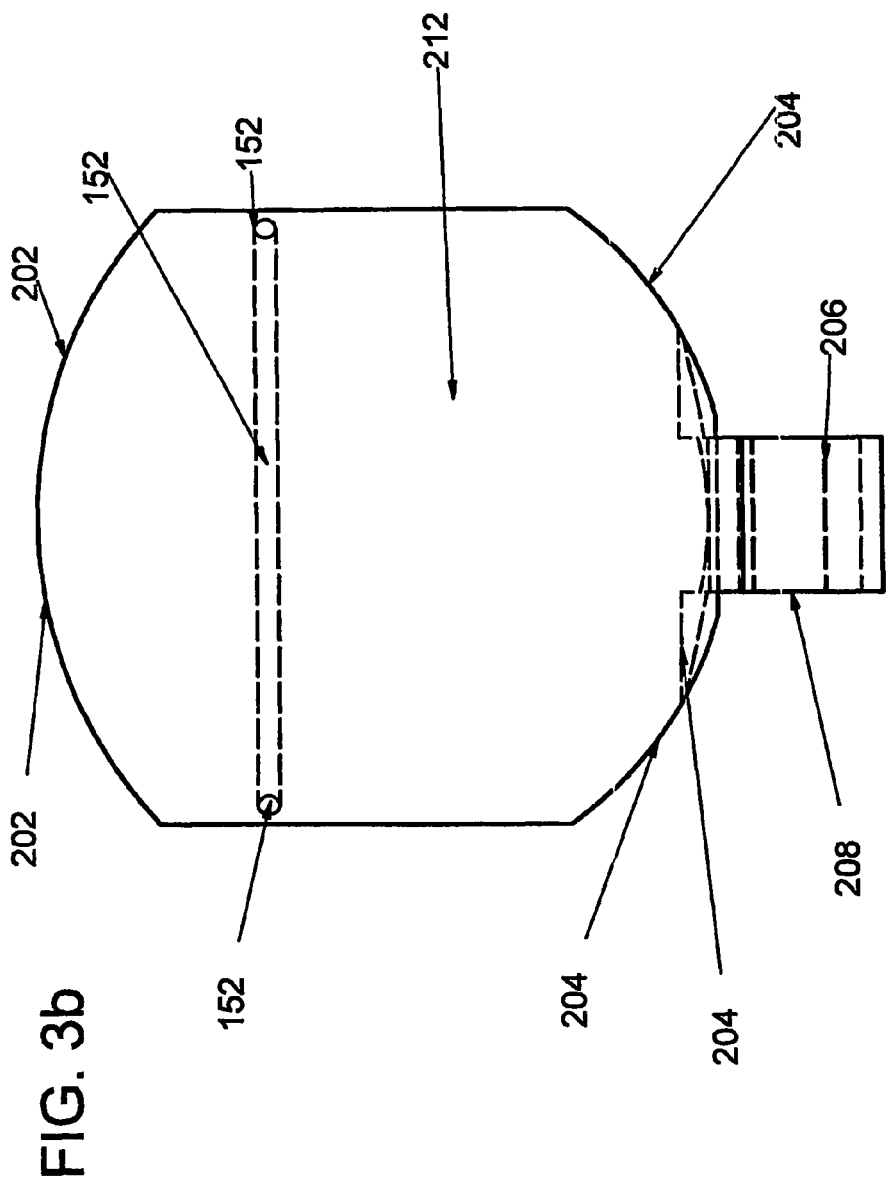
FIG. 3b is a cut-away view of the proximal face of the adjustable internal door.

FIG. 3b shows a front view of the door that would be appreciated when looking down the barrel of the adjustable device delivery system in a proximal-to-distal direction with the door closed to a 90-degree position. Deflections are made between the inserted medical device, non-medical device or EMR and the front face of the door (212). The distance between the door hinge (208) and the superior edge of the door (202) can be constructed so that the door fits exactly inside of the outer cannula. However, such a tight fit is not usually necessary and the door may be shaped to reflect an imperfect fit. When the door is at about a 90-degree in relation to the outer cannula, the circumference of the door can correspond to the geometry of the outer cannula and generally does not project outside of the outer cannula outline. Nevertheless, where the slot in the distal end of the outer cannula comprises 50 percent or more of the outer cannula circumference, the adjustable internal door can project outside the outer cannula outline when the door is at a 90-degree angle.

Figure 3C:
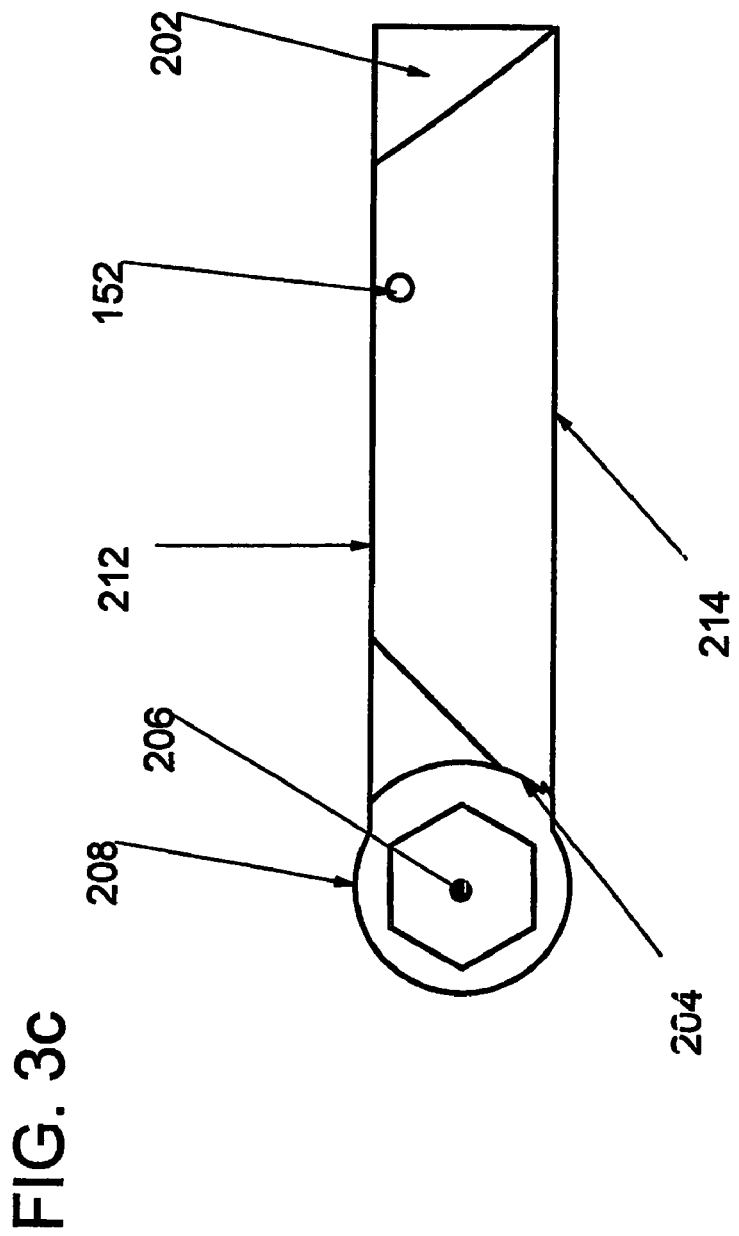
FIG. 3c is a view of the adjustable internal door from the perspective of looking down a side surface of the door body.

FIG. 3c shows a side view of the door. This view demonstrates an exemplary position of a hinge hole (152) in relation to the proximal (212) and distal (214) faces of the adjustable internal door. The distance between the door hinge hole and the superior edge of the adjustable internal door is also exemplary and the one or more door hinge holes can be relocated to other locations in the side surfaces of the adjustable internal door.

Door Connector System

Figure 4:
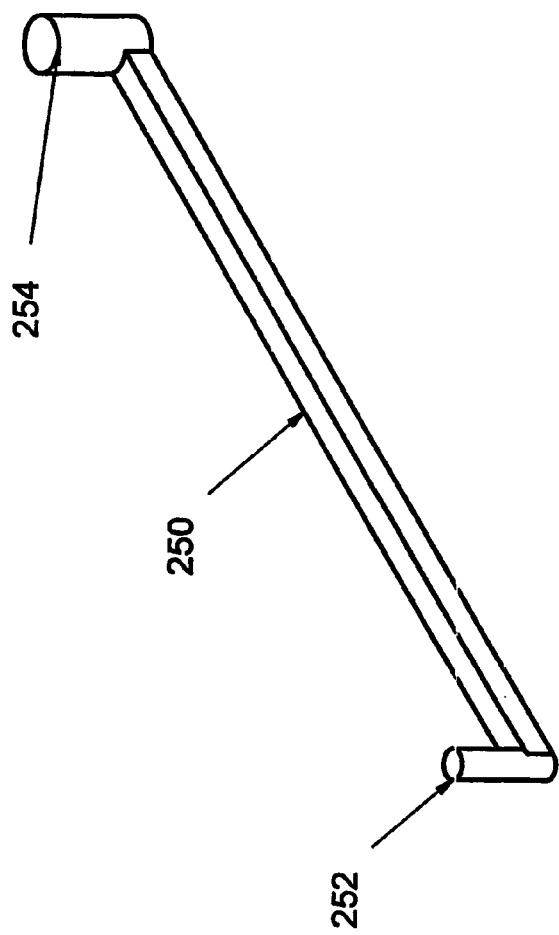
FIG. 4 is an isometric view of a door connector, one or more of which can comprise the door connector system.

FIG. 4 shows door connectors consisting of a shaft (250) of any suitable shape, a proximal inner drive cannula insertion tab (254), and a distal door insertion tab (252). FIG. 4a shows a side view of the connectors. The shaft (250) is positioned not to interfere, collide or bind with the inner drive cannula or outer cannula through its longitudinal motion. The inner drive cannula and/or outer cannula can have cutaway surfaces to facilitate the movement of the one or more door connectors. The length of the proximal inner drive cannula insertion tab (254) and distal door insertion tab (252) can correspond to the depth of the hinge holes in the inner drive cannula and door hinge holes in the adjustable internal door.

Proximal inner drive cannula insertion tab (254) inserts inside of the inner drive cannula hinge hole (FIG. 2k ELEMENT 154). The length of insertion tab (254) should preferably be such that it does not project past the superior interior surface of the inner drive cannula (FIG. 2k ELEMENT 168) and into the path of the inserted medical, non-medical or EMR device (FIG. 2k ELEMENT 170).

Distal door insertion tab (252) fits inside of the door hinge hole (item 152, FIG. 3). The length of insertion tab (252) should preferably be less than one half the width of the door so that the two insertion tabs opposite each other do not push on one another. Nevertheless, embodiments comprising a distal door insertion tab that extends beyond half the width of the adjustable internal door are contemplated. A top view of the connection system is shown in FIG. 4b.

Thus the one or more door connectors link the inner drive cannula to the adjustable internal door and translate longitudinal movement of the inner drive cannula within the outer cannula to longitudinal (with respect to the outer cannula) motion of the superior edge of the adjustable internal door. The adjustable internal door can rotate from about 0-degrees, or essentially aligned with the longitudinal axis of the adjustable device delivery system to about 90-degrees, or approximately perpendicular to the longitudinal axis of the adjustable device delivery system. In certain embodiments, the adjustable internal door can be rotated more than 90 degrees.

More traditional wire or ribbon-based systems, similar to those used to steer steerable catheter systems (for example, see U.S. Pat. No. 6,530,914), are also contemplated for door movement. For example, one or more manipulation members can attach to the side surfaces of the adjustable internal door, which members can run proximally from the adjustable internal door, through the lumen of the adjustable device delivery system to the proximal end, where the user can adjust the angle of the door by exerting pulling or pushing forces on the manipulation member. Alternatively, the one or more manipulation members can reside in one or more lumens separate from the lumen through which the medical device, non-medical device or EMR is delivered.

Axle

An axle is shown in FIG. 5. The axle preferably comprises a cylindrical tube (260) comprising a middle portion and cylindrical side portions. The outer geometry of the middle portion of the axle (262) preferably corresponds to axle insertion surface (FIG. 3 ELEMENT 200) of the adjustable internal door. Further, the length of the middle portion of the axle (262) preferably corresponds to the length of the door hinge surface (FIG. 3 ELEMENT 208). The entire length of the axle preferably approximates the length of the cutaway section of the outer cannula axle shell (FIG. 7d ELEMENT 188). FIG. 5b shows a top view of the axle and FIG. 5a shows a side view. In the adjustable device delivery systems of the invention, the side cylindrical surfaces of the axle can also rotate on bearings that reside in the axle shell.

Door Assembly

Figure 6:
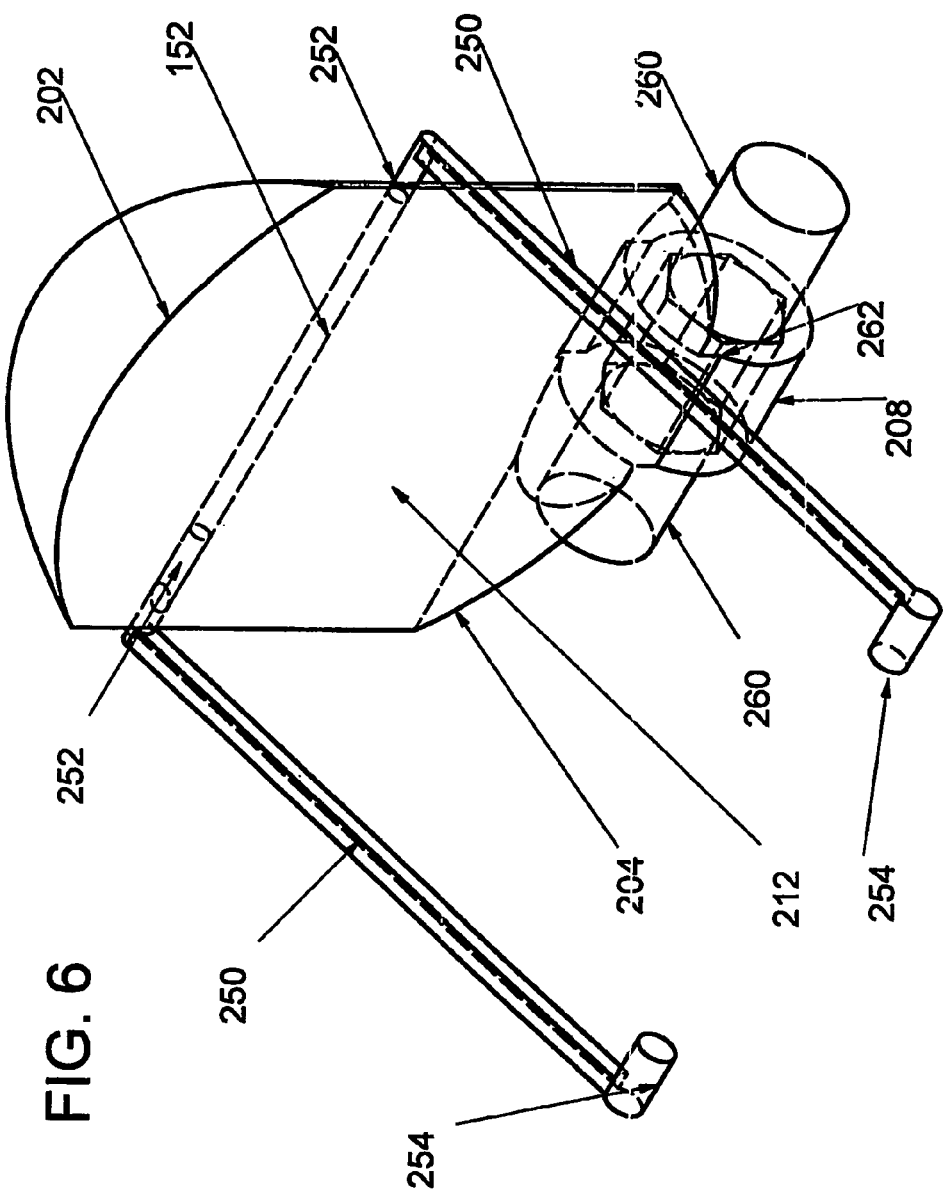
FIG. 6 is a top-right cut-away view demonstrating the adjustable internal door, axle, and door connectors.

FIG. 6 shows an adjustable internal door body, i.e., a door without attachments such as an axle or door connectors, along with two door connectors and an axle attached in one exemplary position. One or more distal door insertion tabs (252) fit inside one or more door hinge holes (152) and one or more proximal inner drive cannula insertion tabs (254) fit inside of one or more hinge hole on the distal portion of the inner drive cannula (FIG. 2k ELEMENT 154). The middle portion of the axle (262) inserts inside the door hinge surface (208). The cylindrical side portions of the axle (260) fit into the axle shell (FIG. 7d ELEMENT 128), such that the adjustable internal door can rotate without colliding with the inner drive cannula or the outer cannula.

Outer Cannula

Figure 7:
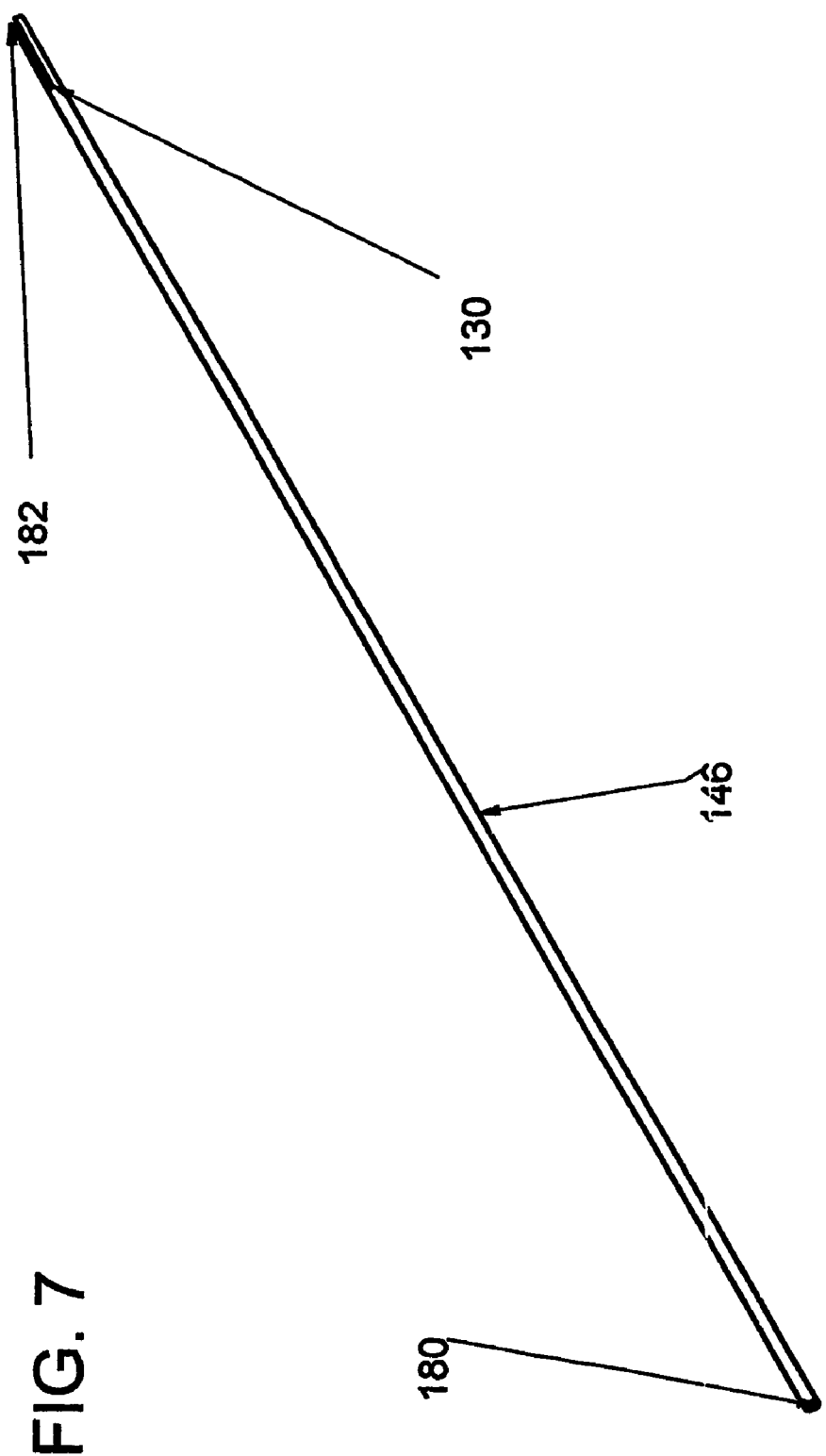
FIG. 7 is an isometric face view of the outer cannula

FIG. 7 shows a top-right view of the outer cannula. The outer cannula is generally a cylinder with a proximal end (180), a distal end (182), with a hollow shaft (146) extending between the proximal end and distal end, an inner surface, an outer surface and a circumference. The distal end of the outer cannula (182) can have a portion of its circumference cut away to form a slot (130). The size of the slot, both the longitudinal length and the percentage of the circumference removed, can be varied based on the needs of the user or procedure. As an example, the slot can be approximately three door-lengths in length. The adjustable internal door can be located beneath the slot, such that when the door is adjusted to about a 90-degree angle in relation to the longitudinal axis of the outer cannula, the slot extends proximally from the superior surface of the adjustable internal door. For example, the slot can extend approximately one and one-half door lengths proximal to the axle shell (FIG. 7b ELEMENT 128) and extend to the distal end of the outer cannula (182). The slot (130) can comprise more than 50 percent of the circumference or less than 50 percent of the circumference, as well as about 50 percent of the circumference.

The box in FIG. 7a shows the location of the view that is shown in detail in FIG. 7b. FIG. 7b shows a top-right hidden-line view of the distal portion of an exemplary outer cannula. The slot (130) is shown extending to the distal end of the outer cannula (182). An exemplary location of the axle shell (128) is also demonstrated. The axle shell (128) is located on the bottom interior surface of the outer cannula and is on the opposite side of the slot (130). The axle shell can also be located at the distal end of the outer cannula wherein when the door is in an open position, parallel to the longitudinal axis of the outer cannula, the distal end of the door projects beyond the distal end of the outer cannula. The axle shell (128) is hollow with a cylindrical cut away area (188), which permits the cylindrical side portions of the axle (FIG. 5 ELEMENT 260) to insert and rotate freely.

FIG. 7b also shows portions of exemplary interior geometry for an outer cannula. Side guide tracks (148) accommodate the side tracks of the inner drive cannula (FIG. 2k ELEMENT 176). The outer cannula is also shown with a bottom guide track (184) into which the bottom track of the inner drive cannula (FIG. 2k ELEMENT 178) fits.

The box in FIG. 7c shows the distal location on the outer cannula of the front cut-away view shown in FIG. 7d. The outer geometry of this exemplary outer cannula shaft (146) is cylindrical. In alternate embodiments, the outer cannula can be a non-cylindrical shape. An exemplary slot (130) is shown at the top portion of the figure, here comprising less than 50 percent of the outer cannula circumference. Side guide tracks (148), when present, guide the movement of the of the inner drive cannula by rotationally interlocking with the side tracks, while still allowing free longitudinal movement. Likewise, one or more bottom guide tracks (184) of the outer cannula, when present, accomplish the same purpose, guiding the longitudinal movement of the inner drive cannula via its one or more bottom tracks. An axle shell (128) with hollow cut away area (188) is shown with its position opposite the outer cannula slot. Exemplary items (158) demonstrate that the interior surface of the outer cannula can be cut-away, if necessary, to allow for the fit of the door connection system and the adjustable internal door's unobstructed movement. In some embodiments, the distal end of the inner drive cannula can also be cut-away, or have cut-away surfaces, to allow for the fit of the door connection system and the adjustable internal door's unobstructed movement.

The box in FIG. 7e shows the proximal location on the outer cannula of the detailed front view of FIG. 7f. This view corresponds to one obtained by looking distally down the barrel of the outer cannula. In this example, the demonstrated outer cannula geometry could extend from the proximal surface of the outer tube (180) until the beginning of the sift area (130), after which the distal geometry of the outer tube could correspond to geometry that is shown in FIG. 7d. FIG. 7f demonstrates the same optional side and bottom guide tracks for side (148) and bottom (184) tracks on the inner drive cannula. The primary difference between the geometry in FIG. 7d and FIG. 7f is that in FIG. 7f, the top portion of the outer cannula does not include the slot. The exterior top edge of the proximal outer cannula corresponds to the cylindrical shape of the outer cannula shaft (146). The interior geometry of the superior surface of the proximal portion of the outer cannula (168) is the equivalent to the geometry that was dictated by the superior interior surface of the distal portion of the inner drive cannula (FIG. 2k ELEMENT 168). Thus, as an example, the superior interior geometry of the outer tube can approximate the top half of an equivalent cylinder, so that when the inner drive cannula is placed inside of the outer cannula, the combined interior surfaces (168) can comprise a complete cylinder (FIG. 9b).

The outer cannula can be, for example, threaded to accommodate the attachment of a correspondingly threaded outer cannula cover, or handle, as well as other attachments. An exemplary attachment is a steering assembly.

Door Motion in Relation to Cannulas

FIGS. 8a, 8b, and 8c are top right surface views of the inner drive cannula (140), adjustable internal door (104), axle (144), and door connectors (108). The three exemplary views correspond to the relation of the elements when the door is at about 0 degrees, about 45 degrees, and about 90 degrees. The axle (144) is free to rotate but is fixed in the longitudinal direction inside of the axle shell (FIG. 7b ELEMENT 128) located in the outer cannula. As the inner drive cannula is pulled proximally (to the bottom left side of the illustration), the door connectors pull the adjustable internal door at the door hinge holes (152). This longitudinal motion rotates the angle of the door as is shown in FIG. 8a through FIG. 8c. Such longitudinal motion of the superior edge of the adjustable internal door is possible in part because the door connectors are free to rotate in both the hinge holes (154) of the inner drive cannula and door hinge holes (152).

FIGS. 8d, 8e, and 8f are right side hidden line views of the inner drive cannula (140), adjustable internal door (104), axle (144), and door connectors (108). The three exemplary views correspond to the relation of the elements when the door is at about 0 degrees, about 45 degrees, and about 90 degrees. When the distal surface (150) of the inner drive cannula (140) is pulled proximally (away from the distal end of the outer cannula and to the left side of the illustration), force is applied to the adjustable internal door (104), which changes the angle of the adjustable internal door accordingly. The axle (144) is free to rotate but is fixed in the longitudinal direction inside the axle shell (128). That is, although the axle can rotate, its position in relation to the outer cannula does not change.

FIGS. 8g, 8h, and 8i are top right surface views of the outer cannula (146), the slot (138) in the outer cannula, the inner drive cannula (140), adjustable internal door (104), and door connectors (108). The three exemplary views correspond to the relation of the elements when the door is at about 0 degrees, about 45 degrees, and about 90 degrees. The arrows on FIG. 8h and FIG. 8i are shown to indicate the proximal movement of the inner drive cannula in relation to the distal end of the outer cannula as the door angle changes from about 0 degrees (FIG. 8g) to about 90 degrees (FIG. 8i).

Figure 8M:
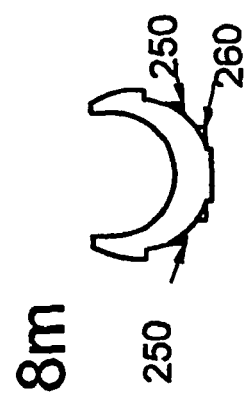
FIG. 8m shows the same embodiment from an end-view, looking down the longitudinal axis from the distal end of the adjustable device delivery system.
Figure 8N:
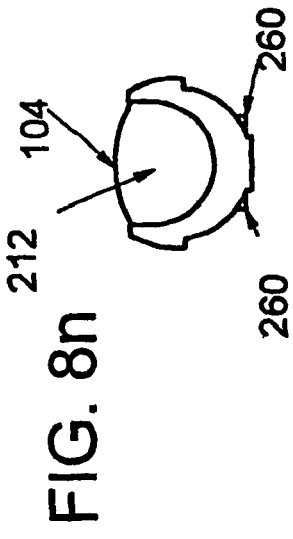
FIG. 8n shows the same embodiment from an end-view, looking down the longitudinal axis from the distal end of the adjustable device delivery system.
Figure 8O:
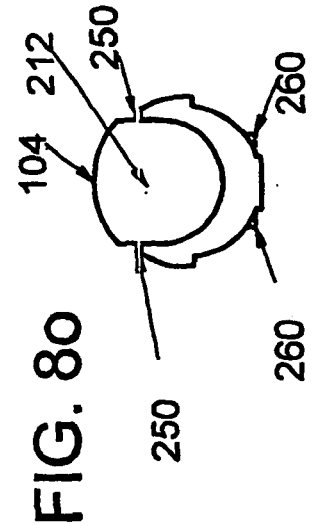
FIG. 8o shows the same embodiment from an end-view, looking down the longitudinal axis from the distal end of the adjustable device delivery system.
Figure 8J:
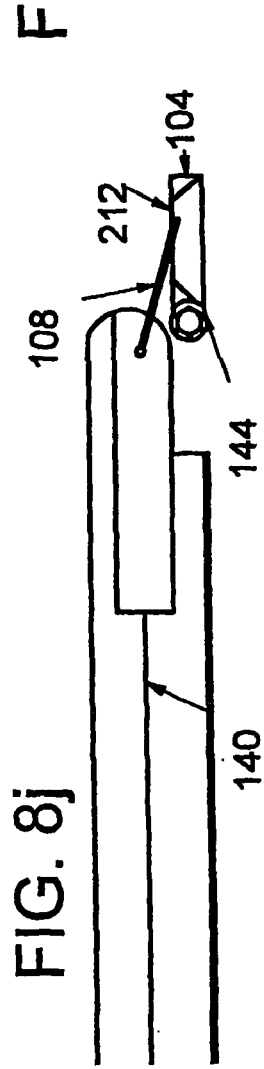
FIG. 8j is a top-right view of an adjustable device delivery system with the adjustable internal door in an open, 0 degree position.
Figure 8K:
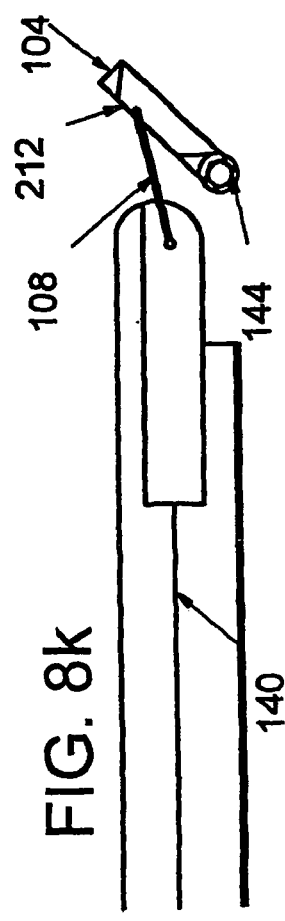
FIG. 8k is a top-right view of an adjustable device delivery system with the adjustable internal door in a partially closed, 45 degree position.
Figure 8L:
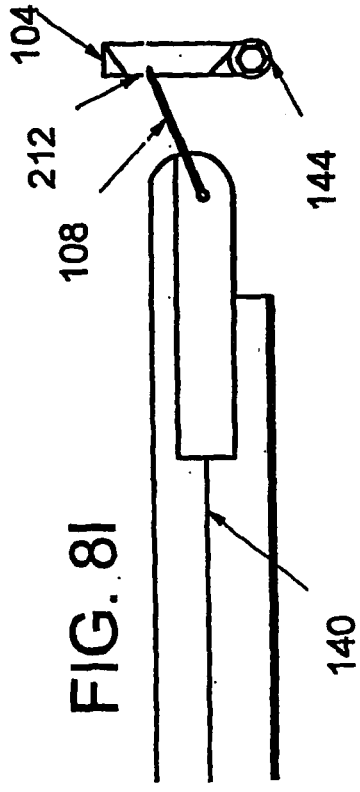
FIG. 8l is a top-right view of an adjustable device delivery system with the adjustable internal door in a closed, 90 degree position.

FIGS. 8j, 8k and 8l are right side views of the inner drive cannula drive (140), adjustable internal door (104), axle (144), and door connectors (108). The position of the adjustable internal door in FIGS. 8j, 8k and 8l corresponds to the position of the door in the longitudinal views of FIGS. 8m, 8n and 8o, respectively. FIGS. 8j, 8k and 8l include exemplary relative positions of the proximal inner drive cannula insertion tabs (FIG. 4a, ELEMENT 254) and distal door insertion tabs of the door connector elements (FIG. 4a; ELEMENT 252). FIGS. 8m, 8n, 8o represent a front view of a cut away portion of the inner drive cannula, looking distally, having a view that would be experienced by a medical or non-medical device passing down the barrel of a adjustable device delivery system of the invention. FIG. 8m shows the door in an open, 0 degree position (i.e., parallel to the longitudinal axis of the outer cannula). In this exemplary embodiment, the path of the medical or non-medical device passing through the adjustable device delivery system would pass to the distal end of the outer cannula unobstructed. FIG. 8n shows the door in an about 45 degree position. In such an instance, the path of the medical or non-medical device passed through the adjustable device delivery system is deflected at about a 45 degree angle from the longitudinal axis of the device delivery system. FIG. 8o shows the door in about a 90 degree position (i.e., perpendicular to the longitudinal axis of the outer cannula). In such an instance, the path of the medical or non-medical device passed through the adjustable device delivery system is deflected at about a right angle from the longitudinal axis of the of the device delivery system.

Door Geometry in Relation to Outer and Inner Drive Cannulas

FIG. 9a is a top right view of the adjustable device delivery system with a box indicating the location of the cut-away view shown in FIG. 9b. FIG. 9b shows an exemplary relationship of the surfaces of the inner drive cannula and the outer cannula. The medical device, non-medical device or EMR passes down the barrel or lumen of the adjustable device delivery system (170) with a path defined by the cylindrical geometry of the superior surface of the inner drive cannula (168) and the exterior inferior surfaces of the outer cannula (168). A side track of the inner drive cannula (176), if present, fits inside the corresponding side guide track of the outer cannula (148). A bottom track of the inner drive cannula (178), if present, fits inside a corresponding bottom guide track (184) of the outer cannula.

FIG. 9c is a top right view of the adjustable device delivery system with a box indicating the location of a cut-away view shown in FIG. 9d. FIG. 9d shows an exemplary fit of the inner drive cannula, outer cannula, and adjustable internal door. Side tracks of the inner drive cannula (176), if present, fit inside correspondingly shaped side guide tracks of the outer cannula (148). Track and guide tracks should be designed to fit together such that the track fits longitudinally into the guide track and allows longitudinal movement of the inner drive cannula within the outer cannula while limiting rotational movement between the inner drive cannula and the outer cannula. The proximal inner drive cannula insertion tab (FIG. 4 ELEMENT 254) of the door connectors (FIG. 8b ELEMENT 108) is generally inserted into the hinge hole (154) of the inner drive cannula. The shaft of the door connector (FIG. 4. ELEMENT 250) connects the hinge hole (154) of the inner catheter and door hinge hole (152). This door connector comprises a shaft (FIG. 4. ELEMENT 250) that fits and preferably moves without binding within the space distal end of the adjustable device delivery system. To facilitate free fit and movement of the door connectors, the door hinge and the adjustable internal door, the inner drive cannula and outer cannula can optionally contain cut-away elements, for example, the optional cutaway portion of the distal inner drive cannula (172) and of the outer cannula (158).

The superior edge of the adjustable internal door (202) in a 90 degree position is shown in FIG. 9d. In this example, the geometry of this superior edge corresponds exactly to the geometry of the interior superior surface of the outer cannula and therefore does not collide with the outer cannula.

FIG. 9e is a top right view of the adjustable device delivery system with a box indicating the location of a cut-away view shown in FIG. 9f. FIG. 9f is similar to FIG. 9d except that the adjustable internal door is shown at an open, 0 degree position. This figure is shown to demonstrate that there preferably is no internal collision between a medical device, non-medical device or EMR placed down the barrel of the adjustable device delivery system when the adjustable internal door is in an open position.

Drive Assembly

FIG. 10a shows a top right hidden-line view of the outer cannula cover, or handle. This exemplary outer cannula cover is a cylindrical tube but can assume any shape. The interior tract (270) has a diameter that corresponds to the outer diameter of the outer cannula and can be threaded so that it can be screwed onto the proximal end of the outer cannula. Alternatively, the outer cannula cover can be bonded to the proximal surface of the outer cannula using and adhesive, for example, epoxy. The proximal end of the outer cannula cover (274) can lie flush with the proximal end of the outer cannula (FIG. 7; ELEMENT 180) or lie in a position proximal or distal to the proximal end of the outer cannula. Preferably, the proximal end of the outer cannula cover lies flush to the proximal end of the outer cannula. The distal edge (272) of the outer cannula cover can assume any shape, and, in this example, it tapers. The proximal end of the outer cannula can include a raised ridge in relation to the diameter of the outer cannula of no outer cannula cover is used. If an outer cannula cover is used, the outer cannula raised ridge can have a smaller or larger radius than the proximal end of the outer cannula cover, but it is preferably of a larger diameter than the outer cannula cover (294). The side view in FIG. 10c best exemplifies an exemplary side ridge elevation. This ridge can serve as a stop for use with a steering system. FIG. 10b is a front, distal view of an outer cannula cover.

FIG. 10d illustrates an exemplary washer that can be placed between the interfaces between the steering assembly and the drive actuator. The inner diameter of this washer, the washer inner-hole diameter, can correspond to the diameter of the drive barrel (FIG. 2b ELEMENT 166) if the drive barrel is of a smaller diameter than the drive shaft. In an alternate embodiment where the drive actuator drive shaft is of a smaller diameter than the drive barrel, the washer inner-hole diameter can correspond to the diameter of the drive shaft. One or more of these washers can be used. Where two washers are utilized, the proximal washer can lie flush to the proximal surface (FIG. 2b ELEMENT 162) defined by the differential radii of the drive shaft and drive barrel and the distal washer can lie flush to distal surface (FIG. 2b ELEMENT 164) defined by the differential radii of the drive shaft and drive barrel. Alternatively, no washers can be used. FIG. 10e shows a washer that can be placed between the raised ridge of the outer cannula (FIG. 10a ELEMENT 274) and the steering system (FIG. 11f; 120).

FIG. 11a is a top right view of the outer cannula (146), inner drive cannula (140) and outer cannula cover (112), with a box indicating the items that are shown in detail in FIG. 11b. Item (274) is an outer cannula raised ridge. The proximal end of the outer cannula (FIG. 7 ELEMENT 180) and the proximal face of the outer cannula cover (274), if present, preferably lie flush at location (290). A portion of the inner drive cannula shaft (140), i.e., the drive actuator, itself comprising a drive barrel (166) and drive shaft (142) and, optionally one or more washers, extends proximally from the proximal end of the outer cannula. Optionally, one or more intermediate elements can between the drive actuator and the inner drive cannula.

FIG. 11c is a top view of the outer cannula (146), inner drive cannula (140), and outer cannula cover (112), with a box illustrating the items that are shown in detail in FIG. 11d. FIG. 11d is a right side hidden-line view of an outer cannula, an inner drive cannula, and outer cannula cover. The locations of the optional washers (114) are demonstrated flush to the proximal (162) and distal (164) surfaces of the drive shaft (142). Alternatively, the drive shaft can be of a smaller diameter than the drive barrel. Washers, if included in such an embodiment, could still be placed flush to the proximal and distal surfaces of the drive shaft. An optional washer (116) is shown butting against, or resting against in contact with, the outer cannula and outer cannula cover with the distal face of the washer flush to the proximal face of the outer cannula and outer cannula cover (274).

Steering Assembly

FIG. 11e is a side view of the outer cannula (146), inner drive cannula (140), outer cannula cover (112), optional washers (114, 116), and a cut away side view of the steering assembly (120) with a box indicating the area shown in detail in FIG. 11f. FIG. 11f shows an exemplary alignment of a cutaway portion of the steering assembly (120) and its interaction with the drive actuator. A drive barrel (166) fits into a center shaft (284) in the steering system, which is cut out and extends the length of the steering assembly. Optional washers (114), which are aligned with the proximal and distal faces of the drive shaft (142), each fit into cylindrical slots (280) in the steering assembly. These washers are comprised of a circular element, with an outside diameter, and a circular hole in the middle defining a washer inner-hole diameter. The washer inner-hole diameter is sized to fit over the steering actuator cylindrical drive barrel or drive shaft, depending on which is larger as described above. Where washers are not used, the cylindrical slots in the steering assembly need not be present.

An outer cannula cover washer (116) can fit into another slot (282). The diameter of the drive shaft (142) fits into the cylindrical cutout area of the steering apparatus (286). A cylindrical steering system cut out area (288) in the distal portion of the steering system fits the diameter of the outer cannula cover (294) if such cover is used. Where no outer cannula cover or outer cannula cover washer is used, the slot (282) will fit a raised ridge on the proximal end of the outer cannula, and the cylindrical steering system cut out area (288) in the distal portion of the steering system fits the diameter of the outer cannula. In either type of embodiment, the outer cannula or outer cannula cover can be threaded, and the distal end of the steering assembly can be correspondingly threaded, wherein the longitudinal motion of the steering assembly can be controlled by turning the steering assembly clockwise and counter-clockwise. The steering assembly itself can be comprised of one or more pieces.

The steering assembly and the drive actuator, and hence the inner drive cannula, move together along the longitudinal axis of the adjustable device delivery system due to the close fit of the steering assembly and the drive actuator as exemplified in FIG. 11f and FIG. 11g. The steering assembly can move longitudinally with respect to the outer cannula due, in this figure, to the correspondingly threaded surfaces of the outer cannula cover and the steering assembly. Thus, rotational movement of the steering assembly translates into longitudinal movement of the steering assembly with respect to the outer cannula. Due to the close connectivity of the steering assembly and the drive actuator, longitudinal movement of the steering assembly translates into longitudinal movement of the drive actuator. As the drive actuator, in this exemplary embodiment, comprises the proximal end of the inner drive cannula, the longitudinal movement of the drive actuator generates equivalent longitudinal movement in the inner drive cannula.

In other embodiments, the drive actuator does not directly comprise the proximal end of the inner drive cannula but can interact with the inner drive cannula indirectly, through one or more intermediate elements. For example, the drive actuator and inner drive cannula can interact through a set of gears to increase or decrease the longitudinal movement of the steering assembly or through a compressible member, like an elastomer, to elastically transmit the longitudinal force of the steering assembly to the adjustable internal door at the distal end of the inner drive cannula. Movement of the inner drive cannula then translates into rotational movement of the adjustable internal door, the door rotating along the axle axis, via its connection to the door with one or more door connectors.

In addition, more traditional wire or ribbon-based systems, similar to those used to steer steerable catheter systems (for example, see U.S. Pat. No. 6,530,914), are contemplated for door movement. For example, one or more manipulation members can attach to the side surfaces of the adjustable internal door, which members can run proximally from the adjustable internal door, through the lumen of the adjustable device delivery system to the proximal end, where the user can adjust the angle of the door by exerting pulling or pushing forces on the manipulation member. Alternatively, the one or more manipulation member can reside in one or more lumen separate from the lumen through which the medical device, non-medical device or EMR is delivered.

Still further, embodiments that utilize one or more inflatable members, such as a balloon, for door movement are contemplated. For example, a balloon with a first and second attachment surface can attached to the adjustable device delivery system of the invention, the first attachment surface connected to the distal face of the adjustable internal door and the second attachment surface connected to the distal end of the outer cannula opposite the slot. The balloon can inflatably move the door from an open position (i.e., door body parallel to the longitudinal axis of the outer cannula) to a closed position (i.e., door body perpendicular to the longitudinal axis of the outer cannula) through inflation and deflation of the balloon. The balloon can be inflated and deflated by one or more inflators/deflators, for example, air pumps, fluid pumps, syringes, and the like, that can reside within or, preferably, without the adjustable device delivery system of the invention. The one or more inflators/deflators can attach to the one or more inflatable members through one or more inflation/deflation connectors, which inflation/deflation connectors can run proximally from the one or more inflatable members, through the lumen of the adjustable device delivery system to the proximal end, or where the one or more inflators/deflators reside, where the user can adjust the angle of the door by inflating or deflating the one or more inflatable members utilizing the one or more inflators/deflators. Alternatively, the one or more inflation/deflation connectors can connect the inflatable member to the one or more inflators/deflators through one or more lumen separate from the lumen through which the medical device, non-medical device or EMR is delivered.

FIG. 12a is a top right view of the adjustable device delivery system with the box indicating the area, which is shown in detail in FIG. 12b. FIG. 12b is a top right hidden-line view of a complete exemplary steering assembly. The steering shaft (284) can be the same diameter as the drive barrel of the inner drive cannula (FIG. 11f ELEMENT 166). The cut-out area (FIG. 11f ELEMENT 286) allows the assembly to fit over the drive shaft (FIG. 11f ELEMENT 142). A cylindrical steering system cut out area (288) fits over the shaft of the outer cannula cover (FIG. 11f ELEMENT 294), if used, or over the outer cannula if no outer cannula cover is used. The cylindrical slots (280) that accommodate the washers (FIG. 11f ELEMENT 114) that are flush with the drive shaft (FIG. 11f ELEMENT 142) are demonstrated. Another slot (282) that can accommodate a washer (FIG. 11f ELEMENT 116) that can lie flush with the outer catheter cover (FIG. 11f ELEMENT 294), if used, or over the outer cannula if no outer cannula cover is used, is also demonstrated.

The steering assembly is free to rotate clockwise and counter-clockwise around the longitudinal axis of the adjustable device delivery system. The distal portion of the steering assembly (288), which is preferably of a complementary size to the surfaces of the outer cannula cover (294), if used, or the outer cannula, is preferably threaded to match threads on the outer cannula cover or outer cannula. Consequently, rotational motion of the steering assembly translates into proximal and distal translation of the steering assembly in relation to the outer cannula cover and/or outer cannula. Because the inner drive cannula is fixed in relative position with the drive actuator, the drive actuator and inner drive cannula move longitudinally along with the steering assembly. The drive actuator and inner drive cannula can be directly connected, the drive actuator comprising the proximal end of the inner drive cannula, or, as mentioned above, the drive actuator can be indirectly associated with the inner drive cannula. Washers, if present, preferably prevent unwanted torque between the inner and outer cannulas.

FIG. 12c is a top right view of the adjustable device delivery system with the box indicating the area that is shown in detail in FIG. 12d. In embodiments that comprise complementary-threaded surfaces on the outer cannula or outer cannula cover and the steering assembly allow for the longitudinal movement of the drive actuator, inner drive cannula and adjustable internal door by rotating the steering assembly in either a clockwise or counter-clockwise direction depending on the configuration of the threaded surfaces. When an outer cannula cover is present, the outer cannula is generally fixed inside the outer cannula cover. The inner drive cannula, and associated drive actuator, is fixed in relative position to the steering assembly. Therefore, proximal motion of the steering assembly causes proximal motion of the inner drive cannula in relation to the outer cannula. Continued proximal motion ultimately causes the adjustable internal door to be pulled closed to angle approaching, and in some embodiments surpassing, 90 degrees. Once again, in embodiments where clockwise rotation of the steering assembly translates into distal movement of the adjustable internal door, counter-clockwise rotation will result in proximal translation of the adjustable internal door. Controlled longitudinal movement can be accomplished in some embodiments that lack threaded surfaces on the outer cannula or outer cannula cover and the steering assembly. For example, a friction-based mechanism can control longitudinal motion of the drive actuator, inner drive cannula and internal adjustable door.

FIG. 12e and FIG. 12f illustrate an exemplary lock system and steering assembly showing possible relative position of the steering assembly to the lock assembly. In this example, an outer cannula cover is present. FIG. 12e demonstrates the relative positions of a lock system and a steering assembly when the adjustable device delivery system has an adjustable internal door open at about 0 degrees. When the adjustable internal door is open, the inner drive cannula is located at its most distal position in relation to the outer drive cannula. This open position for the adjustable internal door allows maximum space (402) inside the steering apparatus (120) between the distal end of the steering assembly slot (FIG. 11f; ELEMENT 282) and the proximal end of the outer cannula and/or outer cannula cover. The open position also yields a smaller amount of space (400) between the steering apparatus (120) and lock apparatus (122). In contrast, when the adjustable internal door is to be closed to any angle, the inner drive cannula must move in a proximal direction in relation to the outer cannula. Rotation of the steering assembly in a clockwise or counter-clockwise direction, again depending on the orientation or polarity of the threads, can move the steering assembly proximally, away from the distal end of the outer cannula. Such movement increases the distance (400) between the steering assembly (120) and the lock system (122). Closing the adjustable internal door (i.e., changing the angle of the door to about 90 degrees in relation to the longitudinal axis of the adjustable device delivery system), allows minimum space (402) inside the steering apparatus (120) between the distal end of the steering assembly slot (FIG. 11f; ELEMENT 282) and the proximal end of the outer cannula and/or outer cannula cover. In alternate embodiments, the steering assembly and the lock system can interact with the outer surface of the outer cannula or, if present, the outer surface of an outer cannula cover, in a non-threaded manner. For example, the lock could operate with a simple friction fit wherein the lock system moves on the outer cannula or outer cannula cover with resistance, such that moving the lock adjacent to or abutting the steering assembly provides resistance to steering assembly movement.

Lock Motion

FIG. 12g is similar to FIG. 12f in that it illustrates the adjustable device delivery system with the adjustable internal door closed to a maximum angle with attention placed on the steering assembly (120) and locking system (122). The steering assembly is unlocked in FIG. 12g. When the lock is moved proximally, or to the left in this Figure, it ultimately collides with the steering assembly and locks it in place, preventing movement of the steering assembly (FIG. 12h). Unlocking the apparatus is achieved by moving the locking system distally so that it is no longer in contact with the steering assembly, thus freeing the steering assembly for movement of the adjustable internal door. Again, the lock can be moved via threads on the outer cannula or outer cannula cover and complementary threads on the interior surface of the lock system, or by other methods such as friction fit, as described above.

Outer Cannula Cover

A box illustrates the location of the optional outer cannula cover and separate handle in relation to the adjustable device delivery system in FIG. 13a. When present, an outer cannula cover can act as a handle for the user. When not present, the surface of the outer cannula can serve as a handle for the use. FIG. 13b shows a handle separate from an outer cannula cover. The inner circumference of the handle should correspond to the outer diameter of the outer cannula cover (FIG. 10a, ELEMENT 294). A separate handle can be attached as described above, namely with a threaded interior surface that complements a correspondingly threaded outer surface of an outer cannula cover or, for example, with an adhesive like epoxy.

Lock

FIG. 14a shows the adjustable device delivery system with a box around the lock system. FIG. 14b is a face view of the lock system. The apparatus can be, for example, a hexagonal nut with beveled edges. The inner circumference of the lock system preferably has an inner diameter that corresponds to the outer diameter of the outer cannula cover (FIG. 10a, ELEMENT 294), if present, or the outer diameter of the outer cannula. The interior surface of the lock system and outer cannula or outer cannula cover can be complementarily threaded so that the lock can rotate clockwise and counter-clockwise in relation to the outer cannula cover, if present, or the outer cannula, locking and unlocking the steering assembly accordingly.

DESCRIPTION OF PREFERRED USES

The adjustable device delivery system has many applications in biological or medical fields. Uses in interventional radiology and endovascular surgery include: creation of arterial/venous fistula, stenting of arteries and veins which are located at angles, including right angles, angioplasty at angles, including right angles, and drainage of various collections. The adjustable device delivery systems of the invention would also advance and facilitate existing techniques of TIPS (transjugular intrahepatic portosystemic shunt). Uses for cardiologists include the angled placement of pacing wires, angioplasty of vessels, formation of fistulas, and stenting of the coronary sinus into the left ventricle. Urologic uses include prostate biopsy, drainage of collections along the urethra as well as biopsy and manipulation of low-lying bladder lesions difficult to reach with traditional devices. Colorectal uses include the drainage of ischiorectal abscesses as well as drainage and or/biopsy of other collections located along the gastrointestinal tract that could not be easily achieved by colonoscopy. Gastrology uses for the device include transgastric drainage of collections such as pancreatic pseudocysts as well as other collections along the GI tract. Pulmonologists could use the device to aid biopsy during bronchoscopy.

Additional uses for the devices of the invention not explicitly recited herein will be evident to those having skill in this art.

The adjustable device delivery systems of the invention are not useful only for deflecting stents and needles but also have the ability to deflect electromagnetic waves used in visualization devices. These electromagnetic waves could represent acoustic, optic, or other radiation devices used to visualize a target. For these uses, the invention provides embodiments of the devices disclosed herein having an adjustable internal door that is either be made of any combination of corresponding reflective materials or coated with such materials.

An example of such an embodiment is placement of an intravascular ultrasound device down the barrel of the adjustable device delivery system (170). The operator advances the distal tip of the visualization device (304) to a point just proximal to the axle of the adjustable internal door (260). The acoustic waves projected from the tip of the ultrasound (306) bounce off of the proximal reflective surface of the adjustable internal door (212) at the desired angle set by the operator. The electromagnetic waves returning from the target are deflected by the adjustable internal door as well back into the tip of the visualization device.

Thus, the adjustable device delivery system can function as a visualization control system for technology placed down its lumen. The reflective surface of the adjustable internal door does not need to be limited to acoustic devices such as ultrasound. In other embodiments, the adjustable internal door can be coated with an optical reflective surface such as a mirror. Reflective surfaces can be combined when necessary and adapted to new forms of radiation visualization technology.

The reflective surface of the adjustable internal door does not have to be limited to visualization technology. Any device that relies on electromagnetic radiation can be deflected with the adjustable internal door; examples include laser and radiation devices used to cut and coagulate tissue. In further embodiments, the surface of the adjustable internal door can be shaped in such a manner as to facilitate focusing of these various forms of electromagnetic radiation.

The adjustable device delivery system can also be used to perform tissue biopsies at user-defined and adjustable angles to aid in various forms of cancer diagnosis and treatment. An example is the use of the adjustable device delivery system to perform prostate biopsy. After lung cancer, prostate cancer accounts for more cancer deaths in men than any other cancer. The prostate lies at a right angle to the prostatic urethra. Although existing devices can be passed up and into the urethra, the angle of the prostate makes an adequate transurethral biopsy difficult. By providing a method to perform visualization and instrumentation, or the delivery of devices, at various, user-defined angles, the adjustable device delivery system can be advantageously used.

The use of the present invention to perform a less invasive form of cancer biopsy may increase the likelihood that males seek both screening and diagnostic procedures. The potential for increased biopsy accuracy with the present invention can allow for a higher percentage of accurate tumor samples. Increased biopsy accuracy would decrease the need for repeat procedures and, consequently, speed the time to diagnosis and definitive treatment.

Moreover, the use of the device deflection system could be used in combination with existing cancer treatments. Lasers or various forms of radiation or other energy sources can be deflected off the door at adjustable angles. Tumor cells are thus fulgurated and/or ablated in a more controlled manner with less damage to surrounding healthy tissue. Protection of healthy tissue around the prostate is paramount given the number of surrounding nerves and vital structures. The possibilities of more accurate and efficient therapies might decrease impotence and other debilitating side-effects from current treatments for the more advanced stages of prostate cancer.

These examples refer to just some of the applications of the adjustable device delivery system; these examples are not intended to be limiting, and those with skill in the art would recognize multiple other possibilities and uses for this device. For example, the device could be placed down the lumen of a tube with a camera passed down the barrel of the instrument, and the camera would permit direct visualization as the instrument was placed into position. Alternatively, a device such as a colonoscope could be passed down the barrel of a larger version of the device. The operator controlling the inserting colonoscope would also control the path of the adjustable device delivery system. Therefore, once the colonoscope indicated that the device was in proper position, the colonoscope could be removed and instrumentation could follow.

Embodiments wherein the door is located at the distal end of the outer cannula and wherein said door extends beyond the distal end of the outer cannula when in its open position (i.e., the door is parallel to the longitudinal axis of the outer cannula), are particularly well suited to be used as a steering device for placement of, for example, a guidewire. That is, the catheter delivery system can not only be used to deliver a device (here, a guidewire) at a user-defined angle, as described elsewhere herein, but a guidewire delivered at a user defined angle can then be used to steer adjustable device delivery system itself along the guidewire path. For example, the adjustable device delivery system can be placed in, for example, a blood vessel lumen, and a guidewire can be advanced through the lumen of the adjustable device delivery system and deflected at a user-defined angle to a target area. After the guidewire has been delivered to (or toward) a target area, the adjustable device delivery system can then be advanced along the length of the guidewire. That is, the adjustable device delivery system of the invention is used to steer a guidewire in a particular direction through deflection of the guidewire off of the adjustable internal door at a user-defined angle. The adjustable device delivery system is then advanced along the user-defined path of the guidewire to a new position. This process can be repeated as necessary, and such iterative, repeated placement of the guidewire at user-defined angles and similar advances of the device delivery system along the path of the guidewire effectively steers the guidewire and adjustable device delivery system along any user-defined path, for example, through a maze of blood vessels, such as is found in interventional cardiology. Placement of the adjustable internal door at the distal end of the outer cannula wherein the door extends beyond the distal end of the outer cannula when in its open position facilitates steering of the adjustable device delivery system due to a lack of extraneous outer cannula distal to the adjustable internal door that could hinder advancement along the guidewire in confined spaces. The adjustable internal door can be in an open, closed or intermediate position while advancing the adjustable device delivery system along a guidewire.

The adjustable device delivery system of this invention is also relevant in non-biological procedures. For example, the adjustable device delivery system of the invention would function to deliver a device to an area of limited access, for example, to place a wire or pipe at an angle in a narrow space. Such uses make the present invention important, inter alia, in automobile assembly as well as other mechanized assembly lines.

With respect to the above uses for the adjustable device delivery systems of the invention, the outer cannula is designed in close relation to the inner drive cannula, the geometry of the outer cannula generally comprising a cylindrical tube with a radius that is determined by the size of the device being delivered. For example, if construction for angioplasty is desired, a suitable size for the outer cannula would be approximately 7F, or 7 French. For other uses, such as, for example, device delivery in the gastrointestinal system or in non-medical pipes or conduits, a much larger size can potentially be used. The outer cannula and inner drive cannula can be made of any suitable material whether rigid or flexible.

One application of the use of the devices of the invention, specifically as operated in blood vessels is as follows. A small incision is made in the skin or a vessel located and entered percutaneously. A guidewire is placed down a vessel lumen. The incision is expanded using dilators so that adjustable device delivery system could be slid down the guidewire with the adjustable internal door in the open position. The adjustable device delivery system and its adjustable internal door is slid to the estimated desired position guided by external or internal visualization techniques including fluoroscopy and ultrasound.

Once the adjustable device delivery system is placed in the correct location, the guidewire is withdrawn. An intravascular ultrasound or other imaging device is fed down the lumen of the adjustable device delivery system with the adjustable internal door in the open position. When, for example, the distal tip of the intravascular ultrasound approached the adjustable internal door, the operator turns the handle of the steering assembly in the proper direction to close the adjustable internal door to the desired angle.

Once the adjustable internal door is closed to the desired degree and the target collection or vessel is identified by the distal tip of the intravascular ultrasound, the operator then locks the angle of the adjustable internal door with the lock system, for example, by butting the lock system against the steering assembly so that the steering assembly cannot move.

The intravascular ultrasound or visualizing apparatus is then removed. The operator then slides the desired medical or non-medical device down the adjustable device delivery system. Because the adjustable internal door has been locked in position and because of the difficulties in overcoming the inherent frictional forces in the steering assembly, the adjustable internal door preferably does not move between instrument changes. When the medical device reaches the door, it is deflected at the same angle previously selected by intravascular ultrasound or external visualization techniques.

Another advantageous use for the devices of the invention is for guiding a needle meant to penetrate a cavity located at an angle to a vessel or lumen housing the adjustable device delivery system. When the needle hits the door, it is deflected at the desired angle. The needle path is visualized by external techniques such as fluoroscopy or internal techniques if, in this example, the needle and a visualization device like an intravascular ultrasound can both be delivered to the area of interest simultaneously. When the needle penetrates the desired lumen or space, further devices can be delivered with the adjustable internal door in the same locked position.

A drainage catheter can then be slid in standard Seldinger technique so that it follows the same pathway as the needle and enters the same lumen or space. The needle could then be withdrawn.

The adjustable device delivery system is then unlocked by moving the locking mechanism away from the steering assembly. The adjustable internal door is opened by turning the steering mechanism in the opposite direction of that described above to close the adjustable internal door. Such movement of the steering assembly causes the internal drive cannula to be pushed distally into the outer cannula, whereupon the one or more door connectors would push on the adjustable internal door until it swung distally and was once again in an open 0 degree position.

The catheter is then removed from the body by pulling the entire apparatus proximally. No external collision between the angled stent and the body of the adjustable device delivery system occurs because of the cut-away slot in the distal portion of the outer cannula that extends to the distal end of the outer cannula. Because the adjustable internal door was fully opened before removal of the device delivery system, and consequently was not in the pathway of the stent, there is no collision between the adjustable device delivery system and the stent, which allows the stent to retain its angle of delivery.

Methods

The invention also provides methods for delivering a medical device, a non-medical device, including without limitation those described above, or EMR to an confined space. Such methods can be accomplished by inserting the adjustable device delivery system into a confined space, for example, through an incision in a biological system. Once inserted, the adjustable device delivery system is guided to the location of interest, or a delivery location, in the confined space. Once inserted, the adjustable device delivery system can be oriented such that the slot in the distal end of the outer cannula faces the desired delivery location. The orientation step can be performed before an attempt at guiding the adjustable device delivery system to the delivery location is made, especially if an internal visualization device is used to guide the delivery system. The adjustable internal door is then adjusted to a user-defined angle for delivery of the visualization or other device. One or a plurality of medical devices, non-medical devices or EMR can then be delivered to the delivery location through the lumen of the adjustable device delivery system tubular body in a proximal to distal direction, wherein the device is deflected off of the adjustable internal door at about the user-defined angle of the adjustable internal door. Once delivered, the device is utilized in its conventional manner at the delivery location. This method can optionally comprise the step of removing the device delivery system from the confined space with the device remaining within the confined space or removing the device from the confined space along with the device delivery system.

The invention also provides methods for deploying one or a plurality of medical devices at a user-defined angle. Such methods can be accomplished by inserting an adjustable device delivery system of the invention into a space that is connected or proximal to a location where the user desires to deliver the medical device, or medical device delivery location. Once inserted, the adjustable device delivery system is guided to the medical device delivery location within or proximal to the space. Once inserted, the adjustable device delivery system can be oriented such that the slot in the distal end of the outer cannula faces the desired direction of medical device deployment. The orientation step can performed before an attempt at guiding the adjustable device delivery system to the medical device delivery location is made, especially if an internal visualization device is used to guide the delivery system. The adjustable internal door is then adjusted to a user-defined angle for delivery of the medical device, which is then delivered to the delivery location through the lumen of the adjustable device delivery system tubular body in a proximal to distal direction, such that the medical device is deflected off of the adjustable internal door at about the user-defined angle of the adjustable internal door. The medical device is then utilized in its intended manner at the medical device delivery location, for example, a intravascular ultrasound is used for visualization or catheter is used to drain an abscess. These methods of the invention can further comprise the step of removing the device delivery system from the medical device delivery location leaving the medical device behind within the delivery location. In such a medical device delivery method, the angle of delivery of the medical device is not altered due to presence of the slot in the distal portion of the tubular body through which the medical device can slide during removal of the device delivery system.

The invention also provides methods for forming a pathway between bodily compartments. Such methods comprise the step of inserting the adjustable device delivery system of the invention into a first space that is proximal to a second space into which the pathway is to be formed. The adjustable device delivery system is then guided to a bodily compartment connection location within the first space, that is, the location where the connection between the two body compartments is to be made. Once inserted, the adjustable device delivery system can be oriented such that the slot in the distal end of the outer cannula faces the bodily compartment connection location. The orientation step can be performed before the step of guiding the adjustable device delivery system to the bodily compartment connection location, especially if an internal visualization device is used to guide the delivery system. The adjustable internal door is then adjusted to a user-defined angle for delivery of a device that can form a pathway between bodily compartments. Said device is then delivered to the bodily compartment connection location through the lumen of the tubular body of the adjustable device delivery system in a proximal to distal direction, wherein the device is deflected off the adjustable internal door at the user-defined angle of the adjustable internal door. Once delivered, the device that can form a pathway between bodily compartments is used to form the pathway between bodily compartments.

The invention also provides methods for visualization in an confined space. Such methods are accomplished by inserting an adjustable device delivery system of the invention, particularly one with an adjustable internal door made from or coated with a material reflective for various forms of EMR, into the confined space. Once inserted, the adjustable device delivery system is guided to a visualization location, or the location the user wishes to visualize using the methods of the invention, in the confined space. Once positioned at the visualization location, the adjustable device delivery system is oriented such that the slot in the distal end of the outer cannula faces the desired visualization location. The orientation step can be performed before the adjustable device delivery system is guided to the visualization location. The adjustable internal door is then adjusted by moving the device in a proximal-to-distal direction from the adjustable device delivery system to the visualization location (and, optionally, back from the visualization location in a distal-to-proximal direction through the device delivery system) to a user-defined angle to permit deflection of electromagnetic radiation. The EMR can then be delivered in a proximal-to-distal direction from the adjustable device delivery system to the visualization location such that the electromagnetic radiation is deflected off of the adjustable internal door at the user-defined angle of the adjustable internal door. These methods of this aspect of the invention can further comprise the step of detecting electromagnetic radiation deflected off of the adjustable internal door in the opposite direction as during EMR emission, wherein such electromagnetic radiation moves in a distal-to-proximal direction in the adjustable device delivery system.

The invention also provides methods for delivering focused electromagnetic radiation in a confined space. Such methods can be accomplished by inserting an adjustable device delivery system wherein the adjustable internal door can deflect electromagnetic radiation into the confined space. Once inserted, the adjustable device delivery system having a reflective door is guided to an electromagnetic radiation target location in the confined space, and the adjustable device delivery system is oriented such that the slot in the distal end of the outer cannula faces the desired electromagnetic radiation target location. The orientation step can be performed before the adjustable device delivery system is guided to the visualization location The adjustable internal door is then adjusted to a user-defined angle by moving the device in a proximal-to-distal direction from the adjustable device delivery system, thereby permitting delivery of focused of electromagnetic radiation to the electromagnetic radiation target location. Finally, the EMR is delivered in a proximal-to-distal direction from the adjustable device delivery system to the electromagnetic radiation target location such that the electromagnetic radiation is focused by the adjustable internal door and deflected at the user-defined angle of the adjustable internal door to the electromagnetic radiation target location.

In all of the above aspects of the invention, the device delivered by the adjustable device delivery system can be a medical or non-medical device. Further, the location to which a medical or non-medical device is delivered can be in a biological or non-biological system.

The following Examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

Example 1

FIGS. 15a through 15m outline the use of the device for placement of a stent between two neighboring blood vessels. In each of FIGS. 15a through 15m, element 302 is the outline of the entry vessel down which the adjustable device delivery system is percutaneously delivered and element 304 represents a target vessel.

Figure 15A:
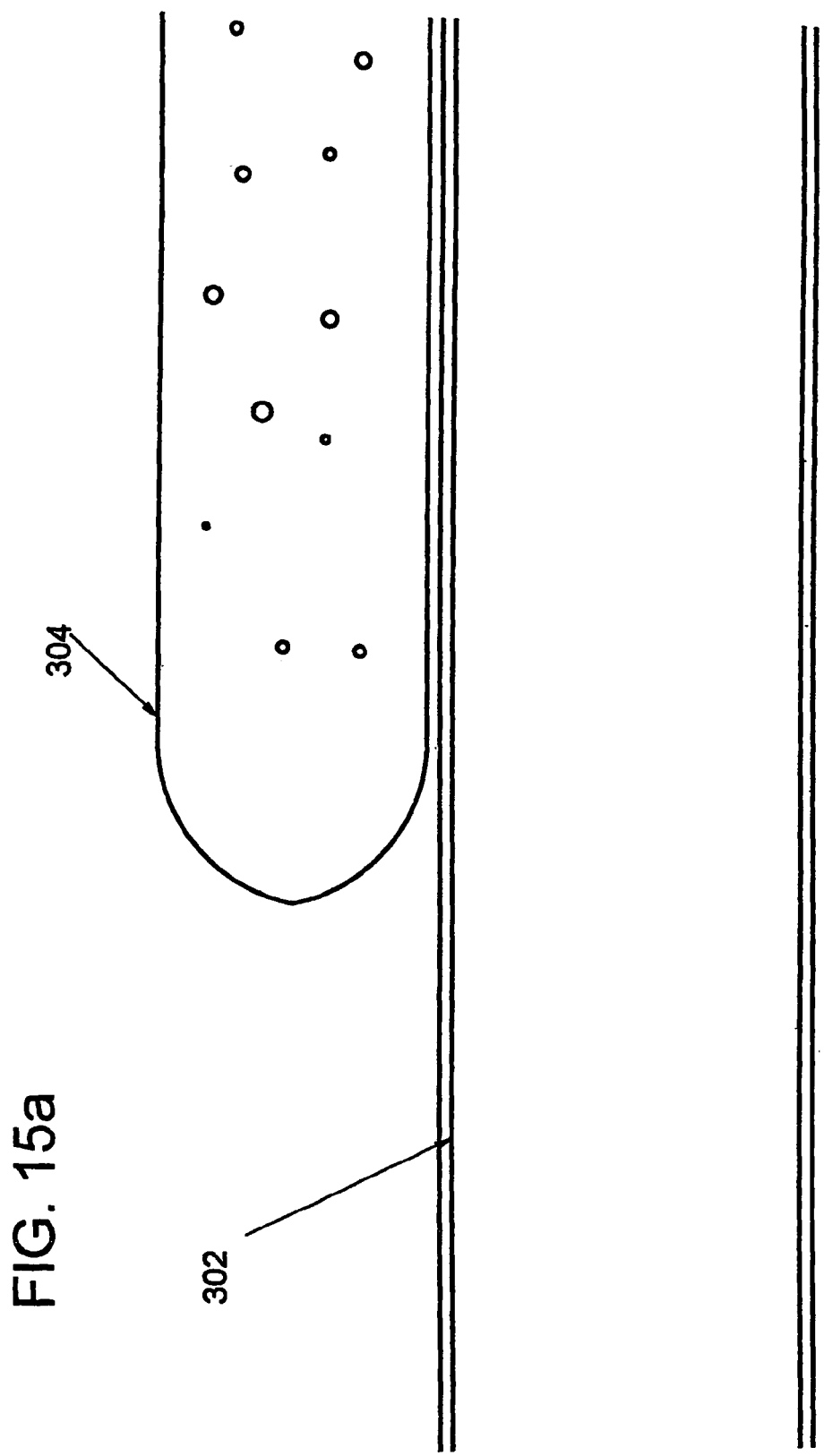
FIG. 15a is a view of a vessel and a collection in need of draining located superior to the vessel and at an angle to the vessel lumen.
Figure 15B:
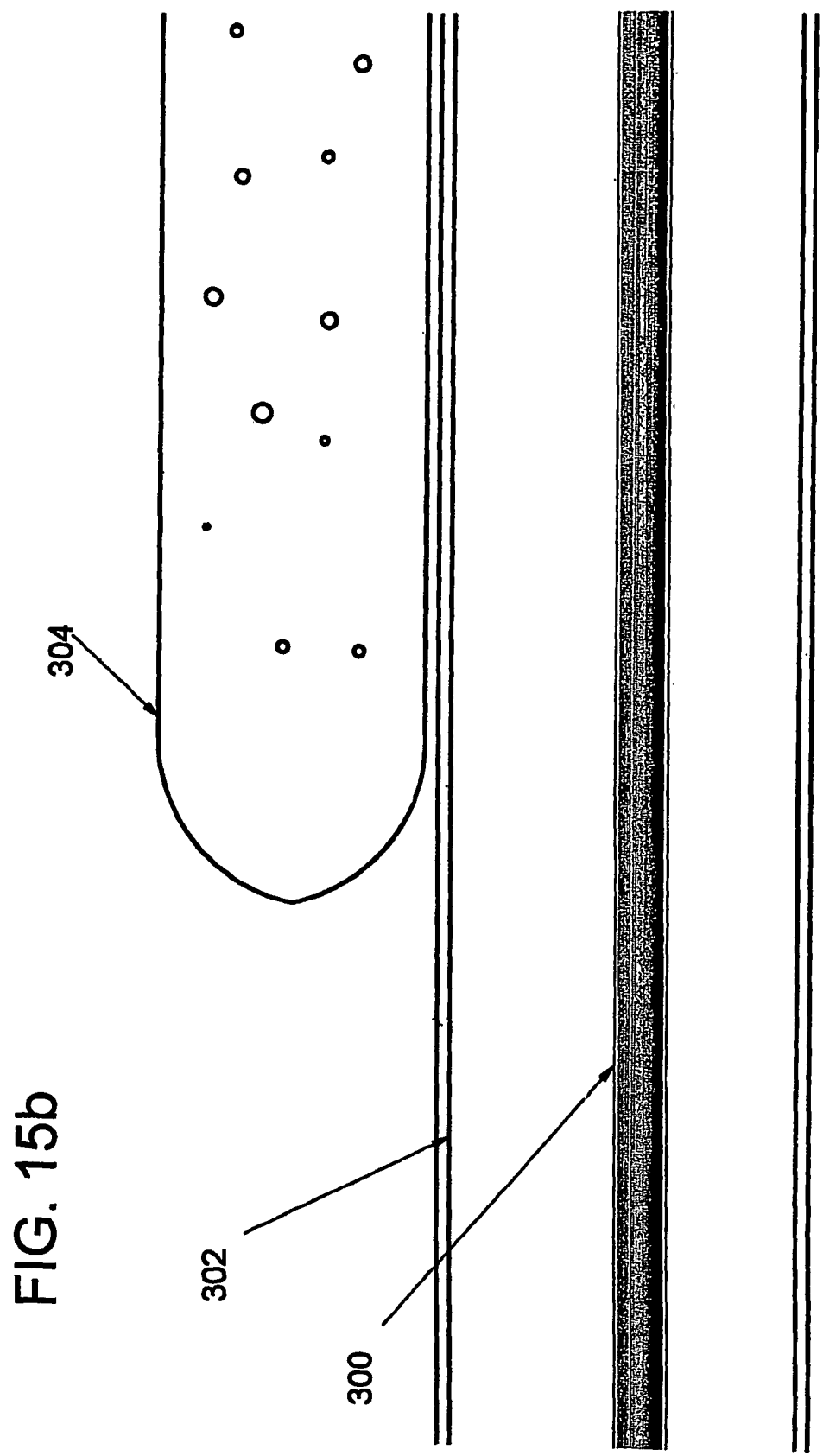
FIG. 15b shows a guidewire placed down the vessel lumen.
Figure 15C:
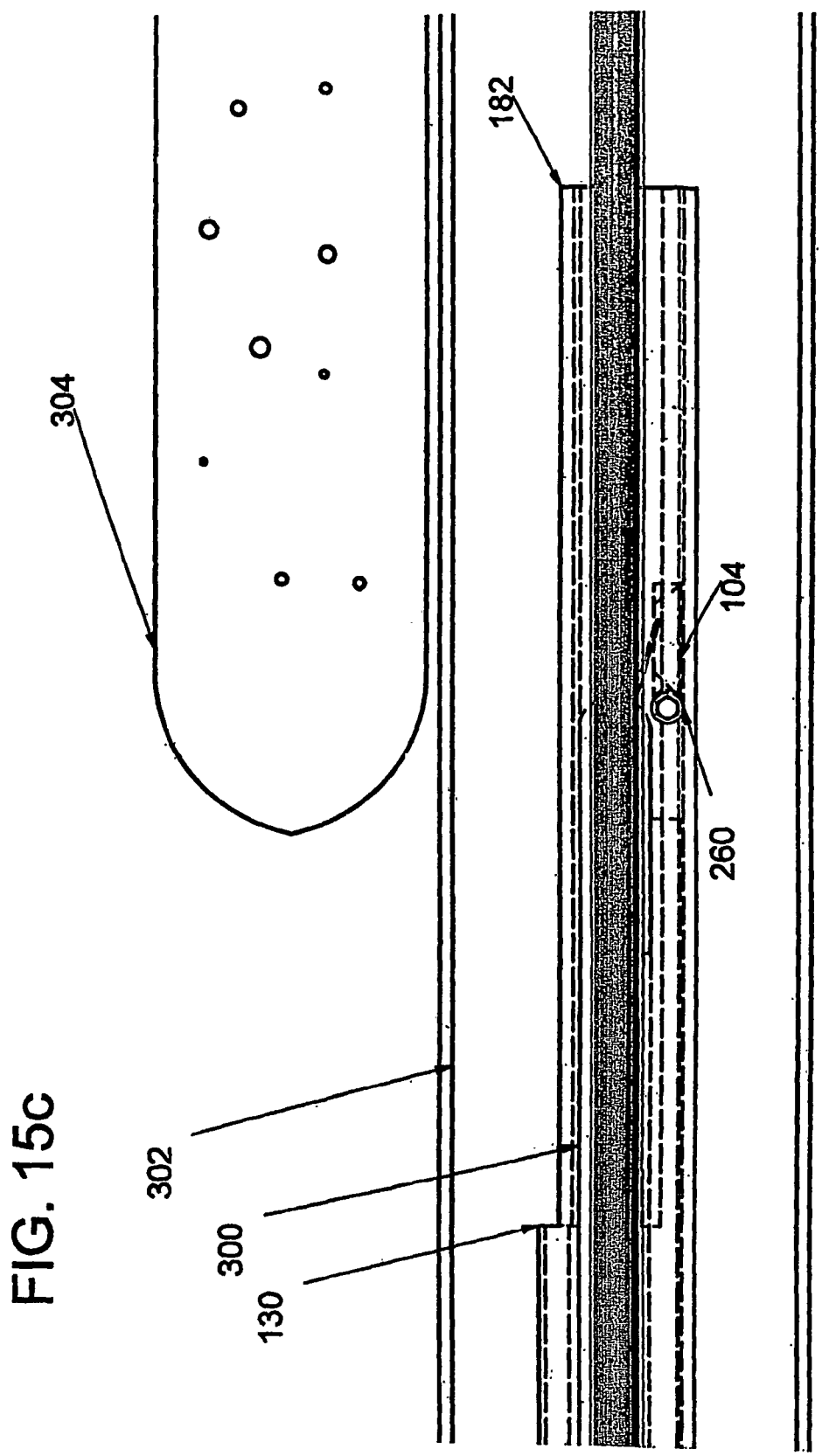
FIG. 15c shows the adjustable device delivery system slid into position next to the collection using the guidewire, with the adjustable internal door in an open position.

FIG. 15a demonstrates the native position of these two vessels. A guidewire can be percutaneously placed down a target vessel using, for example, techniques of external visualization like fluoroscopy. FIG. 15b shows such a guidewire (300) passing down the lumen of the entry vessel (302) in close proximity to the target vessel (304).

The adjustable device delivery system is inserted through an introducer sheath into the entry vessel. An operator would preferably have the adjustable internal door (104) in the open position, at an angle of about 0 degrees, with the locked applied if present. Maintaining the adjustable internal door in the open position ensures a straight passageway of the adjustable device delivery system down the guidewire following, for example, standard Seldinger technique. External visualization can be used to place the instrument until the axle of the adjustable internal door (260) is located in close proximity to the desired exit point for the entry vessel (302) and entry point for target vessel (304), or the bodily compartment connection location. The entire instrument is rotated so that the external slit of the outer cannula (130) faces the target area. The guidewire is then removed with the instrument remaining in the desired location such as demonstrated in FIG. 15d.

Figure 15D:
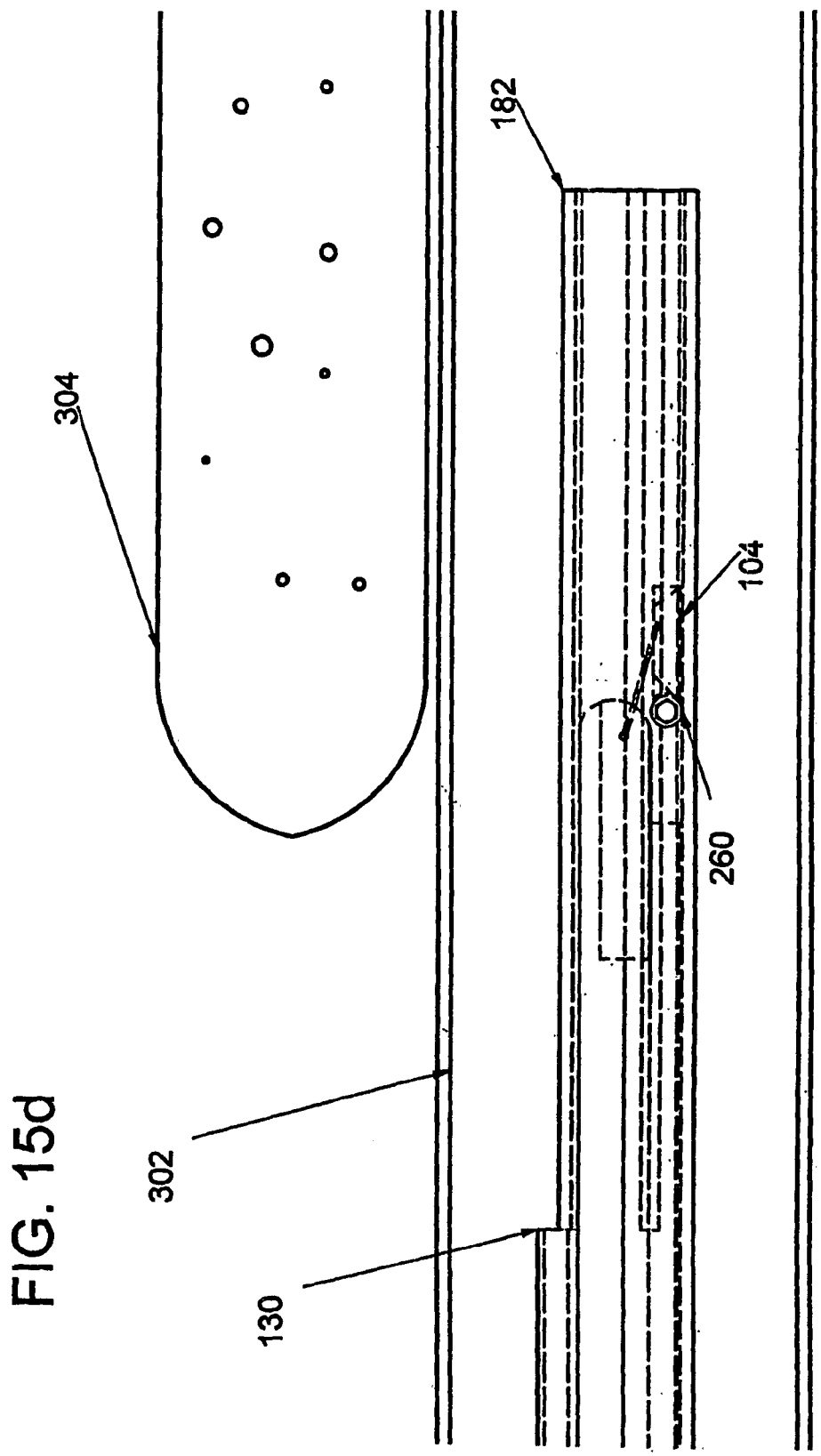
FIG. 15d shows the adjustable device delivery system in position after the guidewire has been removed.

FIG. 15e demonstrates the adjustable device delivery system in the same position as in FIG. 15d. An instrument such as an intravascular ultrasound (308) has been passed down the barrel of the catheter. The adjustable device delivery system would be typically, but not necessarily, advanced under external visualization, such as fluoroscopy, so that the distal tip of the intravascular ultrasound would be overlying the adjustable internal door.

Figure 15F:
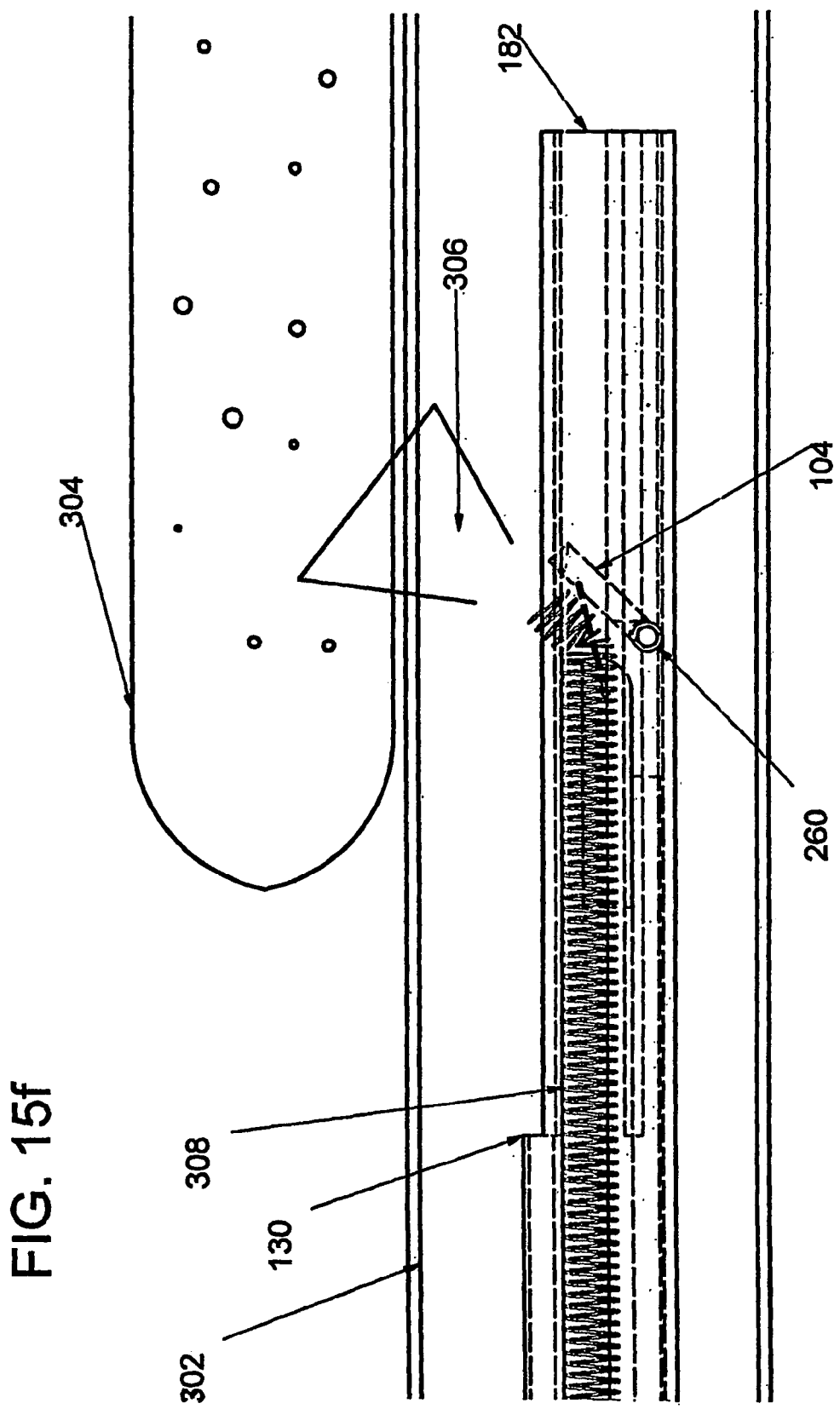
FIG. 15f shows the user-defined angulation of the door directing the tip of the ultrasound device such that the desired target can be visualized.
Figure 15G:
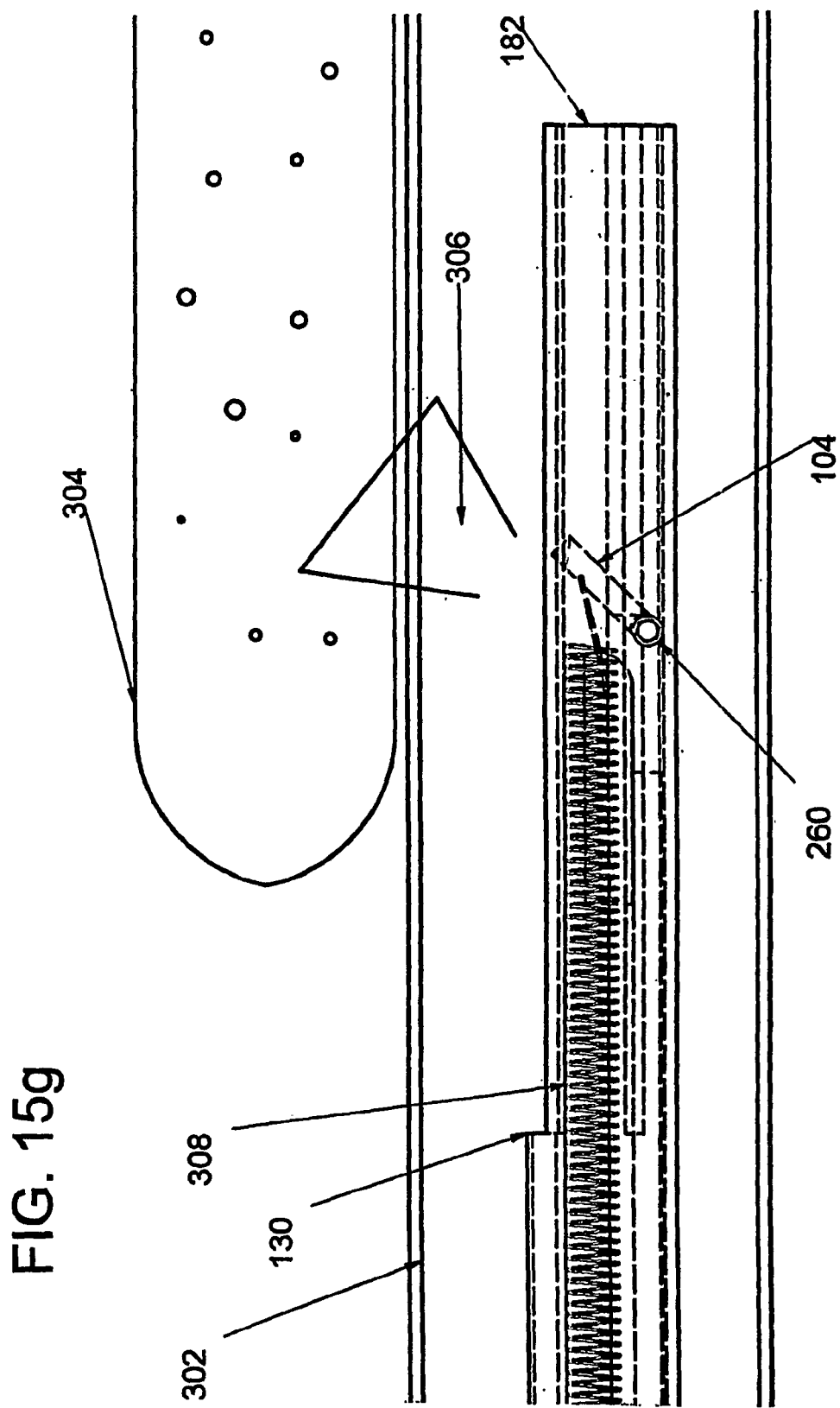
FIG. 15g shows the angulation of the door used to deflect the energy waves of a visualization device such as an intravascular ultrasound.

FIG. 15f demonstrates how the operator would use the steering apparatus on the adjustable device delivery system to adjust the angle of the adjustable internal door. The visual field of the ultrasound (306), and optionally combined with an external visualization technique such as fluoroscopy, would allow the operator to adjust the distal angle and field of view of the ultrasound (306) until the adjustable internal door was in the exact position desired. At this point the operator would lock the position of the door by rotating the lock system until the proximal face of the lock surface was flush with, i.e., butted against, the distal face of the steering apparatus. The resulting frictional forces between the lock system and the steering assembly would prevent unwanted motion of the steering system and, hence, the adjustable internal door during device exchanges and general use of the adjustable device delivery system.

Figure 15H:
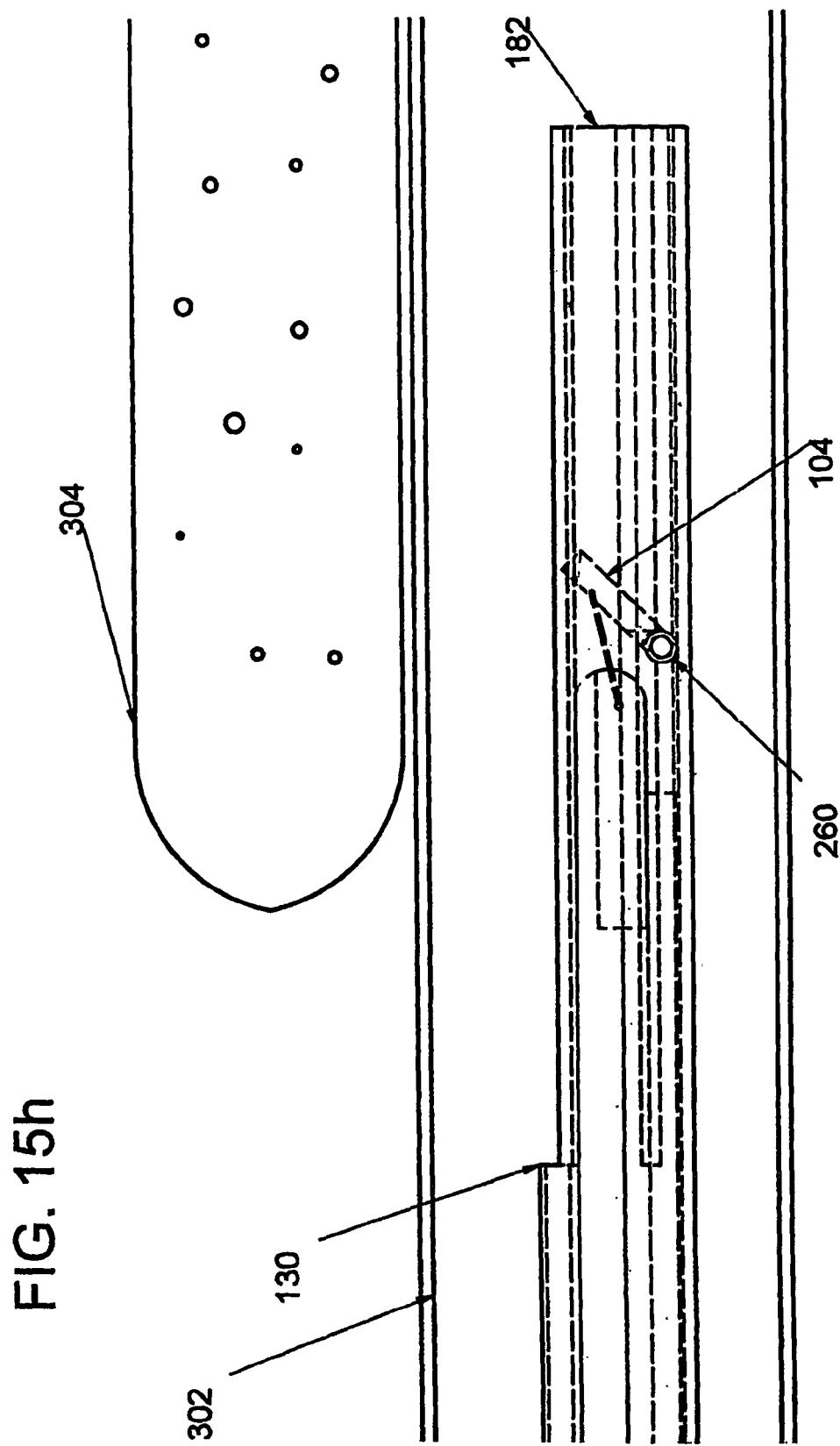
FIG. 15h shows the adjustable internal door locked in position after the ultrasound device has been removed.
Figure 15I:
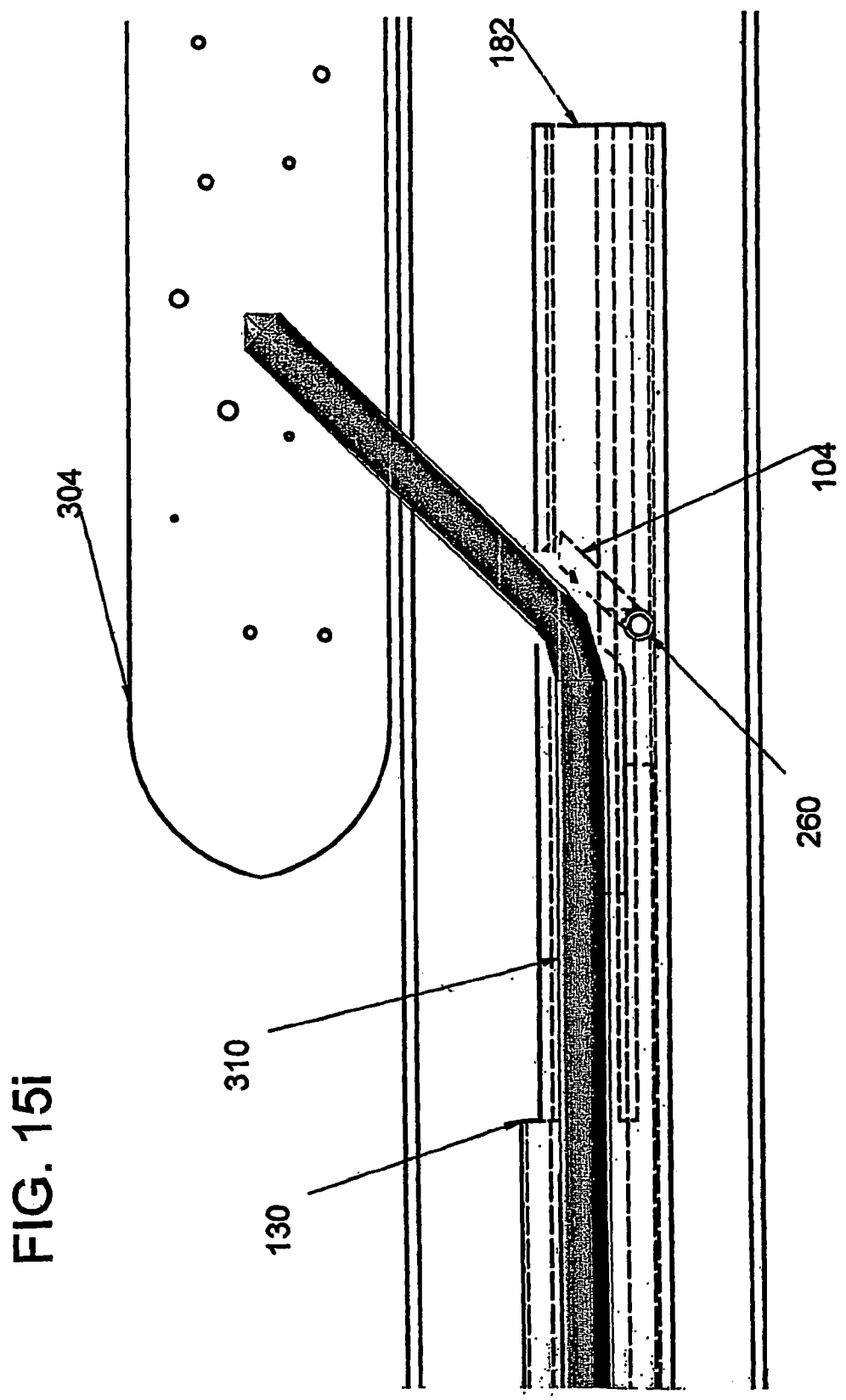
FIG. 15i shows a device, for example a needle, that ahs been placed down the adjustable device delivery system, deflected at the angle defined by the adjustable internal door and delivered into the target lumen or space.

FIG. 15h demonstrates the adjustable device delivery system in the same position after the intravascular ultrasound has been removed. Because of the inherent frictional forces of the steering assembly on the outer cannula or outer cannula cover, if present, and because of the additional frictional forces achieved by application of the lock, the adjustable internal door preferably does not move in between instrument changes. The adjustable internal door therefore remains in the same position as was previously determined by using internal visualization techniques and, optionally, external visualization techniques in conjunction with the intravascular ultrasound.

Figure 15J:
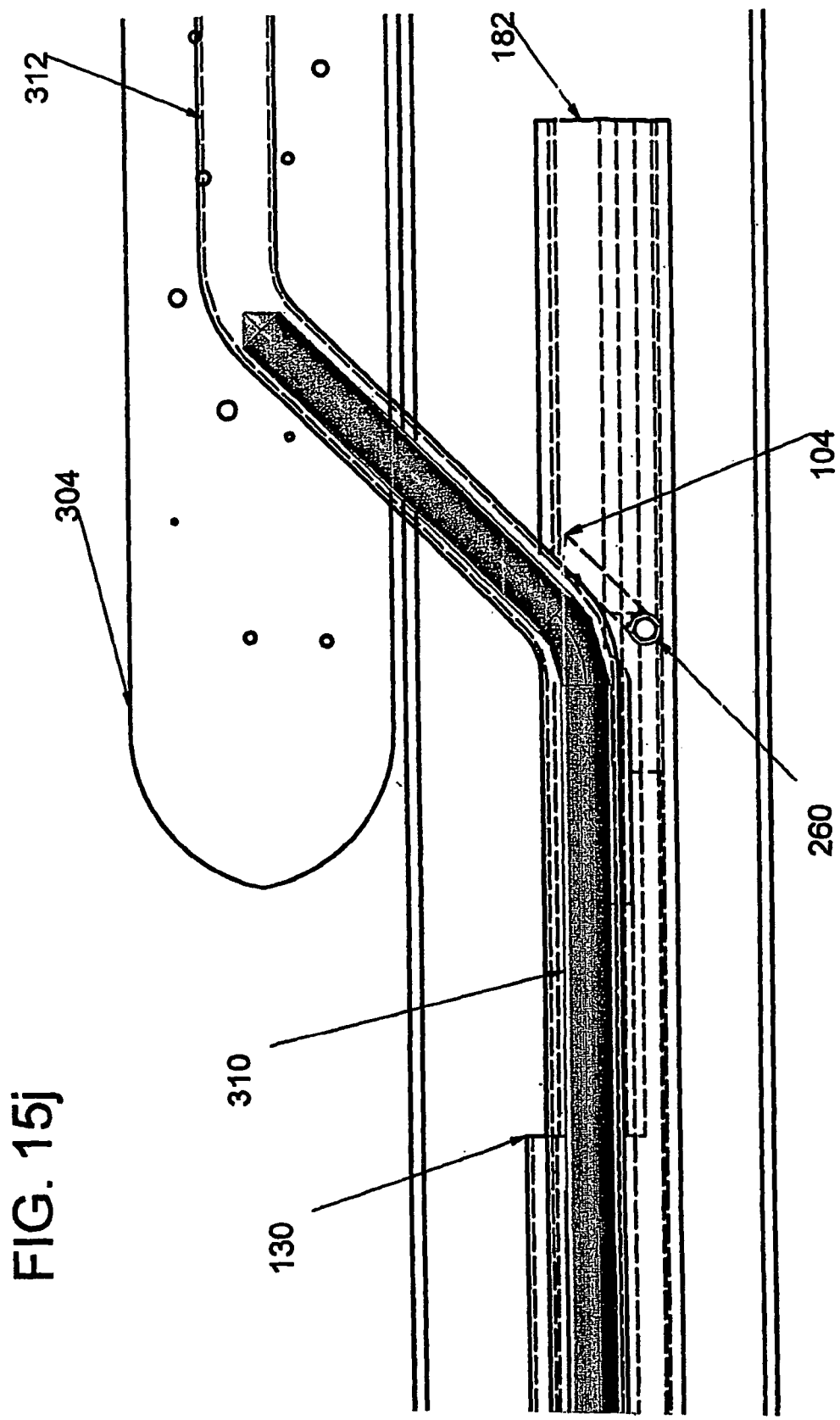
FIG. 15j shows a drainage catheter slid over the needle so that it can connect the two vessels.
Figure 15K:
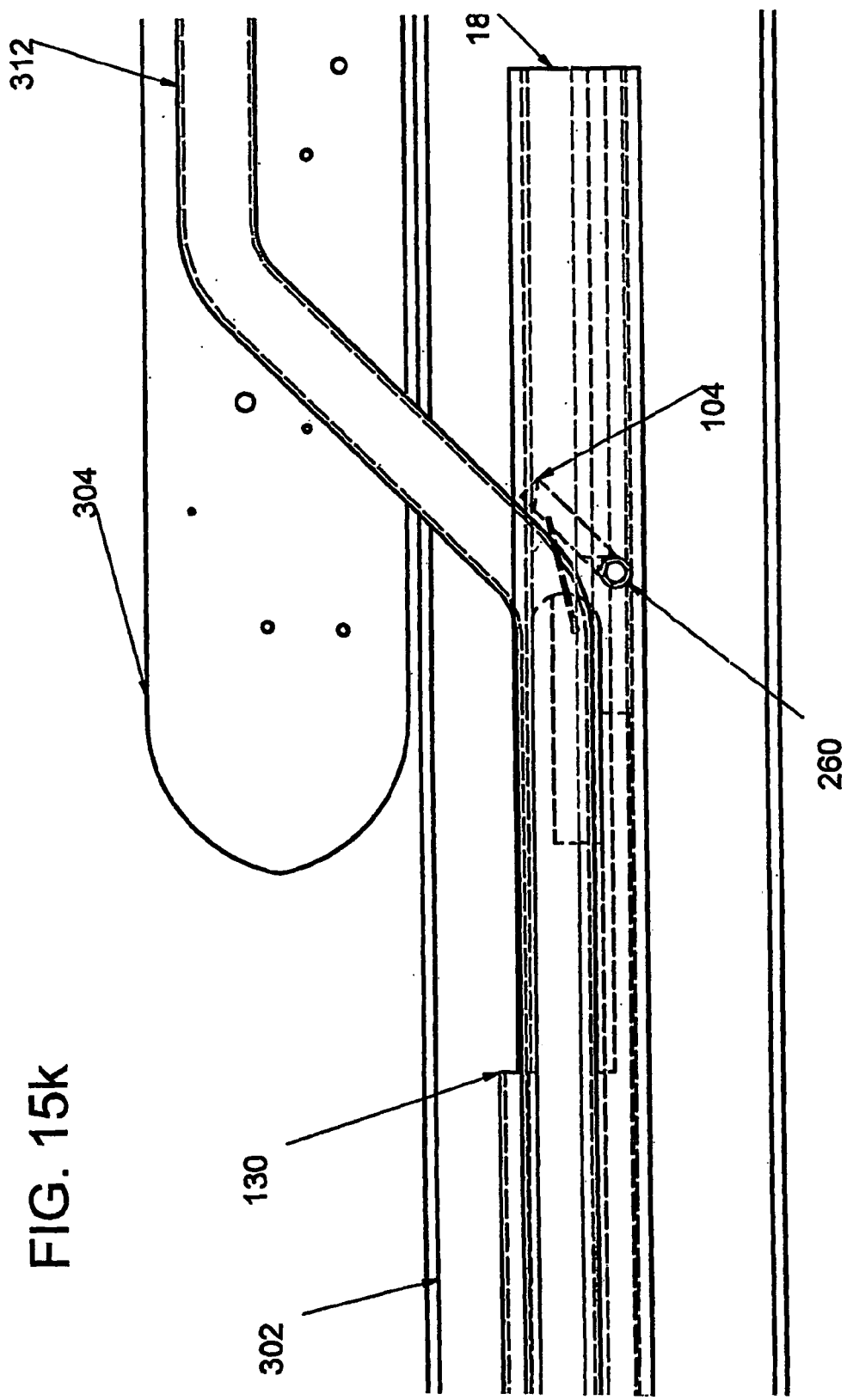
FIG. 15k shows the drainage catheter after the needle has been removed.
Figure 15I:
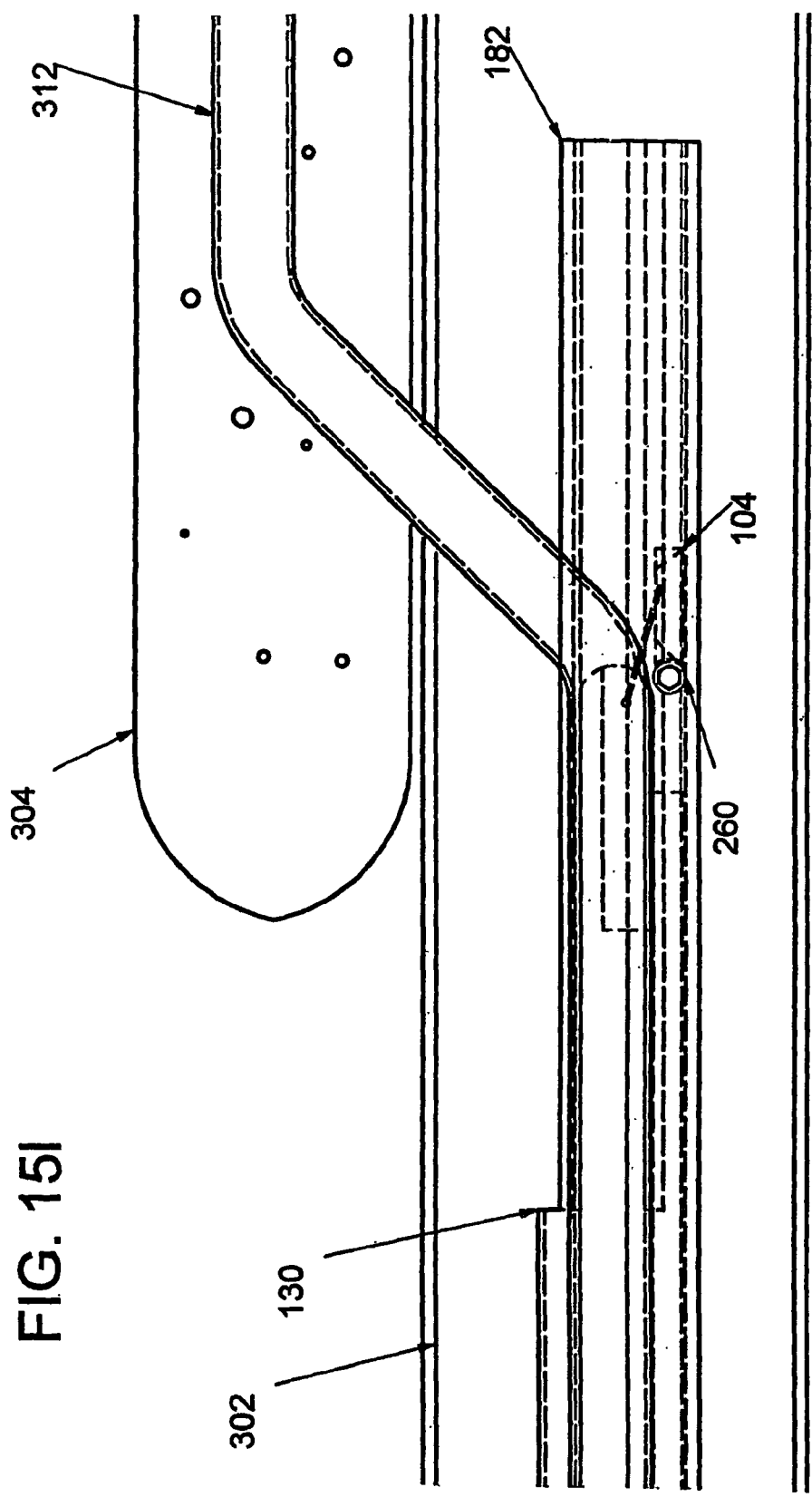

An operator is then able to slide another medical device down the barrel of the adjustable device delivery system such as a needle (310). Because the adjustable internal door is locked in position, the operator could exert sufficient force on the needle and the proximal face of the adjustable internal door to achieve adequate deflection and controlled perforation of vessel lumen and surrounding structures. This technique would be performed under careful external visualization or concomitant internal visualization, the internal visualization device being delivered through the lumen of the adjustable device delivery system along with other devices such as the needle (310). When the needle was in the proper structure, the operator would then have the opportunity for further instrumentation. An example of further instrumentation includes the placement of, for example, a drainage catheter. The operator could slide such a drainage catheter (312) over the needle with the adjustable device delivery system and the adjustable internal door in the same position. Such an operation is shown in FIG. 15j.

After both the needle and the catheter were determined to be in proper position, the operator then removes the needle. This leaves the adjustable internal door in the same locked position with the catheter in the same position, and the adjustable device delivery system in the same position. This is demonstrated in FIG. 15k.

The operator then unlocks the adjustable internal door by releasing the lock system. Releasing the lock system causes the lock system to translate distally (toward the distal end of the outer cannula) so that the distal face of the steering assembly would no longer collide with the proximal face of the lock system. Consequently, the operator is able to turn the steering apparatus such that the drive actuator, inner drive cannula and adjustable internal door moves distally, pushing the adjustable internal door back down to its open position at 0 degrees. The described positions of the adjustable internal door and adjustable device delivery system position are demonstrated in FIG. 15l.

FIG. 15m demonstrates the adjustable device delivery system being removed from the body by pulling in the proximal direction (to the left in the illustration). This Figure demonstrates the final placement of the drainage catheter (312) as well as the adjustable device delivery system's unobstructed removal. That is, the adjustable device delivery system can be removed, through the combination of the slot in the distal portion of the outer cannula and the adjustable internal door, without disturbing a delivered device, such as the drainage catheter (312), including, even, the angle at which it was delivered. Thus, unlike other systems in the art, there is no internal collision between the adjustable device delivery system of the invention and the delivered device because the adjustable internal door (104) can retract to an open, 0 degree position. Further, because the exterior slit of the exterior catheter (130) extends to the distal extent of the outer cannula (182), there is no external collision between the external wall of the adjustable device delivery system and the drainage catheter.

It should be understood that the foregoing disclosure emphasizes certain specific embodiments of the invention and that all modifications or alternatives equivalent thereto are within the spirit and scope of the invention as set forth in the appended claims.

I claim:

1. An adjustable device delivery system comprising: a tubular body having a proximal end, a distal end, a longitudinal axis, a lumen extending within the tubular body, and a slot within the tubular body extending to and including its distal end; and an adjustable internal door comprising a door body with a superior, inferior, proximal, distal and two side surfaces, at least one door hinge hole in the side surfaces of the door body and a door hinge surface on the inferior surface of the door body, the adjustable internal door hingedly coupled to the interior of the tubular body, located opposite the slot in the distal portion of the tubular body, wherein at least one device is slidably connected within the lumen of the tubular body, wherein the at least one device is deflected off of the proximal surface of the adjustable internal door at a user-definable angle and delivered to a target site at the user-definable angle, wherein the tubular body comprises an outer cannula and an inner drive cannula, wherein the inner drive cannula is slidably connected to the inside of the outer cannula, wherein the proximal portion of the inner drive cannula comprises a drive actuator to move the inner drive cannula along the longitudinal axis wherein the drive actuator comprises a drive barrel at the proximal end of the inner drive cannula and a drive shaft of a different diameter than the drive barrel located within the axial length of the drive barrel, wherein the edges defined by the different radial distances at the drive barrel-drive shaft interface provide a leverage means to move the inner drive cannula along the longitudinal axis.

2. The adjustable device delivery system of claim 1, wherein the distal end of the outer cannula is open.

3. The adjustable device delivery system of claim 1, wherein the distal end of the outer cannula contains a slot extending to and including its distal end.

4. The adjustable device delivery system of claim 1, wherein the distal portion of the inner drive cannula comprises an open shaft.

5. The adjustable device delivery system of claim 1, wherein the drive actuator further comprises at least one washer wherein the washer inner-hole diameter is larger than the smaller of the drive barrel diameter or drive shaft diameter but smaller than the larger of the drive barrel diameter or drive shaft diameter wherein the at least one washer resides on the smaller diameter drive barrel or drive shaft and press against the larger diameter drive barrel or drive shaft to move the inner drive cannula along the longitudinal axis.

6. The adjustable device delivery system of claim 5 wherein the drive actuator further comprises at least one washer wherein the washer inner-hole diameter is larger than the drive shaft diameter but smaller than the drive barrel diameter wherein the at least one washer resides on the drive shaft and press against the drive barrel to move the inner drive cannula along the longitudinal axis.

7. The adjustable device delivery system of claim 6, wherein the proximal portion of the outer cannula is threaded to facilitate the rotatable attachment of at least one correspondingly threaded attachment.

8. The adjustable device delivery system of claim 6, further comprising an outer cannula cover that contains an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover is servable as a handle for operation of the adjustable delivery system.

9. The adjustable device delivery system of claim 5, wherein the proximal portion of the outer cannula is threaded to facilitate the rotatable attachment of at least one correspondingly threaded attachment.

10. The adjustable device delivery system of claim 5, further comprising an outer cannula cover that contains an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover is servable as a handle for operation of the adjustable delivery system.

11. The adjustable device delivery system of claim 1, wherein the outer cannula contains an axle shell in its distal end.

12. The adjustable device delivery system of claim 11, wherein the axle shell is located opposite the slot in the outer cannula.

13. The adjustable device delivery system of claim 11, wherein the axle shell holds on its inner surfaces an axle comprising a middle portion and two cylindrical side portions, wherein the outer diameter of the cylindrical side portions of the axle corresponds to the inner diameter of the axle shell, and the size and geometric shape of the middle portion of the axle is the same as or different from the cylindrical side portions of the axle.

14. The adjustable device delivery system of claim 13, wherein the door hinge surface of the adjustable internal door is hingedly coupled to the middle portion of the axle wherein the size and geometric shape of the middle portion of the axle corresponds to the geometric size and shape of the inner surface of the door hinge surface.

15. The adjustable device delivery system of claim 14, further comprising a door connector system moveably connecting the distal end of the inner drive cannula at least one hinge hole to the door hinge holes in the side surfaces of the door body of the adjustable internal door.

16. The adjustable device delivery system of claim 15, wherein the door connector system comprises at least one door connector comprising a shaft with a proximal and a distal end, the proximal end comprising a proximal inner drive cannula insertion tab, which is moveably connected to the hinge hole in the distal end of the inner drive cannula and the distal end comprising a distal door insertion tab, which is moveably connected to the door hinge hole in the side surface of the door body.

17. The adjustable device delivery system of claim 1, wherein the distal portion of the outer cannula and the distal portion of the inner drive cannula contain at least one cut away region wherein the adjustable internal door and hinge move longitudinally.

18. The adjustable device delivery system of claim 1, wherein the proximal portion of the outer cannula is threaded to facilitate the rotatable attachment of at least one correspondingly threaded attachment.

19. The adjustable device delivery system of claim 18, 9 or 7, wherein the attachment comprises a steering assembly comprising a center shaft, two or more cylindrical cutout areas wherein the outer diameter of the drive actuator drive barrel fits within the inner diameter of the steering assembly center shaft, which shaft is cut out and extends the longitudinal length of the steering assembly, a cylindrical cutout area in the distal end of the steering assembly of an inner diameter corresponding to the outer diameter of the proximal portion of the threaded outer cannula, the cylindrical cutout correspondingly threaded to rotatably attach to the proximal end of the outer cannula enabling longitudinal movement of the steering system, a cylindrical cutout area of an inner diameter corresponding to the outer diameter of the drive actuator drive shaft and a longitudinal length wherein the cylindrical cutout is fittable over a drive actuator drive shaft of larger diameter than the drive actuator drive barrel or within a detent created when the drive actuator drive shaft diameter is smaller than the drive actuator drive barrel, wherein the surfaces of the steering assembly correspond to the surfaces of the drive actuator and the outer cannula, the steering assembly is freely rotatable around the longitudinal axes of the drive actuator and the rotational motion of the steering assembly translates into proximal and distal translation of the steering assembly in relation to the outer cannula.

20. The adjustable device delivery system of claim 19, further comprising at least one cylindrical slot of corresponding diameter and longitudinal position within the steering assembly to interact with at least one washer present at the proximal end of the outer cannula and at the diametrically differing interfaces between the drive barrel and drive shaft.

21. The adjustable device delivery system of claim 19, further comprising a lock system comprising an inner surface and an outer surface, the inner surface of a diameter corresponding to the outer diameter of the proximal end of the outer cannula and threaded to facilitate its rotatable attachment to the correspondingly threaded proximal end of the outer cannula.

22. The adjustable device delivery system of claim 21, wherein the lock system locks the position of the steering assembly, drive actuator, inner drive cannula and adjustable internal door by rotatably butting against the steering assembly on the threads of the outer cannula preventing the movement of the steering assembly, drive actuator, inner drive cannula and adjustable internal door.

23. The adjustable device delivery system of claim 21, wherein the lock system unlocks the position of the steering assembly, drive actuator, inner drive cannula and adjustable internal door by rotatably moving away from the steering assembly on the threads of the outer cannula enabling the movement of the steering assembly, drive actuator, inner drive cannula and adjustable internal door.

24. The adjustable device delivery system of claim 18, 9 or 7, further comprising a lock system comprising an inner surface and an outer surface, the inner surface of a diameter corresponding to the outer diameter of the proximal end of the outer cannula and threaded to facilitate its rotatable attachment to the correspondingly threaded proximal end of the outer cannula.

25. The adjustable device delivery system of claim 1, further comprising an outer cannula cover that contains an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover is servable as a handle for operation of the adjustable delivery system.

26. The adjustable device delivery system of claim 25, wherein the proximal portion of the interior tract of the outer cannula cover is threaded to rotatably attach to an outer cannula that is correspondingly threaded at its proximal end.

27. The adjustable device delivery system of claim 25, wherein the outer cannula cover is bonded to the proximal end of the outer cannula, the outer cannula residing within the interior tract of the outer cannula cover.

28. The adjustable device delivery system of claim 25, wherein the exterior of the proximal portion of the outer cannula cover is threaded to facilitate the rotatable attachment of correspondingly threaded attachments.

29. The adjustable device delivery system of claim 28, wherein the proximal end of the outer cannula includes a raised ridge of a larger diameter than the proximal end of the outer cannula.

30. The adjustable device delivery system of claim 29, wherein the raised ridge is of a diameter equivalent to or larger than the proximal end of the outer cannula cover.

31. The adjustable device delivery system of claim 29, wherein the raised ridge acts as a physical stop for the steering assembly.

32. The adjustable device delivery system of claim 28, wherein the attachment comprises a steering assembly comprising a center shaft, two or more cylindrical cutout areas wherein the outer diameter of the drive actuator drive barrel fits into the inner diameter of the steering assembly center shaft, which shaft is cut out and extends the longitudinal length of the steering assembly, a cylindrical cutout area in the distal end of the steering assembly of an inner diameter corresponding to the outer diameter of the proximal portion of the threaded outer cannula cover, the cylindrical cutout correspondingly threaded to rotatably attach to the proximal end of the outer cannula cover enabling longitudinal movement of the steering system, a cylindrical cutout area of an inner diameter corresponding to the outer diameter of the drive actuator drive shaft and a longitudinal length wherein the cylindrical cutout is fittable over a drive actuator drive shaft of larger diameter than the drive actuator drive barrel or within a detent created when the drive actuator drive shaft diameter is smaller than the drive actuator drive barrel, wherein the surfaces of the steering assembly correspond to the surfaces of the drive actuator and the outer cannula cover, the steering assembly is freely rotatable around the longitudinal axes of the drive actuator and the rotational motion of the steering assembly translates into proximal and distal translation of the steering assembly in relation to the outer cannula.

33. The adjustable device delivery system of claim 32, further comprising at least one cylindrical slot of corresponding diameter and longitudinal position within the steering assembly to interact with at least one washer present at the proximal end of the outer cannula and outer cannula cover and at the diametrically differing interfaces between the drive barrel and drive shaft.

34. The adjustable device delivery system of claim 32, further comprising a lock system comprising an inner surface and an outer surface, the inner surface of a diameter corresponding to the outer diameter of the proximal end of the outer cannula cover and threaded to facilitate its rotatable attachment to the correspondingly threaded proximal end of the outer cannula cover.

35. The adjustable device delivery system of claim 34, wherein the lock system locks the position of the steering assembly, drive actuator, inner drive cannula and adjustable internal door by rotatably butting against the steering assembly on the threads of the outer cannula cover preventing the movement of the steering assembly, drive actuator, inner drive cannula and adjustable internal door.

36. The adjustable device delivery system of claim 34, wherein the lock system unlocks the position of the steering assembly, drive actuator, inner drive cannula and adjustable internal door by rotatably moving away from the steering assembly on the threads of the outer cannula cover enabling the movement of the steering assembly, drive actuator, inner drive cannula and adjustable internal door.

37. The adjustable device delivery system of claim 28, further comprising a lock system comprising an inner surface and an outer surface, the inner surface of a diameter corresponding to the outer diameter of the proximal end of the outer cannula cover and threaded to facilitate its rotatable attachment to the correspondingly threaded proximal end of the outer cannula cover.

38. The adjustable device delivery system of claim 1, wherein the drive actuator comprises a drive barrel of a smaller diameter than the drive shaft, and further comprising an outer cannula cover that contains an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover serves as a handle for operation of the adjustable delivery system.

39. The adjustable device delivery system of claim 1, wherein the drive actuator comprises a drive barrel of a larger diameter than the drive shaft, and further comprising an outer cannula cover that contains an interior tract, wherein the diameter of the outer cannula cover interior tract corresponds to the outer diameter of the outer cannula and the outer cannula cover is attached to the proximal end of the outer cannula, the outer cannula residing within the interior tract of the outer cannula cover, and wherein the distal portion of the outer cannula cover is servable as a handle for operation of the adjustable delivery system.

40. The adjustable device delivery system of claim 1, wherein the adjustable internal door deflects electromagnetic radiation, and further comprising a means for detecting electromagnetic radiation deflected by the adjustable internal door, the radiation moving in a distal-to-proximal or proximal-to-distal direction in the adjustable device delivery system.

41. The adjustable device delivery system of claim 1, wherein the adjustable internal door focuses electromagnetic radiation, and further comprising a means for detecting electromagnetic radiation focused by the adjustable internal door, the radiation moving in a distal-to-proximal or proximal-to-distal direction in the adjustable device delivery system.

42. The adjustable device delivery system of claim 1, wherein the tubular body is flexible.

* * * * *